US009933437B2

(12) United States Patent
Hansen et al.

(10) Patent No.: US 9,933,437 B2
(45) Date of Patent: Apr. 3, 2018

(54) EARLY DETERMINATION OF PREGNANCY STATUS IN RUMINANTS

(71) Applicant: Colorado State University Research Foundation, Fort Collins, CO (US)

(72) Inventors: Thomas R. Hansen, Fort Collins, CO (US); Jessica Prenni, Fort Collins, CO (US); Torrance M. Nett, Bellvue, CO (US); Kevin McSweeney, Loveland, CO (US); Jared Romero, Alamosa, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 468 days.

(21) Appl. No.: 14/523,615

(22) Filed: Oct. 24, 2014

(65) Prior Publication Data

US 2015/0114310 A1    Apr. 30, 2015

Related U.S. Application Data

(60) Provisional application No. 61/895,887, filed on Oct. 25, 2013.

(51) Int. Cl.
| | |
|---|---|
| *G01N 33/68* | (2006.01) |
| *A01K 29/00* | (2006.01) |
| *A01K 67/00* | (2006.01) |
| *H01J 49/00* | (2006.01) |
| *H01J 49/26* | (2006.01) |

(52) U.S. Cl.
CPC ......... *G01N 33/689* (2013.01); *A01K 29/005* (2013.01); *A01K 67/00* (2013.01); *G01N 33/6866* (2013.01); *H01J 49/0027* (2013.01); *H01J 49/26* (2013.01)

(58) Field of Classification Search
CPC ............. G01N 33/689; G01N 33/6866; A01K 29/005; A01K 67/00; H01J 49/0027; H01J 49/26
See application file for complete search history.

(56) References Cited

U.S. PATENT DOCUMENTS 7,125,728 B2 * 10/2006 Ott ..................... C12Q 1/6876
                                                      435/5
2003/0224452 A1    12/2003 Colgin et al.

FOREIGN PATENT DOCUMENTS

WO         03028582         4/2003

OTHER PUBLICATIONS

Zhu et al., Enzyme-Linked Immunosorbent Assay for Ovine Interferon-t, Journal of Interferon and Cytokine Research 16:147-150 (1996).*

Van Der Vekiens et al., Human and equine cardiovascular endocrinology: beware to compare, Cardiovascular Endocrinology 2013, vol. 2, No. 4, pp. 67-76.*
Torzewski et al., Animal Models of C-Reactive Protein, Hindawl Publishing Corporation, Mediators of Inflammation, vol. 2014, Article ID 683598, 2014, pp. 1-7.*
Youngquist., Pregnancy Diagnosis, Proceedings, Applied Reproductive Strategies in Beef Cattle, Aug. 30 and 31, 2006, pp. 329-338.*
Lucy et al., Pregnancy determination by palpation and beyond, Proceedings, Applied Reproductive Strategies in Beef Cattle, Dec. 3-4, 2012, pp. 309-316. (Year: 2012).*
Colles, et al., "Cholesterol interaction with recombinant human sterol carrier protein-2" Lipids 30(9): 795-803. Dec. 31, 1995.
Danet-Desnoyers, et al., "Natural and recombinant bovine interferon tau regulate basal and oxytocin-induced secretion of prostaglandins F2 alpha and E2 by epithelial cells and stromal cells in the endometrium" Reprod Fertil Dev 6(2): 193-202. Dec. 31, 1994.
Danielsen, et al., ""Nonclassical" secretion of annexin A2 to the lumenal side of the enterocyte brush border membrane" Biochemistry 42(49): 14670-6. Dec. 31, 2003.
Davis, et al., "The corpus luteum: an ovarian structure with maternal instincts and suicidal tendencies" Front Biosci 7: d1949-78. Sep. 1, 2002.
Davis, et al., "Progesterone inhibits oxytocin- and prostaglandin F2alpha-stimulated increases in intracellular calcium concentrations in small and large ovine luteal cells" Biol Reprod 82(2): 282-8. Oct. 7, 2009.
Deban, et al., "Pentraxins in innate immunity: lessons from PTX3" Cell Tissue Res 343(1): 237-49. Aug. 4, 2010.
Dennis, et al., "Role of phospholipase in generating lipid second messengers in signal transduction" FASEB J 5(7): 2068-77. Dec. 31, 1991.
Diekman, et al., "Effect of prostaglandin F2alpha on the number of LH receptors in ovine corpora lutea" Biol Reprod 19(5): 1010-3. Dec. 31, 1978.
Diekman, et al., "Validation of methods and quantification of luteal receptors for LH throughout the estrous cycle and early pregnancy in ewes" Biol Reprod 19(5): 999-1009. Dec. 31, 1978.
Dinan, et al., "Effects and applications of arthropod steroid hormones (ecdysteroids) in mammals" J Endocrinol 191 (1): 1-8. Dec. 31, 2006.
Diskin, et al., "Embryonic and early foetal losses in cattle and other ruminants" Reprod Domest Anim 43 Suppl 2: 260-7. Dec. 31, 2008.
Diskin, et al., "Embryo survival in dairy cows managed under pastoral conditions" Anim Reprod Sci 96(3-4): 297-311. Aug. 3, 2006.
Dwyer, et al., "Effect of prostaglandin F-2 alpha on ovarian enzyme activity in the hysterectomized guinea-pig" J Reprod Fertil 56(1): 85-8. Dec. 31, 1979.

(Continued)

*Primary Examiner* — Gary Counts
(74) *Attorney, Agent, or Firm* — McKee, Voorhees & Sease, PLC

(57) ABSTRACT

The present invention provides compositions and methods for detection schemes for ascertaining pregnancy status of an animal. The compositions and methods employ interferon-tau (IFNT) and/or antibodies specific for IFNT. Methods of the present invention detect the presence of IFNT in samples obtained from animals as an early indicator of pregnancy. Methods are provided to identify non-pregnant animals so that management decisions regarding rebreeding can be made earlier compared to existing approaches.

15 Claims, 8 Drawing Sheets

(56) References Cited

OTHER PUBLICATIONS

Dwyer, et al., "Effect of prostaglandin F-2 alpha on plasma levels of progesterone and pregnenolone in the hysterectomized guinea-pig" J Reprod Fertil 56(1): 81-4. Dec. 31, 1979.
Ellish, et al., "A prospective study of early pregnancy loss" Hum Reprod 11(2): 406-12. Dec. 31, 1996.
Epstein, et al., "Acute action of luteinizing hormone on mouse Leydig cells: accumulation of mitochondrial phosphoproteins and stimulation of testosterone synthesis" Mol Cell Endocrinol 81(1-3): 113-26. Dec. 31, 1991.
Epstein, et al., "Regulation of steroid hormone biosynthesis. Identification of precursors of a phosphoprotein targeted to the mitochondrion in stimulated rat adrenal cortex cells" J Biol Chem 266(29): 19739-45. Oct. 15, 1991.
Esemuede, et al., "The role of thrombospondin-1 in human disease" J Surg Res 122(1): 135-42. Dec. 31, 2004.
Farin, et al., "Morphometric analysis of cell types in the ovine corpus luteum throughout the estrous cycle" Biol Reprod 35(5): 1299-308. Dec. 31, 1986.
Farkash, et al., "Preparation of antiserum to rat cytochrome P-450 cholesterol side chain cleavage, and its use for ultrastructural localization of the immunoreactive enzyme by protein A-gold technique" Endocrinology 118(4): 1353-65. Dec. 31, 1986.
Faulkner, et al., "A comparison of the bovine uterine and plasma proteome using iTRAQ proteomics" Proteomics 12(12): 2014-23. Dec. 31, 2012.
Faure, et al., "Annexin 2 "secretion" accompanying exocytosis of chromaffin cells: possible mechanisms of annexin release" Exp Cell Res 276(1): 79-89. Dec. 31, 2002.
Ferreira, et al., "Prostaglandins: their disappearance from and release into the circulation" Nature 216(5118): 868-73. Dec. 2, 1967.
Fitz, et al., "Characterization of two steroidogenic cell types in the ovine corpus luteum" Biol Reprod 27(3): 703-11. Dec. 31, 1982.
Fleury, et al., "In vivo effects of adrenocorticotrophin on the expression of the hamster steroidogenic acute regulatory protein" J Mol Endocrinol 21(2): 131-9. Dec. 31, 1998.
Flohr, et al., "The central interactive region of human MxA GTPase is involved in GTPase activation and interaction with viral target structures" FEBS Lett 463(1-2): 24-8. Dec. 31, 1999.
Flower, "Eleventh Gaddum memorial lecture. Lipocortin and the mechanism of action of the glucocorticoids" Br J Pharmacal 94(4): 987-1015. Dec. 31, 1988.
Flower, et al., "Lipocortin-1: cellular mechanisms and clinical relevance" Trends Pharmacol Sci 15(3): 71-6. Mar. 31, 1994.
Forde, et al., "Proteomic analysis of uterine fluid during the pre-implantation period of pregnancy in cattle", Reproduction, 147, p. 575-587 and Supplemental Table 2, part 213. Jan. 29, 2014.
Freund, et al., "Improved Detection of Quantitative Differences Using a Combination of Spectral Counting and MS/MS Total Ion Current" J Proteome Res. Apr. 5, 2013.
Fricke, "Scanning the future—ultrasonography as a reproductive management tool for dairy cattle" J Dairy Sci 85(8): 1918-26. Dec. 31, 2002.
Gao, et al., "Select nutrients in the ovine uterine lumen. I. Amino acids, glucose, and ions in uterine lumenal flushings of cyclic and pregnant ewes" Biol Reprod 80(1): 86-93. Aug. 27, 2008.
Garlanda, et al., "Inflammatory reaction and implantation: the new entries PTX3 and D6" Placenta 29 Suppl B: 129-34. Dec. 31, 2008.
Gentry, et al., "Characterization of Ovine Stem Cell Factor Messenger Ribonucleic Acid and Protein in the Corpus Luteum throughout the Luteal Phase", Biology of Reproduction, 54, p. 970-979. Dec. 31, 1996.
Gerke, et al., "Annexins: linking Ca2+ signalling to membrane dynamics" Nat Rev Mal Cell Biol 6(6): 449-61. Jun. 30, 2005.
Gifford, et al., "Regulation of interferon-stimulated genes in peripheral blood leukocytes in pregnant and bred, nonpregnant dairy cows" J Dairy Sci 90(1): 274-80. Dec. 31, 2000.
Glass, et al., "Cytosolic receptor for estradiol in the corpus luteum of the ewe: variation throughout the estrous cycle and distribution between large and small steroidogenic cell types" Biol Reprod 31(5): 967-74. Dec. 31, 1984.
Godkin, et al., "Purification and properties of a major, low molecular weight protein released by the trophoblast of sheep blastocysts at day 13-21" Journal of reproduction and fertility 65: 141-150. Dec. 31, 1982.
Godkin, et al., "Ovine trophoblast protein 1, an early secreted blastocyst protein, binds specifically to uterine endometrium and affects protein synthesis" Endocrinology 114: 120-130. Dec. 31, 1984.
Godkin, et al. "The role of trophoblast interferons in the maintenance of early pregnancy in ruminants" Am J Reprod Immunol 37(1): 137-43. Dec. 31, 1997.
Gomez, et al., "Embryonic sex induces differential expression of proteins in bovine uterine fluid" J Proteome Res 12(3): 1199-210. Feb. 4, 2013.
Gray, et al., "Identification of endometrial genes regulated by early pregnancy, progesterone, and interferon tau in the ovine uterus" Biol Reprod 74(2): 383-94. Oct. 26, 2005.
Greenaway, et al., "Thrombospondin-1 inhibits VEGF levels in the ovary directly by binding and internalization via the low density lipoprotein receptor-related protein-1 (LRP-1)" J Cell Physiol 210(3): 807-18. Mar. 31, 2007.
Groenendaal, et al., "An economic spreadsheet model to determine optimal breeding and replacement decisions dairy cattle" J Dairy Sci 87: 2146-2157. Dec. 31, 2004.
Guo, et al., "Thrombospondin 1 and type I repeat peptides of thrombospondin 1 specifically induce apoptosis of endothelial cells" Cancer Res 57(9): 1735-42. May 1, 1997.
Gupta, et al., "Binding and displacement of vascular endothelial growth factor (VEGF) by thrombospondin: effect on human microvascular endothelial cell proliferation and angiogenesis" Angiogenesis 3(2): 147-58. Dec. 31, 1999.
Haas, et al., "Interferon induces a 15-kilodalton protein exhibiting marked homology to ubiquitin" J Biol Chem 262(23): 11315-23. Aug. 15, 1987.
Hansen, et al., "Endocrine Conceptus Signaling in Ruminants" Animal Reproduction, vol. 10, No. 3, pp. 310-321. Aug. 29, 2013.
Han, et al., "Low blood ISG15 mRNA and progesterone levels are predictive of non-pregnant dairy cows" The Journal endocrinology 191: 505-512. Dec. 31, 2006.
Hansen, et al., "In vitro synthesis and secretion of ovine trophoblast protein-1 during the period of maternal recognition of pregnancy" Endocrinology 117(4): 1424-30. Dec. 31, 1985.
Hansen, et al., "Interferon RNA of embryonic origin is expressed transiently during early pregnancy in the ewe" J Biol Chem. 263(26): 12801-12804. Sep. 15, 1988.
Harrison, et al., "Progesterone production, LH receptors, and oxytocin secretion by ovine luteal cell types on days 6, 10 and 15 of the oestrous cycle and day 25 of pregnancy" J Reprod Fertil 79(2): 539-48. Dec. 31, 1987.
Hawkins, et al., "Regulation of messenger ribonucleic acid encoding 3 beta-hydroxysteroid dehydrogenase/delta 5-delta 4 isomerase in the ovine corpus luteum" Biol Reprod 48(5): 1185-90. Dec. 31, 1993.
Henkes, et al., "Acid sphingomyelinase involvement in tumor necrosis factor alpha-regulated vascular and steroid disruption during luteolysis in vivo" Proc Natl Acad Sci U S A 105(22): 7670-5. Jun. 3, 2008.
Herbert, et al., "Pregnancy losses in young Australian women: findings from the Australian Longitudinal Study on Women's Health" Womens Health Issues 19(1): 21-9. Dec. 31, 2009.
Horisberger, et al., "Interferon induces a unique protein in mouse cells bearing a gene for resistance to influenza virus" Proc Natl Acad Sci U S A 80(7): 1910-4. Apr. 30, 1983.
Hou, et al., "Prostaglandin F2alpha stimulates the expression and secretion of transforming growth factor B1 via induction of the early growth response 1 gene (EGR1) in the bovine corpus luteum" Mol Endocrinol 22(2): 403-14. Oct. 4, 2007.

(56) References Cited

OTHER PUBLICATIONS

Hoyer, et al., "Hormone-independent activation of adenylate cyclase in large steroidogenic ovine luteal cells does not result in increased progesterone secretion" Endocrinology 114(2): 604-8. Dec. 31, 1984.
Huang, et al., "Noninhibitory PAI-1 enhances plasmin-mediated matrix degradation both in vitro and in experimental nephritis" Kidney Int 70(3): 515-22. Jun. 21, 2006.
Hugentobler, et al., "Effects of changes in the concentration of systemic progesterone on ions, amino acids and energy substrates in cattle oviduct and uterine fluid and blood" Reprod Fertil Dev 22(4): 684-94. Dec. 31, 2010.
Huie, et al., "Effect of chronic ipsilateral or contralateral intrauterine infusion of prostaglandin E1 (PGE1) on luteal function of unilaterally ovariectomized ewes" Prostaglandins 21(6): 945-55. Jun. 30, 1981.
Humblot, "Use of pregnancy specific proteins and progesterone assays to monitor pregnancy and determine the timing, frequencies and sources of embryonic mortality in ruminants" Theriogenology 56(9): 1417-33. Dec. 31, 2001.
International Searching Authority, "The International Search Report and the Written Opinion", issued in connection to PCT/US2014/062246, 10 pages, dated Feb. 12, 2015.
Imakawa, et al., "Interferon-like sequence of ovine trophoblast protein secreted by embryonic trophectoderm" Nature 330: 377-379. Nov. 30, 1987.
Indiveri, et al. "The mitochondrial carnitine/acylcarnitine carrier: function, structure and physiopathology" Mol Aspects Med 32(4-6): 223-33. Dec. 31, 2011.
Inskeep, et al., "Local component of utero-ovarian relationships in the ewe" J Anim Sci 25(4): 1164-8. Dec. 31, 1966.
Inskeep, et al., "Effects of intrafollicular injections of prostaglandins in non-pregnant and pregnant ewes" J Anim Sci 41(4): 1098-104. Dec. 31, 1975.
Irizarry, et al., "Exploration, normalization, and summaries of high density oligonucleotide array probe level data" Biostatistics 4(2): 249-64. Dec. 31, 2003.
Jimenez, et al., "Signals leading to apoptosis-dependent inhibition of neovascularization by thrombospondin-1" Nat Med 6(1): 41-8. Jan. 31, 2000.
Jockusch, et al., "The profile of profilins" Rev Physiol Biochem Pharmacol 159: 131-49. Dec. 31, 2007.
Johnson, et al., "Expression, Purification, and Characterization of Interferon—Produced in Pichia pastoris Grown in a Minimal Medium" Journal of Interferon and Cytokine Research, vol. 19, pp. 631-636. Jun. 1, 1999.
Johnson, et al., "Endometrial ISG17 mRNA and a related mRNA are induced by interferon-tau and localized to glandular epithelial and stromal cells from pregnant cows" Endocrine 10(3): 243-52. Jun. 30, 1999.
Johnson, et al., "Pregnancy and interferon-tau induce conjugation of bovine ubiquitin cross-reactive protein to cytosolic uterine proteins" Biol Reprod 58(4): 898-904. Dec. 31, 1998.
Johnson, et al., "Interferon-tau and progesterone regulate ubiquitin cross-reactive protein expression in the ovine uterus" Biol Reprod 62(3): 622-7. Dec. 31, 2000.
Johnson, et al., "Expression of the interferon tau inducible ubiquitin cross-reactive protein in the ovine uterus" Biol Reprod 61(1): 312-8. Dec. 31, 1999.
Johnson, et al., "Effects of the estrous cycle, pregnancy, and interferon tau on 2',5'-oligoadenylate synthetase expression in the ovine uterus" Biol Reprod 64(5): 1392-9. Dec. 31, 2001.
Johnson, et al., "Carnitine-dependent oxidation of prostaglandins" J Biol Chem 247(17): 5656-8. Dec. 31, 1972.
Joyce, et al., "Interferon stimulated gene 15 conjugates to endometrial cytosolic proteins and is expressed at the uterine-placental interface throughout pregnancy in sheep" Endocrinology 146(2): 675-84. Dec. 31, 2005.
Juengel, et al., "Effect of dose of prostaglandin F(2alpha) on steroidogenic components and oligonucleosomes in ovine luteal tissue" Biol Reprod 62(4): 1047-51. Dec. 31, 2000.
Juengel, et al., "Luteal expression of steroidogenic factor-1 mRNA during the estrous cycle and in response to luteotropic and luteolytic stimuli in ewes" Endocrine 9(3): 227-32. Dec. 31, 1998.
Juengel, et al., "Hormonal regulation of messenger ribonucleic acid encoding steroidogenic acute regulatory protein in ovine corpora lutea" Endocrinology 136(12): 5423-9. Dec. 31, 1995.
Kaczan-Bourgois, et al., "Increased content of annexin II (p36) and p11 in human placenta brush-border membrane vesicles during syncytiotrophoblast maturation and differentiation" Placenta 17(8): 669-76. Dec. 31, 1996.
Kahn, et al., "[Sonographic diagnosis of early pregnancy in horses, cattle, sheep, goats, swine, dogs and cats. Standard values and limitations]" Berl Munch Tierarztl Wochenschr 103(6): 206-11. Mar. 7, 1990.
Kall, et al., "Assigning significance to peptides identified by tandem mass spectrometry using decoy databases" J Proteome Res 7(1): 29-34. Dec. 8, 2007.
Kaltenbach, et al., "Effect of hypophysectomy on the formation and maintenance of corpora lutea in the ewe" Endocrinology 82(4): 753-9. Dec. 31, 1968.
Karsch, et al., "Prolonged maintenance of the corpus luteum of the ewe by continuous infusion of luteinizing hormone" Biol Reprod 4(2): 129-36. Dec. 31, 1971.
Keller, et al., "Empirical statistical model to estimate the accuracy of peptide identifications made by MS/MS and database search" Anal Chem 74(20): 5383-5392. Sep. 12, 2002.
Kerban, et al., "Human chorionic gonadotropin induces an inverse regulation of steroidogenic acute regulatory protein messenger ribonucleic acid in theca interna and granulosa cells of equine preovulatory follicles" Endocrinology 140(2): 667-74. Dec. 31, 1999.
Khan, et al., "Role of laminin in matrix induction of macrophage urokinase-type plasminogen activator and 92-kDa metalloproteinase expression" J Biol Chem 272(13): 8270-5. Dec. 31, 1997.
Khanna, et al., "Heat shock protein-70 induction mediates luteal regression in the rat" Mol Endocrinol 9(11): 1431-40. Dec. 31, 1995.
Kim, et al., "Arginine, leucine, and glutamine stimulate proliferation of porcine trophectoderm cells through the MTOR-RPS6K-RPS6-EIF4EBP1 signal transduction pathway" Biol Reprod 88(5): 113. Mar. 13, 2013.
Kim, et al., "Select nutrients in the ovine uterine lumen. VII. Effects of arginine, leucine, glutamine, and glucose on trophectoderm cell signaling, proliferation, and migration" Biol Reprod 84(1): 62-9. Sep. 15, 2010.
Kliem, et al., "Expression and localisation of extracellular matrix degrading proteases and their inhibitors during the oestrous cycle and after induced luteolysis in the bovine corpus luteum" Reproduction 134(3): 535-47. Dec. 31, 2007.
Koch, et al., "Proteomic profile of uterine luminal fluid from early pregnant ewes" J Proteome Res 9(8): 3878-85. Jun. 28, 2010.
Krikun, et al., "The expression of the placental anticoagulant protein, annexin V, by villous trophoblasts: immunolocalization and in vitro regulation" Placenta 15(6): 601-12. Dec. 31, 1994.
Krueger, et al., "Acute adrenocorticotropic hormone stimulation of adrenal corticosteroidogenesis. Discovery of a rapidly induced protein" J Biol Chem 258(16): 10159-67. Aug. 25, 1983.
Lavoie, et al., "Mechanisms of insulin-like growth factor I augmentation of follicle-stimulating hormone-induced porcine steroidogenic acute regulatory protein gene promoter activity in granulosa cells" Endocrinology 140(1): 146-53. Dec. 31, 1999.
Lawler, "The functions of thrombospondin-1 and-2" Curr Opin Cell Biol 12(5): 634-40. Dec. 31, 2000.
Leavitt, et al., "Rapid recovery of nuclear estrogen receptor and oxytocin receptor in the ovine uterus following progesterone withdrawal" J Steroid Biochem 22(6): 687-91. Dec. 31, 1985.

(56) References Cited

OTHER PUBLICATIONS

Lee, et al., "Intraluteal prostaglandin biosynthesis and signaling are selectively directed towards PGF2alpha during luteolysis but towards PGE2 during the establishment of pregnancy in sheep" Biol Reprod 87(4): 97. Jun. 27, 2012.
Roberts, et al., "Interferons and the maternal-conceptus dialog in mammals" Seminars in Cell & Developmental Biology 19(2): 170-177. Apr. 30, 2008.
Roberts, et al., "Interferons as hormones of pregnancy" Endocr Rev 13(3): 432-52. Dec. 31, 1992.
Roberts, et al., "Maternal recognition of pregnancy" Biol Reprod 54(2): 294-302. Dec. 31, 1996.
Rocchetti, et al., "Group B streptococci colonization in pregnant women: risk factors and evaluation of the vaginal flora" Arch Gynecol Obstet 283(4): 717-21. Dec. 31, 2011.
Rochebrochard, et al., "Paternal age and maternal age are risk factors for miscarriage; results of a multicentre European study" Hum Reprod 17(6): 1649-56. Dec. 31, 2002.
Romero, et al., "Pregnancy-associated genes contribute to antiluteolytic mechanisms in ovine corpus luteum" Physiol Genomics. Sep. 17, 2013.
Rovere, et al., "The long pentraxin PTX3 binds to apoptotic cells and regulates their clearance by antigen-presenting dendritic cells" Blood 96(13): 4300-6. Dec. 15, 2000.
Rueda, et al., "Recombinant interferon-tau regulates secretion of two bovine endometrial proteins" J.Interferon Res. 13(4): 303-309. Dec. 31, 1993.
Saeed, et al., "Purification of 15-hydroxy prostaglandin dehydrogenase from bovine lung" Biochem Biophys Res Commun 47(1): 96-102. Dec. 31, 1972.
Salio, et al., "Cardioprotective function of the long pentraxin PTX3 in acute myocardial infarction" Circulation 117(8): 1055-64. Dec. 31, 2008.
Samuel, "Antiviral Actions of Interferons" American Society for Microbiology 14(4): 778-809. Oct. 31, 2001.
Sandhoff, et al., "Prostaglandin F2alpha reduces steroidogenic acute regulatory (StAR) protein messenger ribonucleic acid expression in the rat ovary" Endocrine 5(2): 183-90. Oct. 31, 1996.
Sandhoff, et al., "Repression of the rat steroidogenic acute regulatory (StAR) protein gene by PGF2alpha is modulated by the negative transcription factor DAX-1" Endocrine 10(1): 83-91. Feb. 28, 1999.
Sartorius, et al., "Molecular mechanisms of death-receptor-mediated apoptosis" Chembiochem 2(1): 20-9. Dec. 31, 2001.
Sawyer, et al., "Nuclear changes in ovine luteal cells in response to PGF2 alpha" Domest Anim Endocrinol 7(2): 229-37. Dec. 31, 1990.
Schalue-Francis, et al., "Effect of injected bovine interferon-alpha I1 on estrous cycle length and pregnancy success in sheep" J Reprod Fertil 91(1): 347-56. Dec. 31, 1991.
Schmitt, et al., "Uterine cellular changes in 2',5'-oligoadenylate synthetase during the bovine estrous cycle and early pregnancy" Biol Reprod 48(3): 460-6. Dec. 31, 1993.
Schmittgen, et al., "Analyzing real-time PCR data by the comparative C(T) method" Nat Protoc 3(6): 1101-8. Jun. 5, 2008.
Searle, et al., "Improving sensitivity by probabilistically combining results from multiple MS/MS search methodologies" J Proteome Res 7(1): 245-253. Jan. 4, 2008.
Sharma, et al., "Breast cancer cell surface annexin II induces cell migration and neoangiogenesis via tPA dependent plasmin generation" Exp Mol Pathol 88(2): 278-86. Jan. 15, 2010.
Shu, et al. "Immunohistochemical study of annexin V expression in placentae of preeclampsia" Gynecol Obstet Invest 49(1): 17-23. Dec. 31, 2000.
Silva, et al., "Prostaglandin metabolism in the ovine corpus luteum: catabolism of prostaglandin F(2alpha) (PGF(2alpha)) coincides with resistance of the corpus luteum to PGF(2alpha)" Biol Reprod 63(5): 1229-36. Dec. 31, 2000.
Silvia, et al., "Maintenance of the corpus luteum of early pregnancy in the ewe. III. Differences between pregnant and nonpregnant ewes in luteal responsiveness to prostaglandin F2 alpha" J Anim Sci 59(3): 746-53. Dec. 31, 1984.
Silvia, et al., "Maintenance of the corpus luteum of early pregnancy in the ewe. IV. Changes in luteal sensitivity to prostaglandin F2 alpha throughout early pregnancy" J Anim Sci 63(4): 1201-7. Dec. 31, 1986.
Smith, et al., "Control of extracellular matrix remodelling within ovarian tissues: localization and regulation of gene expression of plasminogen activator inhibitor type-1 within the ovine corpus luteum" J Reprod Fertil 110(1): 107-14. Dec. 31, 1997.
Smith, et al., "Mechanisms associated with corpus luteum development" J Anim Sci 72(7): 1857-72. Dec. 31, 1994.
Smith, "Prostanoid biosynthesis and mechanisms of action" Am J Physiol 263(2 Pt 2): F181-91. Dec. 31, 1992.
Smyth, "Linear models and empirical bayes methods for assessing differential expression in microarray experiments" Stat Appl Genet Mol Biol 3: Article3. Dec. 31, 2004.
Song, et al., "Pregnancy and interferon tau regulate RSAD2 and IFIH1 expression in the ovine uterus" Reproduction 133(1): 285-95. Dec. 31, 2007.
Song, et al., "Pregnancy and interferon tau regulate DDX58 and PLSCR1 in the ovine uterus during the peri-implantation period" Reproduction 141(1): 127-38. Dec. 31, 2011.
Spencer, et al., "Temporal and spatial alterations in uterine estrogen receptor and progesterone receptor gene expression during the estrous cycle and early pregnancy in the ewe" Biology of Reproduction 53(6): 1527-1543. Dec. 31, 1995.
Spencer, et al., "Ovine interferon tau suppresses transcription of the estrogen receptor and oxytocin receptor genes in the ovine endometrium" Endocrinology 137(3): 1144-7. Dec. 31, 1996.
Spencer, et al., "Ovine interferon-tau inhibits estrogen receptor up-regulation and estrogen-induced luteolysis in cyclic ewes" Endocrinology 136(11): 4932-44. Dec. 31, 1995.
Spencer, et al., "Conceptus signals for establishment and maintenance of pregnancy" Anim Reprod Sci 82-83: 537-50. Dec. 31, 2004.
Spencer, et al., "Conceptus-derived prostaglandins regulate gene expression in the endometrium prior to pregnancy recognition in ruminants" Reproduction 146(4): 377-87. Dec. 31, 2013.
Spencer, et al., "Intrauterine injection of ovine interferon-tau alters oestrogen receptor and oxytocin receptor expression in the endometrium of cyclic ewes" J Mol Endocrinol 15(2): 203-20. Dec. 31, 1995.
Spencer, et al., "Implantation mechanisms: insights from the sheep" Reproduction 128(6): 657-68. Dec. 31, 2004.
Spencer, et al., "tau-Interferon: pregnancy recognition signal in ruminants" Proc Soc Exp Biol Med 213(3): 215-29. Dec. 31, 1996.
Spencer, et al. "Differential effects of intrauterine and subcutaneous administration of recombinant ovine interferon tau on the endometrium of cyclic ewes" Biol Reprod 61(2): 464-70. Dec. 31, 1999.
Staggs, et al., "Complex induction of bovine uterine proteins by interferon-tau" Biol Reprod 59(2): 293-7. Dec. 31, 1998.
Stein, et al., "Repression of the interleukin-6 promoter by estrogen receptor is mediated by NF-kappa B and C/EBP beta" Mol Cell Biol 15(9): 4971-9. Sep. 30, 1995.
Strandberg, et al., "Economic consequences of different calving intervals" ACTA Agric Scand 39: 407-420. Dec. 31, 1989.
Stocco, et al., "The molecular control of corpus luteum formation, function, and regression" Endocr Rev 28(1): 117-49. Dec. 31, 2007.
Stocco, et al., "A calcium/calmodulin-dependent activation of ERK1/2 mediates JunD phosphorylation and induction of nur77 and 20alpha-hsd genes by prostaglandin F2alpha in ovarian cells" J Biol Chem 277(5): 3293-302. Feb. 1, 2002.
Stocco, "StAR protein and the regulation of steroid hormone biosynthesis" Annu Rev Physiol 63: 193-213. Dec. 31, 2001.
Stocco, et al., "Regulation of the acute production of steroids in steroidogenic cells" Endocr Rev 17(3): 221-44. Dec. 31, 1996.
Sugawara, et al., "Structure of the human steroidogenic acute regulatory protein (StAR) gene: StAR stimulates mitochondrial cholesterol 27-hydroxylase activity" Biochemistry 34(39): 12506-12. Dec. 31, 1995.

(56) References Cited

OTHER PUBLICATIONS

Swanston, et al., "Concentration of prostaglandin F2alpha and steroids in the human corpus luteum" J Endocrinol 73(1): 115-22. Dec. 31, 1977.
Takahashi, et al., "Establishment of a specific radioimmunoassay for bovine interferon tau" Theriogenology 63:1050-1060. Dec. 31, 2005.
Tait, et al., "Placental anticoagulant proteins: isolation and comparative characterization four members of the lipocortin family" Biochemistry 27(17): 6268-76. Dec. 31, 1988.
Lehmann, et al., "Ecdysteroid receptors of the blowfly Calliphora vicina. Characterization of binding to nonspecific DNA" Eur J Biochem 181(3): 577-82. Dec. 31, 1989.
Lehoux, et al., "The acute and chronic effects of adrenocorticotropin on the levels of messenger ribonucleic acid and protein of steroidogenic enzymes in rat adrenal in vivo" Endocrinology 139(9): 3913-22. Dec. 31, 1998.
Lejeune, et al., "Time-course effects of human recombinant luteinizing hormone on porcine Leydig cell specific differentiated functions" Mol Cell Endocrinol 144(1-2): 59-69. Dec. 31, 1998.
Leslie, et al., "Evidence for the presence of a prostaglandin E 2-9-keto reductase in rat organs" Biochem Biophys Res Commun 52(3): 717-24. Dec. 31, 1973.
Lestavel, et al., "Lipoprotein receptors" Cell Mol Biol (Noisy-le-grand) 40(4): 461-81. Dec. 31, 1994.
Levasseur, "Utero-ovarian relationships in placental mammals: role of uterus and embryo in the regulation of progesterone secretion by the corpus luteum. A review" Reprod Nutr Dev 23(5): 793-816. Dec. 31, 1983.
Li, et al., "Interferon-tau and interferon-alpha interact with the same receptors in bovine endometrium. Use of a readily iodinatable form of recombinant interferon-tau for binding studies" J Biol Chem 269(18): 13544-50. May 6, 1994.
Lin, et al., "Role of steroidogenic acute regulatory protein in adrenal and gonadal steroidogenesis" Science 267(5205): 1828-31. Mar. 24, 1995.
Lin, et al., "Interferon-gamma inhibits the steroidogenic acute regulatory protein messenger ribonucleic acid expression and protein levels in primary cultures of rat Leydig cells" Endocrinology 139(5): 2217-22. Dec. 31, 1998.
Lin, et al., "Upregulation of human chorionic gonadotrophin-induced steroidogenic acute regulatory protein by insulin-like growth factor-I in rat Leydig cells" Endocrine 8(1): 73-8. Feb. 28, 1998.
Liu, et al., "A model for random sampling and estimation of relative protein abundance in shotgun proteomics" Anal Chem 76(14): 4193-4201. Dec. 31, 2004.
Liu, et al., "Down-regulation of S100A11, a calcium-binding protein, in human endometrium may cause reproductive failure" J Clin Endocrinol Metab 97(10): 3672-83. Oct. 31, 2012.
Liu, et al., "Heat shock-induced inhibition of acute steroidogenesis in MA-10 cells is associated with inhibition of the synthesis of the steroidogenic acute regulatory protein" Endocrinology 138(7): 2722-8. Dec. 31, 1997.
Livak, et al., "Analysis of relative gene expression data using real-time quantitative PCR and the 2(-Delta Delta C(T)) Method" Methods 25(4): 402-8. Dec. 31, 2001.
Loeb, et al., "The interferon-inducible 15-kDa ubiquitin homolog conjugates to intracellular proteins" J Biol Chem 267(11): 7806-13. Apr. 15, 1992.
Luo, et al., "Leydig cell protein synthesis and steroidogenesis in response to acute stimulation by luteinizing hormone in rats" Biol Reprod 59(2): 263-70. Dec. 31, 1998.
MacLean, et al., "Atypical Kunitz-type serine proteinase inhibitors produced by the ruminant placenta" Biol Reprod 71(2): 455-63. Apr. 7, 2004.
Magness, et al., "Effect of chronic ipsilateral or contralateral intrauterine infusion of prostaglandin E2 (PGE2) on luteal function of unilaterally ovariectomized ewes" Prostaglandins Med 6(4): 389-401. Dec. 31, 1981.

Mapletoft, et al., "The ovarian artery as the final component of the local luteotropic pathway between a gravid uterine horn and ovary in ewes" Biol Reprod 15(3): 414-21. Dec. 31, 1976.
Margosio, et al., "Thrombospondin 1 as a scavenger for matrix-associated fibroblast growth factor 2" Blood 102(13): 4399-406. Dec. 15, 2003.
Maroni, et al., "TGFB1 disrupts the angiogenic potential of microvascular endothelial cells of the corpus luteum" J Cell Sci 124(Pt 14): 2501-10. Dec. 31, 2011.
Masferrer, et al., "In vivo glucocorticoids regulate cyclooxygenase-2 but not cyclooxygenase-1 in peritoneal macrophages" J Pharmacal Exp Ther 270(3): 1340-4. Dec. 31, 1994.
Mauduit, et al., "Tumor necrosis factor-alpha inhibits leydig cell steroidogenesis through a decrease in steroidogenic acute regulatory protein expression" Endocrinology 139(6): 2863-8. Dec. 31, 1998.
McCracken, et al., "Prostaglandin F 2 identified as a luteolytic hormone in sheep" Nat New Biol 238(83): 129-34. Aug. 2, 1972.
McCracken, et al., "Luteolysis: A Neuroendocrine-Mediated Event" Physiological Reviews 79(2): 263-323. Apr. 30, 1999.
McCracken, et al., "Corpus luteum regression induced by prostagland in F2-alpha" J Clin Endocrinol Metab 30(4): 544-6. Apr. 30, 1970.
McLaughlin, et al., "Thrombin modulates the expression of a set of genes including thrombospondin-1 in human microvascular endothelial cells" J Biol Chem 280(23): 22172-80. Apr. 7, 2005.
McPherson, et al., "Localization of stress protein-70 in ovine corpora lutea during prostaglandin-induced luteolysis" Prostaglandins 46(5): 433-40. Dec. 31, 1993.
McWaters, et al., "Characterisation of monoclonal antibodies to ovine interleukin-6 and the development of a sensitive capture ELISA" Vet Immunol Immunopathol 73(2): 155-65. Dec. 31, 2000.
Meadows, et al., "A spreadsheet-based model demonstrating the nonuniform economic effects of varying reproductive performance in Ohio dairy herds" J Dairy Sci 88: 1244-1254. Dec. 31, 2005.
Menkhorst, et al., "Decidual-secreted factors alter invasive trophoblast membrane and secreted proteins implying a role for decidual cell regulation of placentation" PLoS One 7(2): e31418. Feb. 16, 2012.
Metwally, et al., "Does high body mass index increase the risk of miscarriage after spontaneous and assisted conception? A meta-analysis of the evidence" Fertil Steril 90(3): 714-26. Sep. 30, 2008.
Meyer, et al., "Treatment with recombinant bovine interferon-tau in utero attenuates secretion of prostaglandin F from cultured endometrial epithelial cells" J Dairy Sci 79(8): 1375-84. Dec. 31, 1996.
Milvae, et al., "Prostacyclin, prostaglandin F2 alpha and progesterone production by bovine luteal cells during the estrous cycle" Biol Reprod 29(5): 1063-8. Dec. 31, 1983.
Mirando, et al., "Stimulation of 2',5'-oligoadenylate synthetase activity in sheep endometrium during pregnancy, by intrauterine infusion of ovine trophoblast protein-1, and by intramuscular administration of recombinant bovine interferon-alpha I1" J Reprod Fertil 93(2): 599-607. Dec. 31, 1991.
Mirochnik, et al., "Thrombospondin and apoptosis: molecular mechanisms and use for design of complementation treatments" Curr Drug Targets 9(10): 851-62. Oct. 31, 2008.
Mondal, et al., "Deciphering the luteal transcriptome: potential mechanisms mediating stage-specific luteolytic response of the corpus luteum to prostaglandin F(2)alpha" Physiol Genomics 43(8): 447-56. Feb. 15, 2011.
Moor, et al., "Influence of the Embryo and Uterus on Luteal Function in the Sheep" Nature 201: 522-3. Feb. 1, 1964.
Moor, et al., "The corpus luteum of the sheep: functional relationship between the embryo and the corpus luteum" J Endocrinol 34(2): 233-9. Dec. 31, 1966.
Moor, et al., "Local uterine mechanisms affecting luteal function in the sheep" J Reprod Fertil 11(2): 307-10. Dec. 31, 1966.
Moore, et al., "Evidence for the pulsatile release of PGF-2 alpha inducing the release of ovarian oxytocin during luteolysis in the ewe" J Reprod Fertil 76(1): 159-66. Dec. 31, 1986.
Mosser, et al., "Sub-domain structure of lipid-bound annexin-V resolved by electron image analysis" J Mol Biol 217(2): 241-5. Dec. 31, 1991.

(56) References Cited

OTHER PUBLICATIONS

Muller-Newen, et al., "Soluble IL-6 receptor potentiates the antagonistic activity of soluble gp130 on IL-6 responses" J Immunol 161(11): 6347-55. Dec. 31, 1998.
Munoz, et al., "Proteome of the early embryo-maternal dialogue in the cattle uterus." J Proteome Res 11(2): 751-66. Dec. 9, 2011.
Murphy, "Models of luteinization" Biol Reprod 63(1): 2-11. Dec. 31, 2000.
Nackley, et al., "Repression of the steroidogenic acute regulatory gene by the multifunctional transcription factor Yin Yang 1" Endocrinology 143(3): 1085-96. Dec. 31, 2002.
Naivar, et al., "Secretion of bovine uterine proteins in response to type I interferons" Biol Reprod 52(4): 848-54. Dec. 31, 1995.
Narasimhan, et al., "Conjugation of the 15-kDa interferon-induced ubiquitin homolog is distinct from that of ubiquitin" J Biol Chem 271(1): 324-30. Jan. 5, 1996.
Nett, et al., "Effects of prostaglandins on the ovine corpus luteum: blood flow, secretion of progesterone and morphology" Biol Reprod 15(1): 66-78. Dec. 31, 1976.
Nickel, "The mystery of nonclassical protein secretion. A current view on cargo proteins and potential export routes" Eur J Biochem 270(10): 2109-19. Dec. 31, 2003.
Nigro, et al., "Role of the infections in recurrent spontaneous abortion" J Matern Fetal Neonatal Med 24(8): 983-9. Aug. 31, 2011.
Nishikawa, et al., "Regulation of expression of the steroidogenic acute regulatory (StAR) protein by ACTH in bovine adrenal fasciculata cells" Biochem Biophys Res Commun 223(1): 12-8. Dec. 31, 1996.
Niswender, et al., "Influence of the site of conjugation on the specificity of antibodies to progesterone" Steroids 22(3):413-24. May 21, 1973.
Niswender, et al., "Judge, jury and executioner: the auto-regulation of luteal function" Soc Reprod Fertil Suppl 64: 191-206. Dec. 31, 2007.
Niswender, et al., "Mechanisms controlling the function and life span of the corpus luteum" Physiol Rev 80(1): 1-29. Jan. 31, 2000.
Niswender, et al., "Flow of blood to the ovaries of ewes throughout the estrous cycle" Biol Reprod 13(4): 381-8. Dec. 31, 1975.
Nitta, et al., "Possible involvement of IFNT in lymphangiogenesis in the corpus luteum during the maternal recognition period in the cow" Reproduction 142(6): 879-92. Dec. 31, 2011.
Nor, et al. "Thrombospondin-1 induces endothelial cell apoptosis and inhibits angiogenesis by activating the caspase death pathway" J Vasc Res 37(3): 209-18. May 31, 2000.
O'Shea, et al., "The small luteal cell of the sheep" J Anat 128(Pt 2): 239-51. Dec. 31, 1979.
Oehme, et al., "Agonists of an ecdysone-inducible mammalian expression system inhibit Fas Ligand- and TRAIL-induced apoptosis in the human colon carcinoma cell line RKO" Cell Death Differ 13(2): 189-201. Aug. 5, 2005.
Okuyama, "Revisiting the molecular structure of collagen" Connect Tissue Res 49(5): 299-310. Dec. 31, 2008.
Oliveira, et al., "Expression of interferon (IFN)-stimulated genes in extrauterine tissues during early pregnancy in sheep is the consequence of endocrine IFN-tau release from the uterine vein" Endocrinology 149: 1252-1259. Dec. 6, 2007.
Olofsson, et al., "Auto/paracrine role of prostaglandins in corpus luteum function" Mol Cell Endocrinol 100(1-2): 87-91. Dec. 31, 1994.
Olofsson, et al., "Synthesis of prostaglandin F2 alpha, E2 and prostacyclin in isolated corpora lutea of adult pseudopregnant rats throughout the luteal life-span" Prostaglandins Leukot Essent Fatty Acids 46(2): 151-61. Dec. 31, 1992.
Osaki, et al., "PI3K-Akt pathway: its functions and alterations in human cancer" Apoptosis 9(6): 667-76. Dec. 31, 2004.
Otani, et al., "The vascular endothelial growth factor/fms-like tyrosine kinase system in human ovary during the menstrual cycle and early pregnancy" J Clin Endocrinol Metab 84(10): 3845-51. Dec. 31, 1999.
Ott, et al., "Effects of the estrous cycle and early pregnancy on uterine expression of Mx protein in sheep (*Ovis aries*)" Biol Reprod 59(4): 784-94. Dec. 31, 1998.
Palade, "Intracellular aspects of the process of protein synthesis" Science 189(4200): 347-58. Aug. 1, 1975.
Papadopoulos, et al., "Peripheral benzodiazepine receptor in cholesterol transport and steroidogenesis" Steroids 62(1): 21-8. Dec. 31, 1997.
Papadopoulos, et al., "Targeted disruption of the peripheral-type benzodiazepine receptor gene inhibits steroidogenesis in the R2C Leydig tumor cell line" J Biol Chem 272(51): 32129-35. Dec. 19, 1997.
Papadopoulos, et al., "Role of the peripheral-type benzodiazepine receptor and the polypeptide diazepam binding inhibitor in steroidogenesis" J Steroid Biochem Mol Biol 53(1-6): 103-10. Dec. 31, 1995.
Paradela, et al., "Proteomic analysis of apical microvillous membranes of syncytiotrophoblast cells reveals a high degree of similarity with lipid rafts" J Proteome Res 4(6): 2435-41. Nov. 18, 2005.
Pate, "Regulation of prostaglandin synthesis by progesterone in the bovine corpus luteum" Prostaglandins 36(3): 303-15. Sep. 30, 1988.
Patek, et al., "Prostaglandin F and progesterone secretion by porcine endometrium and corpus luteum in vitro" Prostaglandins 12(1): 97-111. Jul. 31, 1976.
Perretti, et al., "Annexin 1 and the biology of the neutrophil" J Leukoc Biol 76(1): 25-9. Jul. 31, 2004.
Perretti, et al., "Annexin 1: an endogenous anti-inflammatory protein" News Physiol Sci 18: 60-4. Dec. 31, 2003.
Perry, et al., "Cloning of interferon-stimulated gene 17: the promoter and nuclear proteins that regulate transcription" Mol Endocrinol 13(7): 1197-206. Dec. 31, 1999.
Pescador, et al., "Follicle-stimulating hormone and intracellular second messengers regulate steroidogenic acute regulatory protein messenger ribonucleic acid in luteinized porcine granulosa cells" Biol Reprod 57(3): 660-8. Dec. 31, 1997.
Peterson, et al., "Jugular levels of 13, 14-dihydro-15-keto-prostaglandin F and progesterone around luteolysis and early pregnancy in the ewe" Prostaglandins 12(4): 551-8. Oct. 31, 1976.
Pitcher, et al., "Decision analysis and economic evaluation of the use of the rapid milk progesterone assay for early detection of pregnancy status of cows" J Am Vet Med Assoc 197: 1586-1590. Dec. 15, 1990.
Piper, et al., "Inactivation of prostaglandins by the lungs" Nature 225(5233): 600-4. Feb. 14, 1970.
Plaizier, et al., "Estimation of economic values of indices for reproductive performance in dairy herds using computer simulation" J Dairy Sci 80: 2775-2783. Dec. 31, 1997.
Plante, et al., "Purification of bovine trophoblast protein-1 complex and quantification of its microheterogeneous variants as affected by culture conditions" Journal of reproductive immunology 18: 271-291. Dec. 31, 1990.
Pletneva, et al., "Interferon-inducible Mx gene expression in cotton rats: cloning, characterization, and expression during influenza viral infection" J Interferon Cytokine Res 26(12): 914-21. Dec. 31, 2006.
Pon, et al., "Acute cAMP stimulation in Leydig cells: rapid accumulation of a protein similar to that detected in adrenal cortex and corpus luteum" Endocr Res 12(4): 429-46. Dec. 31, 1986.
Pon, et al., "Acute ACTH regulation of adrenal corticosteroid biosynthesis. Rapid accumulation of a phosphoprotein" J Biol Chem 261(28): 13309-16. Oct. 5, 1986.
Pon, et al., "Acute stimulation of steroidogenesis in corpus luteum and adrenal cortex by peptide hormones. Rapid induction of a similar protein in both tissues" J Biol Chem 261(14): 6594-9. May 15, 1986.
Pon, et al., "Acute stimulation of corpus luteum cells by gonadotrophin or adenosine 3',5'-monophosphate causes accumulation of a phosphoprotein concurrent with acceleration of steroid synthesis" Endocrinology 123(4): 1942-8. Dec. 31, 1988.
Pratt, et al., "Antiluteolytic effect of the conceptus and of PGE2 in ewes" J Anim Sci 45(4): 784-91. Dec. 31, 1977.
Pru, et al., "Signaling mechanisms in tumor necrosis factor alpha-induced death of microvascular endothelial cells of the corpus luteum" Reprod Biol Endocrinol 1: 17. Feb. 11, 2003.

(56) References Cited

OTHER PUBLICATIONS

Pru, et al., "Interferon-tau suppresses prostaglandin F2alpha secretion independently of the mitogen-activated protein kinase and nuclear factor kappa B pathways" Biol Reprod 64(3): 965-73. Dec. 31, 2001.
Rand, "The pathogenic role of annexin-V in the antiphospholipid syndrome" Curr Rheumatol Rep 2(3): 246-51. Dec. 31, 2000.
Ravizza, et al., "Dynamic induction of the long pentraxin PTX3 in the CNS after limbic seizures: evidence for a protective role in seizure-induced neurodegeneration" Neuroscience 105(1): 43-53. Dec. 31, 2001.
Rege, et al., "Thrombospondin-1-induced apoptosis of brain microvascular endothelial cells can be mediated by TNF-R1" J Cell Physiol 218(1): 94-103. Jan. 31, 2009.
Rempel, et al., "Isolation and sequence of an interferon-tau-inducible, pregnancy- and bovine interferon-stimulated gene product 15 (ISG15)-specific, bovine ubiquitin-activating E1-like (UBE1L) enzyme" Biol Reprod 72(2): 365-72. Sep. 22, 2004.
Ren, et al., "Regulation of tumor angiogenesis by thrombospondin-1" Biochim Biophys Acta 1765(2): 178-88. Dec. 21, 2005.
Rexroad, et al., "Prostaglandin F2 alpha and progesterone release in vitro by ovine luteal tissue during induced luteolysis" Adv Exp Med Biol 112: 639-44. Dec. 31, 1979.
Reynolds, et al., "Effect of PGE1 on PGF2 alpha-induced luteolysis in nonbred ewes" Prostaglandins 21(6): 957-72. Jun. 30, 1981.
Rintala-Dempsey, "S100-annexin complexes—structural insights" FEBS J 275(20): 4956-66. Dec. 31, 2008.
Roberts, "Conceptus interferons and maternal recognition of pregnancy" Biol Reprod 40(3): 449-52. Dec. 31, 1989.
Taniguchi, et al., "The interferon-alpha/beta system in antiviral responses: a multimodal machinery of gene regulation by the IRF family of transcription factors" Curr Opin Immunol 14(1): 111-6. Dec. 31, 2002.
Teixeira, et al., "Bovine granulocyte chemotactic protein-2 is secreted by the endometrium in response to interferon-tau (IFN-tau)" Endocrine 6(1): 31-7. Feb. 28, 1997.
Telleria, et al., "The expression of interleukin-6 in the pregnant rat corpus luteum and its regulation by progesterone and glucocorticoid" Endocrinology 139(8): 3597-605. Dec. 31, 1998.
Temmerman, et al., "The role of maternal syphilis, gonorrhoea and HIV-1 infections in spontaneous abortion" Int J STD AIDS 3(6): 418-22. Dec. 31, 1992.
Toyokawa, et al., "Cellular localization and function of the antiviral protein, ovine Mx1 (oMx1): I. Ovine Mx1 is secreted by endometrial epithelial cells via an 'unconventional' secretory pathway" Am J Reprod Immunol 57(1): 13-22. Dec. 31, 2007.
Toyokawa, et al., "Cellular localization and function of the antiviral protein, ovine Mx1 (oMx1): II. The oMx1 protein is a regulator of secretion in an ovine glandular epithelial cell line" Am J Reprod Immunol 57(1): 23-33. Dec. 31, 2007.
Tuckey, et al., "Cholesterol side-chain cleavage by mitochondria from the human placenta. Studies using hydroxycholesterols as substrates" J Steroid Biochem Mol Biol 42(8): 883-90. Dec. 31, 1992.
Tuckey, et al., "Pregnenolone synthesis from cholesterol and hydroxycholesterols by mitochondria from ovaries following the stimulation of immature rats with pregnant mare's serum gonadotropin and human choriogonadotropin" Eur J Biochem 186(1-2): 255-9. Dec. 31, 1989.
Vinatier, et al., "Apoptosis: a programmed cell death involved in ovarian and uterine physiology" Eur J Obstet Gynecol Reprod Biol 67(2): 85-102. Dec. 31, 1996.
Voges, et al., "Three-dimensional structure of membrane-bound annexin V. A correlative electron microscopy-X-ray crystallography study" J Mol Biol 238(2): 199-213. Dec. 31, 1994.
Vorsanova, et al., "Evidence for high frequency of chromosomal mosaicism in spontaneous abortions revealed by interphase FISH analysis" J Histochem Cytochem 53(3): 375-80. Dec. 31, 2005.

Wang, et al., "Annexin V is critical in the maintenance of murine placental integrity" Am J Obstet Gynecol 180(4): 1008-16. Dec. 31, 1999.
Watson, et al., "Secretion of prostaglandins and progesterone by cells from corpora lutea of mares" J Reprod Fertil 88(1): 223-9. Dec. 31, 1990.
Watson, et al., "Prostaglandin E-2-9-ketoreductase in ovarian tissues" J Reprod Fertil 57(2): 489-96. Dec. 31, 1979.
Wiltbank, et al., "Steroidogenic enzyme activity after acute activation of protein kinase (PK) A and PKC in ovine small and large luteal cells" Mol Cell Endocrinol 97(1-2): 1-7. Dec. 31, 1993.
Wiltbank, et al., "Hormonal regulation of free intracellular calcium concentrations in small and large ovine luteal cells" Biol Reprod 41(4): 771-8. Dec. 31, 1989.
Wiltbank, et al., "Regulation of intraluteal production of prostaglandins" Reprod Biol Endocrinol 1: 91. Nov. 10, 2003.
Yamada, et al., "The dynamic expression of extracellular matrix in the bovine endometrium at implantation" J Vet Med Sci 64(3): 207-14. Dec. 31, 2002.
Yan, et al., "Characterization of phosphoproteins in gastric cancer secretome" OMICS 15(1-2): 83-90. Dec. 31, 2011.
Yankey, et al., "Expression of the antiviral protein Mx in peripheral blood mononuclear cells of pregnant and bred, non-pregnant ewes" J Endocrinol 170(2): R7-11. Dec. 31, 2001.
Yarmola, et al., "How depolymerization can promote polymerization: the case of actin and profilin" Bioessays 31(11): 1150-60. Dec. 31, 2009.
Zalman, et al., "Regulation of angiogenesis-related prostaglandin f2alpha-induced genes in the bovine corpus luteum" Biol Reprod 86(3): 92. Dec. 14, 2011.
Zarco, et al., "Modification of prostaglandin F-2 alpha synthesis and release in the ewe during the initial establishment of pregnancy" J Reprod Fertil 83(2): 527-36. Dec. 31, 1988.
Zarco, et al., "Release of prostaglandin F-2 alpha and the timing of events associated with luteolysis in ewes with oestrous cycles of different lengths" J Reprod Fertil 83(2): 517-26. Dec. 31, 1988.
Zelinski, et al., "Characterization of plasma membrane lipids and luteinizing hormone receptors of ovine corpora lutea during luteolysis and early pregnancy" Biol Reprod 38(4): 768-79. Dec. 31, 1988.
Zeth, et al., "Porins in prokaryotes and eukaryotes: common themes and variations" Biochem J 431(1): 13-22. Dec. 31, 2010.
Zheng, et al., "Tyrosine 23 phosphorylation-dependent cell-surface localization of annexin A2 is required for invasion and metastases of pancreatic cancer" PLoS One 6(4): e19390. Apr. 30, 2011.
Zhu, et al., "Transforming growth factor-1 promotes the transcriptional activation of plasminogen activator inhibitor type 1 in carcinoma-associated fibroblasts" Mol Med Rep 6(5): 1001-5. Dec. 31, 2012.
Alberta, et al., "Mitochondrial localization of a phosphoprotein that rapidly accumulates in adrenal cortex cells exposed to adrenocorticotropic hormone or to cAMP" J Biol Chem 264(4): 2368-72. Feb. 5, 1989.
Alila, et al., "Origin of different cell types in the bovine corpus luteum as characterized by specific monoclonal antibodies" Biol Reprod 31(5): 1015-25. Dec. 31, 1984.
Allison, et al., "Ovine uterine gland knock-out model: effects of gland ablation on the estrous cycle" Biol Reprod 62(2): 448-56. Dec. 31, 2000.
Anthony, et al., "Synthesis and processing of ovine trophoblast protein-1 and bovine trophoblast protein-1, conceptus secretory proteins involved in the maternal recognition of pregnancy" Endocrinology 123: 1274-1280 Dec. 31, 1988.
Antoniazzi, et al., "Endocrine delivery of interferon tau protects the corpus luteum from prostaglandin F2 alpha-induced luteolysis in ewes" Biol Reprod 88(6): 144. Apr. 24, 2013.
Arakane, et al., "Phosphorylation of steroidogenic acute regulatory protein (StAR) modulates its steroidogenic activity" J Biol Chem 272(51): 32656-62. Dec. 19, 1997.
Armstrong, et al., "Thrombospondin 2 inhibits microvascular endothelial cell proliferation by a caspase-independent mechanism" Mol Biol Cell 13(6): 1893-905. Jun. 30, 2002.

(56) References Cited

OTHER PUBLICATIONS

Arosh, et al., "Effect of interferon-tau on prostaglandin biosynthesis, transport, and signaling at the time of maternal recognition of pregnancy in cattle: evidence of polycrine actions of prostaglandin E2" Endocrinology 145(11): 5280-93. Dec. 31, 2004.

Arvisais, et al., "Prostaglandin F2alpha represses IGF-I-stimulated IRS1/phosphatidylinositol-3-kinase/AKT signaling in the corpus luteum: role of ERK and P70 ribosomal S6 kinase" Mol Endocrinol 24(3): 632-43. Feb. 16, 2010.

Ashburner, et al., "Gene ontology: tool for the unification of biology. The Gene Ontology Consortium" Nature Genetics 25(1): 25-9. May 31, 2000.

Ashworth, et al., "Changes in ovine conceptus and endometrial function following asynchronous embryo transfer or administration of progesterone" Biol Reprod 40(2): 425-33. Dec. 31, 1989.

Austin, et al., "Interferon-stimulated gene-15 (Isg15) expression is up-regulated in the mouse uterus in response to the implanting conceptus" Endocrinology 144(7): 3107-13. Dec. 31, 2003.

Austin, et al., "Localization of ISG15 and conjugated proteins in bovine endometrium using immunohistochemistry and electron microscopy" Endocrinology 145(2): 967-75. Dec. 31, 2004.

Austin, et al., "Ubiquitin cross-reactive protein is released by the bovine uterus in response to interferon during early pregnancy" Biol Reprod 54(3): 600-6. Dec. 31, 1996.

Babiychuk, et al., "Annexins in cell membrane dynamics: Ca(2+)-regulated association of lipid microdomains" J Cell Biol 150(5): 1113-24. Sep. 5, 2000.

Balasubramanian, et al., "Regulation of porcine granulosa cell steroidogenic acute regulatory protein (StAR) by insulin-like growth factor I: synergism with follicle-stimulating hormone or protein kinase A agonist" Endocrinology 138(1): 433-9. Dec. 31, 1997.

Banu, et al., "Expression of prostaglandin transporter in the bovine uterus and fetal membranes during pregnancy" Biol Reprod 73(2): 230-6. Apr. 6, 2005.

Barcikowski, et al., "The effect of endogenous and exogenous estradiol-17beta on the release of prostaglandin F2alpha from the ovine uterus" Endocrinology 95(5): 1340-9. Dec. 31, 1974.

Bauersachs, et al., "Comparison of the effects of early pregnancy with human interferon, alpha 2 (IFNA2), on gene expression in bovine endometrium" Biol Reprod 86(2): 46. Oct. 27, 2011.

Bauersachs, et al., "Immune aspects of embryo-maternal cross-talk in the bovine uterus" J Reprod Immunol 97(1): 20-6. Dec. 31, 2013.

Bazer, et al., "Select nutrients, progesterone, and interferon tau affect conceptus metabolism and development" Ann N Y Acad Sci 1271: 88-96. Dec. 31, 2012.

Bazer, et al., "Biochemical aspects of conceptus—endometrial interactions" J Exp Zool 228(2): 373-83. Dec. 31, 1983.

Bazer, et al., "Role of conceptus secretory products in establishment of pregnancy" Journal of reproduction and fertility 76: 841-850. Dec. 31, 1986.

Bazer, et al., "Novel pathways for implantation and establishment and maintenance of pregnancy in mammals" Mol Hum Reprod 16(3): 135-52. Oct. 30, 2009.

Bebington, et al. "Ubiquitin cross-reactive protein gene expression is increased in decidualized endometrial stromal cells at the initiation of pregnancy" Mol Hum Reprod 5(10): 966-72. Dec. 31, 1999.

Bekisz, et al., "Human interferons alpha, beta and omega" Growth Factors 22(4): 243-51. Dec. 31, 2004.

Berg, et al., "Embryo loss in cattle between Days 7 and 16 of pregnancy" Theriogenology 73(2): 250-60. Dec. 31, 2010.

Berisha, et al., "Expression and tissue concentration of vascular endothelial growth factor, its receptors, and localization in the bovine corpus luteum during estrous cycle and pregnancy" Biol Reprod 63(4): 1106-14. Dec. 31, 2000.

Binelli, et al., "Interferon-tau modulates phorbol ester-induced production of prostaglandin and expression of cyclooxygenase-2 and phospholipase-A(2) from bovine endometrial cells" Biol Reprod 63(2): 417-24. Dec. 31, 2000.

Binelli, et al., "Bovine interferon-tau stimulates the Janus kinase-signal transducer and activator of transcription pathway in bovine endometrial epithelial cells" Biol Reprod 64(2): 654-65. Dec. 31, 2001.

Bittman, et al., "Nightly duration of pineal melatonin secretion determines the reproductive response to inhibitory day length in the ewe" Biol Reprod 30(3): 585-93. Dec. 31, 1984.

Black, et al., "The mitochondrial environment is required for activity of the cholesterol side-chain cleavage enzyme, cytochrome P450scc" Proc Natl Acad Sci U S A 91(15): 7247-51. Jul. 31, 1994.

Blohm, et al., "A prospective longitudinal population-based study of clinical miscarriage in an urban Swedish population" BJOG 115(2): 176-82; discussion 183. Dec. 31, 2008.

Bogan, et al., "Contitutive steroidogenesis in ovine large luteal cells may be mediated by tonically active protein kinase A" Biol Reprod 77(2): 209-16. Apr. 4, 2007.

Borner, "The Bcl-2 protein family: sensors and checkpoints for life-or-death decisions" Mol Immunol 39(11): 615-47. Dec. 31, 2003.

Bott, et al., "Uterine vein infusion of interferon tau (IFNT) extends luteal life span in ewes" Biology of reproduction 82: 725-735. Dec. 31. 2009.

Braunschweig, et al., "Human pentraxin 3 binds to the complement regulator c4b-binding protein" PLoS One 6(8): e23991. Aug. 22, 2011.

Bremer, "Carnitine—metabolism and functions" Physiol Rev 63(4): 1420-80. Oct. 31, 1983.

Bromer, et al., "Assessment of embryo viability in assisted reproductive technology: shortcomings of current approaches and the emerging role of metabolomics" Curr Opin Obstet Gynecol 20(3): 234-41. Dec. 31, 2008.

Budnik, et al., "Inhibitory effects of TNF alpha on mouse tumor Leydig cells: possible role of ceramide in the mechanism of action" Mol Cell Endocrinol 150(1-2): 39-46. Dec. 31, 1999.

Caffrey, et al., "Activity of 3beta-hydroxy-delta5-steroid dehydrogenase/delta5-delta4-isomerase in the ovine corpus luteum" Biol Reprod 20(2): 279-87. Dec. 31, 1979.

Cardinali, et al., "Cellular and molecular mechanisms controlling melatonin release by mammalian pineal glands" Cell Mol Neurobiol 7(4): 323-37. Dec. 31, 1987.

Chapman, et al., "Evidence for a role of the adenosine 5'-triphosphate-binding cassette transporter A1 in the externalization of annexin I from pituitary folliculo-stellate cells" Endocrinology 144(3): 1062-73. Dec. 31, 2003.

Charleston, et al., "An interferon-induced Mx protein: cDNA sequence and high-level expression in the endometrium of pregnant sheep" Gene 137(2): 327-31. Dec. 31, 1993.

Chegini, et al., "Cellular distribution and cycle phase dependency of gonadotropin and eicosanoid binding sites in bovine corpora lutea" Biol Reprod 45(3): 506-13. Dec. 31, 1991.

Chen, et al., "Expression of the steroidogenic acute regulatory protein and luteinizing hormone receptor and their regulation by tumor necrosis factor alpha in rat corpora lutea" Biol Reprod 60(2): 419-27. Dec. 31, 1999.

Christenson, et al., "Research resource: preovulatory LH surge effects on follicular theca and granulosa transcriptomes" Mol Endocrinol 27(7): 1153-71. Jul. 31, 2013.

Chung, et al., "Hormone and prostaglandin F2 alpha regulation of messenger ribonucleic acid encoding steroidogenic acute regulatory protein in human corpora lutea" Endocrine 8(2): 153-60. Apr. 30, 1998.

Clark, et al., "The purification, cloning, and expression of a novel luteinizing hormone-induced mitochondrial protein in MA-10 mouse Leydig tumor cells. Characterization of the steroidogenic acute regulatory protein (StAR)" J Biol Chem 269(45): 28314-22. Nov. 11, 1994.

Cohen, et al., "Interleukin 6 induces the expression of vascular endothelial growth factor" J Biol Chem 271(2): 736-41. Jan. 12, 1996.

Guillomot, M., et al., "Characterization of Conceptus-Produced Goat Interferon and Analysis of its Temporal and cellular Distribution During Early Pregnancy" Journal of Reproduction and Fertility (1998) 112, pp. 149-156.

(56) References Cited

OTHER PUBLICATIONS

Martal, J.L., et al., "IFN-tau: A Novel Subtype I IFN1. Structured Characteristics, Non-Ubiquitous Expression, Structure-Function Relationships, a Pregnancy Hormonal Embryonic Signal and Cross-Species Therapeutic Potentialities", Biochimie (1998) 80, pp. 755-777.

Romero, Jared J., et al., "Temporal Release, Paracrine and Endocrine Actions of Ovine Conceptus-Derived Interferon-Tau During Early Pregnancy", Biology of Reproduction (2015) 93(6): 146, pp. 1-10.

* cited by examiner

| Peptide Sequence | Parent Ion (M/Z) | Daughter Ions (M/Z) |
|---|---|---|
| DFGLPQEM(+16) VEGNQLQK | 925.53 | 1417.01 |
| DFGLPQEM(+16) VEGNQLQK | 925.53 | 1320.51 |
| DFGLPQEM(+16) VEGNQLQK | 925.53 | 1192.6 |
| DFGLPQEM(+16) VEGNQLQK | 925.53 | 1062.91 |
| DFGLPQEM(+16) VEGNQLQK | 925.53 | 709.14 |
| DFGLPQEM(+16) VEGNQLQK | 925.53 | 516.21 |

EARLY DETERMINATION OF PREGNANCY STATUS IN RUMINANTS

CROSS-REFERENCE TO RELATED APPLICATIONS

This application claims priority under 35 U.S.C. § 119 of a provisional application Ser. No. 61/895,887 filed Oct. 25, 2013, which is hereby incorporated by reference in its entirety.

GRANT REFERENCE

This invention was made, in part, with government support under Grant Number 2011-67015-20067 from USDA National Institute of Food and Agriculture. The Government has certain rights in the invention.

INCORPORATION OF SEQUENCE LISTING

The present application is being filed along with a Sequence Listing in electronic format. The Sequence Listing is provided as a file entitled P11221US01_SEQ LIST.txt, created Oct. 24, 2014, which is 51 Kb in size. The information in the electronic format of the sequence listing is incorporated herein by reference in its entirety.

FIELD OF THE INVENTION

The present invention relates to detection schemes for ascertaining whether an animal is pregnant. More particularly, the present invention relates to interferon-tau (IFNT) and/or antibodies specific for IFNT, and methods of the present invention detect the presence or absence of IFNT in samples obtained from animals as an early indicator of pregnancy status.

BACKGROUND OF THE INVENTION

Agricultural livestock operations require reliable, accurate systems for detecting pregnancy in order to optimize offspring crop percent and heavy weaning weights. Cows and sheep producing offspring every 12 months and calving or ewing early in the season give the best performance. To boost the efficiency of breeding operations, it is necessary to identify non-pregnant animals.

Identification of livestock that are not pregnant as early as possible following insemination or exposure to males is key in managing reproductive cycles, because it allows producers to make decisions early regarding rebreeding strategies. In an effort to make a profit, livestock producers must strive for a high pregnancy rate, calf crop and heavy weaning weights.

Pregnancy detection procedures for livestock animals should be inexpensive, sensitive and highly accurate. One way to determine pregnancy status is to observe signs of estrus (heat) after insemination. While this approach is effective, it is expensive, labor intensive, very time consuming, and not very accurate. Other methods of pregnancy detection include detection by rectal palpation, which is more accurate that checking estrus, but also is labor intensive and not feasible early during pregnancy. The current gold standard for determining pregnancy in cattle is through rectal ultrasound on day 32 of pregnancy. Similarly, the optimum time for detecting pregnancy in sheep using transabdominal B-mode ultrasonography ranges from 25 to 110 days of gestation, optimally from 45 to 90 days of gestation.

Maternal recognition of pregnancy in ruminants requires elongation of the conceptus coinciding with production of interferon-tau (IFNT). The ovine conceptus secretes IFNT from Days 10 to 21-25 with greatest release occurring on Days 14 to 16 of pregnancy, although the precise pattern of secretion of IFNT and activation of interferon-stimulated genes (ISGs) has not been fully described. IFNT is a major product of ovine and bovine conceptuses before attachment that functions to prevent the return to estrous cycles. IFNT acts in a paracrine manner to silence up-regulation of (estradiol receptor) ESR1 and oxytocin receptor (OXTR) in the endometrial luminal epithelium and superficial glandular epithelium, thereby preventing the release of prostaglandin F2α (PGF). In addition, IFNT has recently been reported to function through endocrine action in the ovine corpus luteum (CL).

IFNT binds type 1 receptors (IFNR1 and IFNR2) and activates the Janus kinase-signal transducer and activator of transcription (JAK/STAT) pathway. The JAK/STAT pathway includes downstream mediators such as the signal transducer and activator of transcription (STAT)s (1 and 2), interferon regulatory factor (IRFs) and IFN-stimulated genes (ISGs). A hypothesized mechanism of how IFNT mediates maternal recognition of pregnancy is through the increased expression of several ISGs in the uterus, such as ISG15, Interferon-induced with helicase C domain 1 (IFIH1), and DEAD (Asp-Glu-Ala-Asp) box polypeptide 58 (DDX58). Additionally, pregnancy induces expression of ISGs in several ovine extra uterine tissues, such as the corpus luteum (CL). ISG15, first termed ubiquitin cross-reactive protein because of its cross-reactivity with antibody against ubiquitin increases in mouse and human endometrium in response to pregnancy. ISG15 is induced by type I IFN and becomes conjugated to intracellular proteins in a mechanism parallel, but different to that described for ubiquitin.

The Inventors have previously demonstrated that sheep have increased antiviral activity in uterine vein serum (UVS) during early pregnancy. Antiviral activity is blocked in Day 15 UVS of pregnancy when preadsorbed with anti-interferon-tau (IFNT) antibodies.

SUMMARY OF THE INVENTION

The present invention relates to compositions, systems, kits, and methods that allow for detection of pregnancy in ruminant animals. The invention allows for detection earlier in pregnancy than other methods, and in particular earlier than standard methods currently used. The invention allows for identification of nonpregnant animals so that a decision can be made earlier that current approaches on how to manage the nonpregnant animal.

In one embodiment, the invention provides a method for detecting pregnancy in an animal comprising obtaining a sample from an animal suspected of being pregnant; determining whether IFNT is present in said sample; and diagnosing the animal as pregnant if IFNT was determined to be present in said sample. In a preferred embodiment, the determining step is performed by contacting the sample with a purified antibody specific for IFNT and detecting whether binding occurs between said antibody and IFNT. In a more preferred embodiment, the detection of the determining step is accomplished using antibody-based radioimmunoassay, enzyme linked immunoabsorbent assay (ELISA), lateral flow or dip-stick detection. In another preferred embodiment, the determining step is accomplished using mass spectrometry.

In a preferred embodiment, the methods are used to detect pregnancy in ruminant animals. In a more preferred embodiment, the methods detect pregnancy in cows or sheep. In a preferred embodiment, the sample is collected from said animal less than 21 days after breeding. In a more preferred embodiment, the sample is collected between 16 and 21 days after breeding.

In another embodiment, the invention provides methods for impregnating a female ruminant animal, comprising collecting a sample from said animal, determining whether interferon tau (IFNT) is present in said sample, diagnosing a female ruminant animal as not pregnant (NP) if IFNT was determined not to be present in said sample, and performing additional breeding if the female animal was determined to be NP. In a preferred embodiment, the sample is collected between 16 and 21 days after breeding in cattle. In one preferred embodiment, the female ruminant animal is bovine. In one aspect, where the animal is bovine, the sample is collected less than 21 days after breeding, and even more preferably between 16 and 21 days after breeding. In another preferred embodiment, the female ruminant animal is ovine. Because estrous cycles are shorter in other ruminants, for example 16-17 days in sheep compared to 21 days in cattle, samples may be collected earlier than day 16 in sheep. In another aspect, the methods for impregnating are used to increase the number of offspring in a population of animals, such as a herd of cattle or sheep, by carrying out the impregnating methods on two or more female animals in the population. In a preferred embodiment, additional breeding is performed on all of the animals in the population that are determined to be NP.

Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION OF THE INVENTION

Figure 1A:
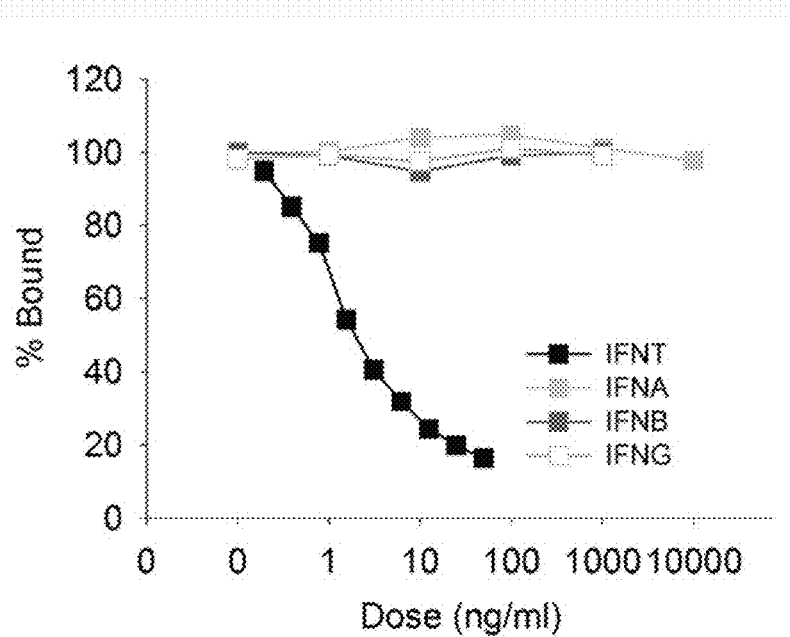
FIG. 1(A-B) shows ovine IFNT radioimmunoassay. (A) Specificity: competitive radioimmunoassay testing IFNT against other type I (alpha and beta) and type II (gamma) interferons. (B) Sensitivity: radioimmunoassay testing different antibody concentrations. * indicates means differ (P<0.05).

This invention includes novel methods for determining pregnancy status in ruminant animals, methods for impregnating ruminant animals, and methods for increasing the growth rate of a population of ruminant animals. The methods increase the likelihood that an individual animal is pregnant by detecting pregnancy status early (e.g. less than 21 days after insemination in cows, less than 16 days after insemination in sheep), thereby permitting management of nonpregnant animals, e.g. by performing additional breeding. These methods are advantageous over using ultrasound or rectal palpation, because they allow for determinations to be made earlier, thereby permitting earlier decisions regarding management. Pregnancy is detected by assaying for the presence of conceptus-derived IFNT in the maternal peripheral blood through specific and sensitive techniques provided herein. Animals determined not to be pregnant through detection of no IFNT can be re-bred, and the process of determining pregnancy can be repeated.

Terms and Abbreviations

Unless explained otherwise, all technical and scientific terms used herein have the same meaning as commonly understood to one of ordinary skill in the art to which this disclosure belongs. All references herein are incorporated by reference. The following explanations of terms and abbreviations are provided to better describe the present disclosure and to guide those of ordinary skill in the art in the practice of the present disclosure.

All numbers expressing quantities of components, molecular weights, percentages, temperatures, times, length, and so forth, as used in the specification or claims are to be understood as being modified by the term "about" unless otherwise indicated.

As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

The term "sample" describes any type of sample suspected to contain a desired target protein to be assayed for detection of such target protein. In some embodiments a biological sample from a subject suspected of being pregnant, will be used, such as blood, plasma or serum, or other bodily fluids that may contain the target protein. These may include, for example, plasma, serum, spinal fluid, lymph fluid, secretions from the respiratory, gastrointestinal, or genitourinary systems including tears, saliva, milk, urine, semen, hepatocytes, and red or white blood cells or platelets. Samples may also be obtained from tissue cell culture, such as cultured hepatocytes or leukocytes, and constitute cells, including recombinant cells, or medium in which the target may be detected. In some cases, a tissue sample may be used in the assay or processed for use in the assay, for example, by a conventional method used to extract proteins from the sample.

As used herein, the "effective amount" of a compound of the invention required for the use in the method presented herein will differ not only with the particular compound to be selected but also with the mode of application, and the nature of the sample specimen. The exact amount will be evaluated by testing with a sufficient number of clinical samples in each application as conducted by persons skilled in the art. However, a generally suitable concentration will range from about 10 pg/ml to 10 ng/ml of testing solutions. Furthermore, the compounds may be used as pure compounds, for example pure protein or peptide applied to a test solution, or as a pure chemically acceptable salt or derivative. However, it is preferable to provide the active chemical or its chemically acceptable salt or derivative, as a medicinal formulation, either as a dry material (reaction solution provided separately), or as a solution or suspension (an aqueous solution or other chemically acceptable solvent solutions), or as a lateral flow or dip stick device.

The term "purified polypeptide" "purified antibody", "purified protein", or "purified peptide" describes a protein, polypeptide or peptide, including antibodies and fragments thereof, which has been isolated from the host tissues or fluids in which the polypeptide, protein, or antibody is normally associated, isolated from a tissue cell culture, or separated from other types of microorganisms, such as bacteria or other viruses. Techniques for isolating peptides, polypeptides, proteins, and antibodies are known to those of skill in the art.

An "isolated" antibody is one that has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) approaches. For review of methods for assessment of antibody purity, see, e.g., Flatman et al., J. Chromatogr. B 848:79-87 (2007).

The term "preservative or additive for a sample" includes additives such as heparin or EDTA. The term also includes other agents that prevent degradation of polypeptides or permit polypeptides to be easily recognized in the method of the invention. These include normal saline or commercially available preservatives. The term "extraction buffer" refers to conventional agents and materials useful for extracting, purifying or isolating polypeptides from a sample, such as a biological sample like serum, plasma, milk or other bodily secretion.

The term "denaturation" refers to a process of unfolding of nucleic acids or polypeptides. For example, by heating a sample to 65, 75, 85, 90, 95-100° C. Denaturation may also be facilitated by addition of other ingredients such as salts, formamide, sodium hydroxide or reducing agents (e.g. beta mercaptoethanol (βME), Dithiothreitol (DTT)).

The term "reaction buffer" describes a composition in which a sample and antibody interact. Exemplary buffers include phosphate buffer saline, and other buffers used in reaction mixtures.

The term "target region" describes the portion of the IFNT protein to which an antibody binds. Target regions may include carbohydrate moieties of glycosylated amino acids of the protein or polypeptide.

The term "target protein" or "target polypeptide" refers to a protein or polypeptide from a sample corresponding to synthetic or natural polypeptides, proteins, or fragments thereof, or modified or mutant polypeptides or proteins. It also encompass modified or mutated polypeptide sequences, such as variants containing one or more single amino acid variations, or more generally, those having a polypeptide sequence containing 1, 2, 3, 4, 5 or more insertions, deletions, transpositions, or substitutions to the amino acid sequence.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd).

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, Front. Biosci. 13:1619-1633 (2008).) Unless otherwise indicated, HVR residues and other residues in the variable domain (e.g., FR residues) are numbered herein according to Kabat et al., supra.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Radioimmunoassay" and "RIA" refers to in vitro assay techniques in which radioactive labelled antigen is mixed with unlabelled antigen (the test sample) and allowed to bind to an antibody or antigen binding fragment thereof. Bound antigen is physically separated from unbound antigen and the amount of radioactive antigen bound to the antibody determined. The more antigen there is in the test sample the less radioactive antigen will bind to the antibody. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Enzyme-linked immunosorbent assays (ELISA) are standard in the art and can be found at, for example, Ausubel, F. M. et al., (Current Protocols in Molecular Biology, Volume 2, pp. 11.2.1-11.2.22, John Wiley & Sons, Inc., 1991). ELISA typically uses an enzymatic reaction to convert substrates into products having a detectable signal (e.g., fluorescence). Each enzyme in the conjugate can covert hundreds of substrates into products, thereby amplifying the detectable signal and enhancing the sensitivity of the assay. ELISA assays are understood to include derivative and related methods, such as sandwich ELISA and microfluidic ELISA.

The term "heterologous polypeptide" or "heterologous protein" refers to a polypeptide or protein that is derived from a different source, a native polypeptide in which modifications have been made to alter the native sequence, or a native polypeptide whose expression is quantitatively altered as a result of a manipulation of the gene encoding the polypeptide by recombinant DNA techniques. In the context of a fusion protein or peptide, a "heterologous polypeptide sequence" refers to a polypeptide sequence that comprises one or more subsequences that are not found in the same relationship to each other in nature.

"Breeding" as used herein refers to known methods and techniques of inseminating or impregnating an animal to produce offspring. "Breeding" includes husbandry and mating approaches, as well as non-mating approaches such as, for example, artificial insemination, in vitro fertilization, and embryo transfer.

The examples herein use several specific sequences, but it will be appreciated by one of ordinary skill in the art that other sequences are readily amenable for use in the disclosed methods.

Methods of Detecting Pregnancy Status

In one aspect, the present invention includes methods for detecting whether an animal is pregnant. The detection method of the invention comprises obtaining a sample from an animal, obtaining a sample from an animal, determining whether interferon tau (IFNT) is present in said sample, and diagnosing the animal as pregnant if IFNT was determined to be present in said sample, or as non-pregnant (NP) if IFNT is determined not to be present. In a further aspect, the determining step is performed by contacting the sample with a purified antibody specific for IFNT and detecting whether binding occurs between said antibody and IFNT. Alternatively, the determining step is performed by mass spectrometry (MS). The invention further comprises other methods for specific detection of IFNT, including, for example, colorometric or flurochromic detection assays. Such assays include immune assays such as ELISA, microfluid ELISA, Western blot, flow cytometric assays, and dip stick or lateral flow strip tests.

In one aspect, the methods of the present invention may include a step for concentrating or enriching a sample collected from an animal. Concentrating or enriching a sample can be accomplished using techniques known in the art, including one or more of filtration, centrifugation, evaporation, extraction, chromatography, affinity chromatography, precipitation and the like.

Following the determining step, the methods involve diagnosing the animal as pregnant if IFNT is determined to be present in the sample. Alternatively, the method can involve diagnosing the animal as not pregnant if IFNT is determined to be absent in the sample.

In a preferred embodiment, the sample is obtained at a time that corresponds to early pregnancy. For example, in bovines, the sample may be obtained less than 21 (e.g., 16-21) days after breeding, or less than 16 days after breeding in ovines. Further, sample collection can be timed to increase the chances of detecting the presence or absence of IFNT in the sample by choosing a time when IFNT should be at the highest concentration in the sample. Alternatively, sample collection can be timed to determine whether or not an animal is pregnant as early as possible.

In another aspect, detection of IFNT may be coupled with detection of a second indicator of a viable CL such as serum progesterone.

Antibody-Based Detection

Detection of IFNT by contacting the sample with a purified antibody specific for IFNT and detecting whether binding occurs can be performed using a number of antibody-based techniques known in the art. Antibody-based techniques are understood to include any technique that uses an antibody, or antigen-binding fragment thereof, to specifically bind a target molecule or analyte. Examples of antibody-based techniques include radioimmunoassay, ELISA, lateral flow tests, dipstick test, Western blot, and similar techniques.

In one embodiment, the determining step of the method is accomplished by contacting the sample with a purified antibody that is specific for IFNT. The antibody can be selected based on a number of factors, including species of the animal from which the sample was obtained and the type and extent of processing, concentrating, or enriching to which the sample is subjected. For example, an antibody specific for a particular epitope may be selected for detecting IFNT in samples that are processed in a manner, such as heating and evaporation, which can denature the native protein.

In one aspect, radioimmunoassays of the present invention may utilize radiolabeled antigen, such as recombinant IFNT labeled with $^{125}$I. Alternatively, the assay can use non-radioactive antigen, using antigen or an analogue linked to a reporter molecule. The reporter molecule can be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

In another aspect, detection of IFNT can be by ELISA. ELISA typically uses an enzymatic reaction to convert substrates into products having a detectable signal (e.g., fluorescence). Each enzyme in the conjugate can covert hundreds of substrates into products, thereby amplifying the detectable signal and enhancing the sensitivity of the assay. ELISA assays are understood to include derivative and related methods, such as sandwich ELISA and microfluidic ELISA.

Alternative antibody-based techniques for the methods of the present invention include lateral flow tests, also known as lateral flow immunochromatographic assays. Lateral flow tests are simple devices intended to detect the presence (or absence) of a target analyte in sample (matrix) without the need for specialized and costly equipment, although assays may be set up in conjunction with equipment for reading test results. The technology is based on a series of capillary beds, such as pieces of porous paper or sintered polymer. Each of these elements has the capacity to transport fluid samples spontaneously. The first element (the sample pad) acts as a sponge and holds an excess of sample fluid. Once soaked, the fluid migrates to the second element (conjugate pad) in which the manufacturer has stored the so-called conjugate-bio-active particles formulated to facilitate chemical reaction between the target molecule in the sample and its chemical partner (e.g., antibody) that has been immobilized on the particle's surface. After reacting with the conjugate, the sample moves to one or more areas (often called stripes) where a third 'capture' molecule has been immobilized to bind the complex. As the sample passes through the stripes, particles accumulate and the stripe-area changes color. Typically there are at least two stripes: one (the control) that captures any particle and thereby shows that reaction conditions and technology worked fine; and a second that contains a specific capture molecule and only captures those particles with target molecule bound to the antibody. Lateral flow tests can operate as either competitive or sandwich assays.

In another alternative embodiment, detection of IFNT can be by the use of a dipstick test. A testing dipstick is usually made of a substrate, for example paper or cardboard, which is impregnated with reagents that indicate some feature of the liquid by changing color. Dipsticks used to test for a variety of liquids for the presence of a given analyte or target molecule are known in the art.

Mass Spectrometry Assays

Mass spectrometry (MS) is an analytical method that combines the features of gas-liquid chromatography and mass spectrometry to identify different substances within a test sample. MS is considered a gold standard for substance identification because it positively identifies the actual presence of a particular substance in a given sample. In one aspect of the invention, a sample obtained from an animal is injected into the injection port of the MS device and analyzed for the specific presence of IFNT. In a preferred embodiment, a sample to be assayed for the presence of IFNT is subjected to peptide digest, for example using trypsin, before MS. In a more preferred embodiment, IFNT is detected in a digested sample by detection of one or more digestion products. For example, the digest products may be any of the peptides set out in Tables 1-3, or SEQ ID NOS: 7, 9, and 11. The absence of IFNT protein, or digestion products thereof, as detected by MS indicates that the ruminant animal from which the sample was collected is not pregnant.

Kits for Determining Pregnancy Status of Ruminant Animals

The term "kit" refers to a composition of matter containing one or more ingredients necessary to practice the method of detecting pregnancy status according to the invention. Preferably, the kit will contain an antibody specific for IFNT.

A kit may also contain at least one biological sample preservative or additive for a sample, such as an agent that prevents degradation of proteins, a reaction buffer in which antibody and biological sample are mixed, a negative control sample, a positive control sample, one or more reaction containers, such as tubes or wells, a colorimetric chart, a packaging material, an instruction for use in detecting the same.

The examples below are provided only for illustrative purposes and not to limit the scope of the present invention. Numerous embodiments within the scope of the claims will be apparent to those of ordinary skill in the art, thus the following non-limiting examples only describe particular embodiments of the invention. The present invention relates to colorimetric read-out systems capable of detecting a variety of biomolecules, including methods and kits relating thereto.

To facilitate a better understanding of the present invention, the following examples of preferred or representative embodiments are given. In no way should the following examples be read to limit, or to define, the scope of the invention.

EXAMPLES

Example 1: Temporal Release, Paracrine and Endocrine Action of Conceptus-Derived Interferon-Tau During Early Pregnancy in Ewes The Inventors have demonstrated that IFNT induces gene expression in the endometrium and enters peripheral circulation inducing genes in extrauterine tissues such as the corpus luteum (CL) and liver. In exemplary experiments described herein, blood was collected from ewes on Days 12-15 of the estrous cycle (non-pregnant, NP) or pregnancy and on Day 16 of pregnancy. Serum progesterone concentrations remained >1.7 ng/ml in pregnant (P) ewes and in NP ewes on Days 12-13 of the estrous cycle, but declined to concentrations <0.6 ng/ml by Day 15 of the estrous cycle. A highly specific (no cross-reaction with IFNα, IFNβ or IFNγ) and sensitive (71.25 pg/ml in uterine flushings; 58.7 pg/ml in serum) IFNT radioimmunoassay (RIA) was validated herein and used to demonstrate that IFNT was not detected in NP ewes but could be detected from Days 13-16 of pregnancy in uterine flushings and detected uterine vein serum (UVS) on Days 15-16. IFNT detection in uterine flushing correlated with paracrine induction of ISGs in endometrium and preceded blocking up-regulation of endometrial ESR1 and OXTR by Day 14. The induction of ISG mRNAs in jugular vein white blood cells, liver and CL occurred by Day 14, prior to detection of IFNT in UVS on Day 15 of pregnancy. To confirm activation of IFNT signal transduction in CL, mRNA concentrations of IFN signal transducers and ISGs were determined to be greater in CL from Day 14 P compared to NP ewes. Thus, the Inventors have shown that paracrine action of IFNT coincides with IFNT detection in uterine flushings, and endocrine action of IFN ensues through induction of ISGs in peripheral blood.

Based on the Inventors' previous demonstration of antiviral activity in the uterine vein serum on Day 15 of pregnancy being blocked by pre-adsorption using anti-IFNT antibody and a higher expression of ISG15 in CL from a Day 15 pregnant (P) ewe, the Inventors determined whether endocrine IFNT signaling occurs during maternal recognition of pregnancy in ruminants as early as Day 14 of pregnancy. The Inventors therefore developed a sensitive and specific radioimmunoassay used to examine IFNT levels in uterine flushings and uterine vein blood.

Because IFNT was detected in uterine flushing and uterine vein blood, these studies also provide important insight into regulation of endometrial, corpus luteum and liver gene expression. Some of the well-characterized endometrial responses to IFNT also were examine in the CL such as silencing of ESR1 and OXTR mRNA in the CL. Several studies have examined changes in mRNA for ISGs, ESR1 and OXTR in ovine endometrium in response to early pregnancy, but these studies have not examined consecutive Days of pregnancy in context of uterine flushing and uterine vein concentrations of IFNT.

Notably, none of the previous published experiments have focused on temporal relationships between paracrine effects of the conceptus on the endometrium, development of antiluteolytic responses and endocrine induction of genes CL on Days 12, 13, 14, and 15. This represents a period in which critical responses mediate maternal recognition of pregnancy in the ewe.

The aim of this work was to develop a specific and sensitive radioimmunoassay for IFNT, initially for the detection of IFNT in uterine flushings and uterine vein blood, and ultimately for potential detection of IFNT in maternal blood for detection of pregnancy. These methods can be used to manage ruminant animals and ruminant animal populations by identifying nonpregnant animals so that that they can be better managed to become pregnant. The temporal relationships in detecting IFNT and regulation of ISG15, ESR1 and OXTR in the endometrium, and IFN signaling in the CL were examined.

Experimental Design: Day of Estrous Cycle and Early Pregnancy

Mature crossbred ewes were observed daily for estrus using a caudoepididectomized ram. On the Day of standing estrus (Day 0), half of the ewes were bred with an intact ram. NP ewes were not exposed to a ram. Groups were assigned according to pregnancy status (NP and P) and Days after detection of estrus (12, 13, 14 and 15). Three to six ewes per Day and per pregnancy status were used (12NP=5; 12P=4, 13NP=5; 13P=5, 14NP=5; 14P=3, 15NP=6; 15P=4). On Days 12, 13, 14 and 15 of either the estrous cycle or pregnancy, ewes were euthanized and jugular and uterine vein blood, lymph nodes (iliac and submandibular), CL, endometrium, uterine vein (tissue) and liver were collected.

Tissues were snap frozen in liquid nitrogen and kept at −80° C. for later processing. Pregnancy was confirmed by the presence of a conceptus.

Progesterone Assay

Concentration of progesterone in serum was determined by radioimmunoassay according to standard procedures. All samples were analyzed in one assay. The sensitivity was 6.07 pg/ml and the intra-assay coefficient of variation was 4.85%.

IFNT Radioimmunoassay (RIA)

Radioiodination of recombinant ovine IFNT (roIFNT) with $^{125}$I was completed using chloramine T procedure and purified using column chromatography using commonly known methods. Briefly, uterine flushing samples were diluted 1:50 in 0.1% PBS gel for analysis in the RIA. If the samples were undetectable in the first run, they were reanalyzed un-diluted. Anti-roIFNT antibody (1:60,000 dilution) was added to uterine flushing samples, vortexed and incubated at 4° C. for 24 hours. Radioactive $^{125}$I-labeled roIFNT was added (100 μl 50,000 counts), vortexed and incubated for 24 hours at 4° C. This was followed with incubation at 4° C. for 72 hours with secondary anti-rabbit gamma globulin antibody (1:25 dilution). The assay was terminated by addition of 3 ml of cold PBS and centrifugation at 2800 rpm for 30 minutes. The supernatant was removed and the radioactivity of the pellet was determined utilizing a gamma counter (Apex automatic gamma counter, ICN Micromedic Systems). This RIA was optimized for detection of roIFNT in uterine flushing samples at a sensitivity of 0.1 ng/ml and a range of detection of 0.1 to 13 ng/ml. The intra-assay coefficient of variation was 6.2% and the inter-assay coefficient of variation was 4.0%.

RIA Detection of IFNT in Uterine Flushing Samples and Uterine Vein Serum

Figure 1B:
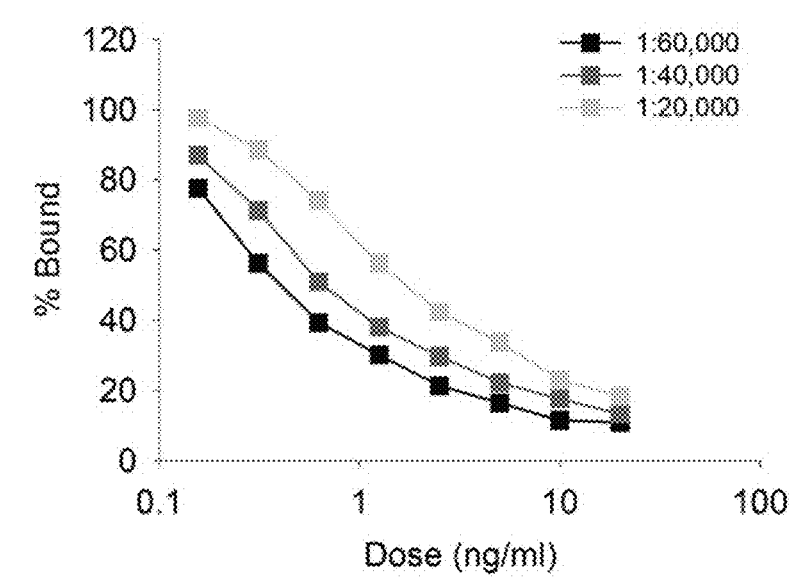
Figure 2A:
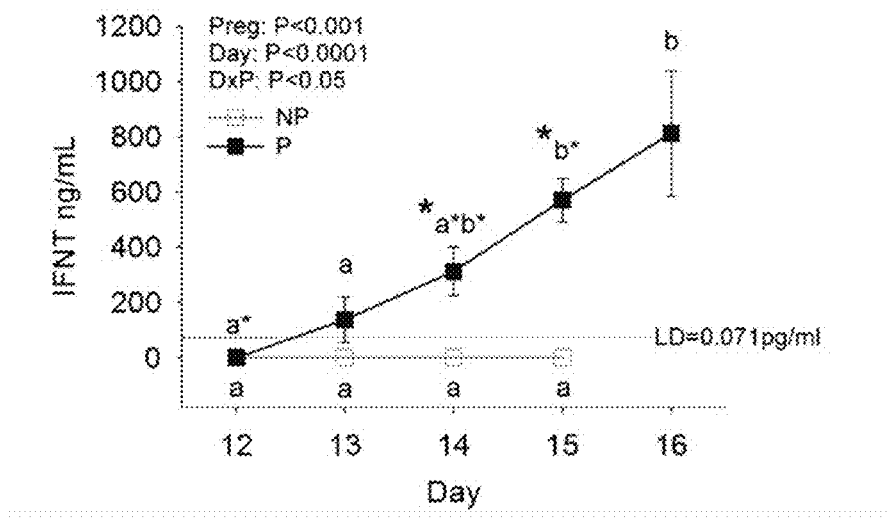
FIG. 2(A-B) shows detection of ovine IFNT in uterine flushing and uterine vein using RIA. (A) Detection of IFNT in uterine flushings from Day 12-15 non-pregnant and pregnant ewes. (B) Detection of IFNT in uterine vein serum from Days 12-15 non-pregnant and pregnant ewes. * indicates means differ (P<0.05).
Figure 2B:
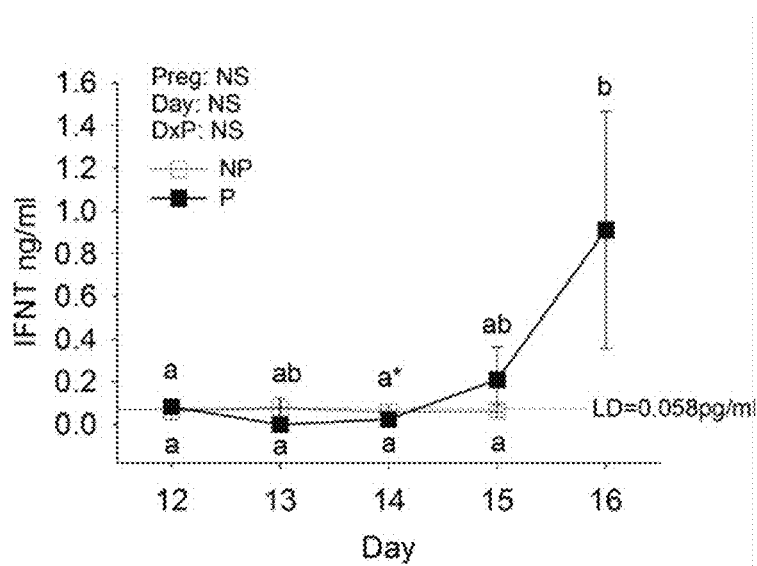
Figure 3:
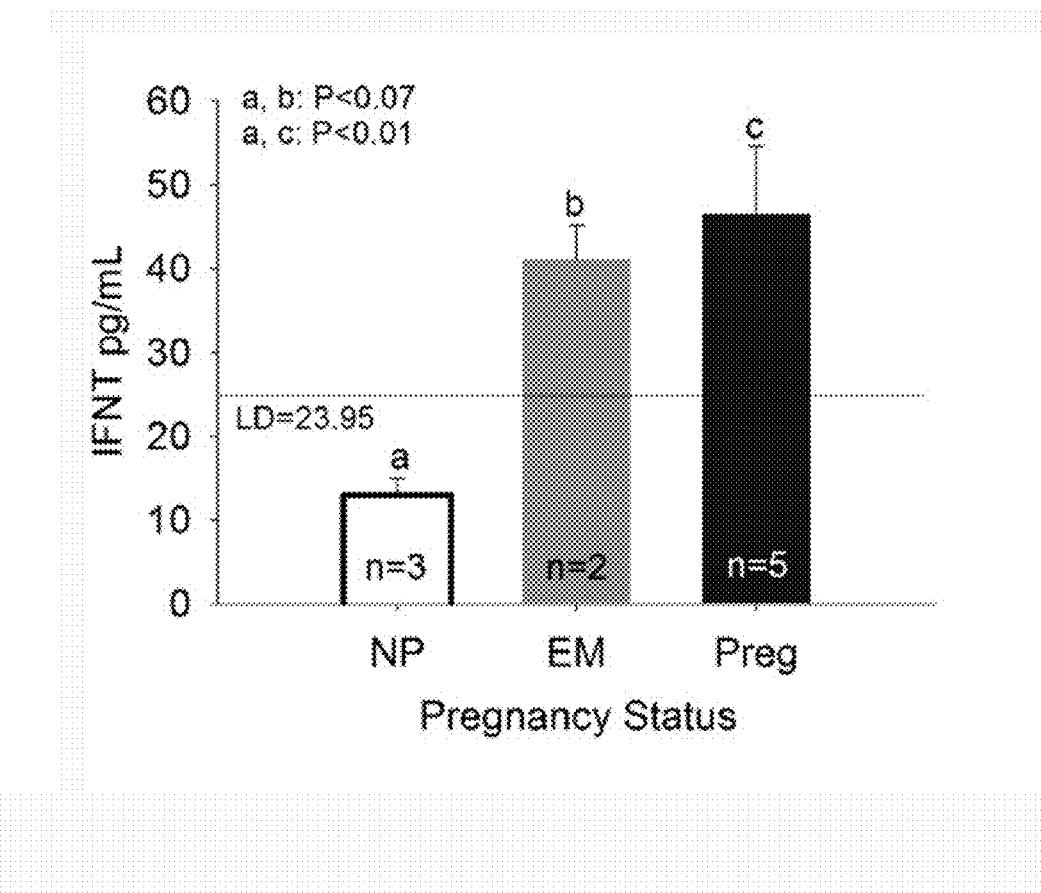
FIG. 3 shows pregnancy status of day 19 dairy cows identified by blood test for IFNT. Concentration of IFNT (pg/mL) in day 19 tail blood from NP (Non-pregnant) cows exposed to semen, cows that were NP to term but had detectable limits at day 19, and possibly had a fetus but lost it (Embryonic Mortality; EM) and P (Pregnant) cows that calved. DL is the limit of detection for this assay. Letters signify P<0.05 and * is P<0.1.

Specificity of the IFNT RIA was tested against other IFNs such as IFNα, β, and γ; revealing no cross reactivity of the anti-IFNT antibody with similar (type I) or distinct (type II) IFNs (FIG. 1A). Sensitivity of the assay was optimized utilizing various primary antibody dilutions. The 1:60,000 dilution was identified as optimal (FIG. 1B). Uterine flushings were collected from NP ewes on Days 12, 13, 14 and 15. These samples had non-detectable concentrations of IFNT serving as a negative control. Three standard dose response curves were run within each assay to serve as positive controls. IFNT was detectable as early as Day 13 of pregnancy in uterine flushings and by Day 15 in uterine vein blood, concentrations increased thereafter on each Day of pregnancy up to Day 16 (FIG. 3). The range of detection for these assays was between 11 pg/ml to 23 ng/ml. The limit of detection in uterine flushings was 71.25 pg/ml and in uterine vein serum it was 58.7 pg/ml. The interassay coefficients of variation for the 3 assays ranged from 7.25% to 14.7% and the intrassay coefficient of variation was 10.1%.

Discussion

IFNT is produced by the ruminant conceptus and for the last three decades was thought to have only paracrine function through binding to receptors on the maternal endometrium of the. The primary paracrine role of IFNT during early pregnancy is antiluteolyic and mediated through disruption of prostaglandin F2-alpha release from the uterus. This restriction of detection and action of IFNT within the uterine lumen was based on lack of detection of antiviral activity in peripheral blood, utilizing a bioassay for IFN, and more recently was based on lack of detection of IFNT in blood using antibody-based detection methods.

Increased antiviral activity caused by pregnancy has not been observed in systemic blood collected from ruminants during early pregnancy. However, one report by Schalue-Francis, Farin et al. in 1991 described an antiviral assay with a sensitivity of ~1 unit/ml that could not detect IFNT in jugular vein blood, but was efficacious in detecting 58 U/ml uterine vein serum from Day 15 pregnant sheep. Conversion of 58 U/ml is equivalent to 7.25 ng/ml based on the 8×10$^8$ U/mg IFN standard. The conclusion that IFNT was not detectable in jugular vein blood also was based on antibody-based detection of IFNT in ELISA and RIA. Previous attempts to develop RIA for IFNT by others exhibited apparent sensitivity of detecting 6.1-7.8 ng IFNT/ml, based on a reported a sensitivity of 6.1 ng/ml, but the lowest standard used in the assay was 7.8 ng with binding of ~95%. Use of this RIA by these authors revealed detection of IFNT in uterine flushing representing Day 16 of bovine pregnancy. There was no report of attempting to detect IFNT in blood in these previous reports.

More recent work by the Inventors also found detectable antiviral activity in uterine vein blood from Day 15 pregnant sheep, with no detection of antiviral activity in systemic blood. The antiviral activity was attributed specifically to IFNT and not other type I IFNs, through blocking antiviral activity in uterine vein blood using preadsorption with an antibody against IFNT. The amount of IFNT in uterine vein blood on Day 15 of pregnancy was ~500-1,000 U/ml, which was estimated to be 5-10 ng/ml using 1×10$^8$ U/mg IFN standard.

Indirect evidence that IFNT might be released from the uterine vein and has a systemic-endocrine role during pregnancy was demonstrated by up-regulation of interferon-stimulated genes (ISGs) in peripheral blood cells. Based on these studies, it was concluded that IFNT was produced by the conceptus during early stages of pregnancy, attenuated PGF release from the endometrium, and was released into the uterine vein in high enough concentrations to possibly have a functional and biological effect on peripheral tissues such as blood cells, the corpus luteum and liver. However, until the present enclosed experiments, no one has been able to directly detect IFNT circulating in the blood during early pregnancy in ruminants.

A double antibody radioimmunoassay (RIA) for IFNT is described herein using recombinant ovine IFNT and anti-roIFNT antibody. This RIA was confirmed to be specific for IFNT because the anti-IFNT antibody did not cross-react with other type I IFN such as alpha and beta or with type II IFN such as IFN gamma. After specificity of the IFNT RIA for IFNT was demonstrated by lack of competition by up to 10 μg/ml of related, but not identical type I and II IFN. Sensitivity of this IFNT RIA was improved through increasing dilutions of the primary antibody. The amount of ligand required to displace 50% binding deceased from ~1.5 ng to 0.4 ng with increasing dilutions of primary anti-IFNT antibody to 1:60,000. While this assay had improved sensitivity, and was very useful when detecting IFNT in ovine uterine flushings from Days 13-16 of pregnancy and in uterine vein blood from Days 15 to 16 of pregnancy, it was not able to detect IFNT in jugular vein blood in sheep or in tail vein blood from similar stages of early pregnancy in cattle (data not shown). The sensitivity of the assay in ovine uterine vein flushings was about 70 pg/ml. The sensitivity of the assay for IFNT in serum was only 200 pg/ml; which was significantly improved over other assays described for IFNT, but possibly not enough to allow detection of IFNT in the blood. The sensitivity of the IFNT RIA using serum may have been impacted by factors in serum that are not present in uterine flushing which interfered with the assay.

Example 2: Detection of Interferon-Tau in Blood from Pregnant Dairy Cows Using Radioimmunoassay The Inventors developed a sensitive radioimmunoassay (RIA) for bovine and ovine IFNT. This assay has application for use in all ruminant species. IFNT is release by the ruminant conceptus and historically was thought to be sequestered in the uterine lumen with no release into the systemic circulation in detectable amounts. IFNT is only produced by the trophectoderm cells of the ruminant embryo. For this reason it is a very specific marker for presence of a conceptus (embryo proper and extrembryonic trophectoderm). The greater antiviral activity described in uterine vein blood from Day 15 pregnant compared to nonpregnant sheep, together with ablated antiviral activity obtained by preadsorption of uterine vein blood from Day 15 pregnant sheep with antibody against IFNT demonstrates that the active antiviral cytokine in uterine vein blood was IFNT. This was confirmed by detection of IFNT in uterine vein blood by Day 16 of pregnancy in sheep using RIA and by mass spectroscopy approaches. To date, IFNT has not been found in peripheral blood in sheep or cattle during early pregnancy. The Inventors therefore developed a method of detection of IFNT in blood from cattle by Day 18 of pregnancy by optimizing primary anti-IFNT antibody dilution, reducing background in the assay because of matrix effect and using freshly collected serum. Detection of IFNT in tail vein or jugular vein blood is novel and significant in context of application for identify cattle carrying a conceptus. The present invention has particular utility in identification of cattle that are not carrying an embryo and can be managed immediately to return to estrus and ovulation.

IFNT Peptide and Glycosylation Identification after Trypsin Digest

In order to determine IFNT peptides that are conserved across the ovine and bovine species after trypsin digestion, the proper sequence identifications were located utilizing uniprote and placed into ExPASy peptide cutter program. From there the peptides were placed into ExPASy glycomod program to identified glycosylated amino acids on the bovine amino acid sequence that would increase the mass of the amino acids. From there the amino acids were compared for conservation between the species and an absence of glycosylation.

Radioimmunoassay Identification of IFNT in Peripheral Blood

Utilizing the assay with serum added to the standard we were able with 100% accuracy to determine if a dairy cow was pregnant by measuring IFNT in Tail blood samples collected on day 19 after artificial insemination (FIG. 3). In cows that were bred but did not calve we determined that 3 were not pregnant and 2 appeared to be pregnant at day 19 but later lost the conceptus (FIG. 3). In aims to improve detection methods, reduce cost and analysis time due to analysis with RIA, protein enrichment, mass spectroscopy and gas chromatography methods have also been developed (see Example 3, infra).

Identification of Three Conserved IFNT Peptides that are not Glycosylated

Utilizing the ExPASy modeling software we were able to trypsin digest ovine and bovine IFNT and determine conserved amino acid sequences between the two (Table 1). This software was also used to determine amino acids that have the potential to be glycosylated in bovine IFNT peptides changing the molecular mass of the peptide (Table 2; potential glycosylation sites bolded). These two comparisons revealed 3 unique and conserved peptide sequences for bovine and ovine IFNT to be further utilized for mass spectroscopy and gas chromatography identification in serum (Table 3).

TABLE 1

Conserved IFNT Peptide Amino Acid Sequences.

| Sheep | | Bovine | |
|---|---|---|---|
| AA sequence | Mass (Da) | AA sequence | Mass (Da) |
| ENLR (SEQ ID NO: 5) | 530.581 | ENLR (SEQ ID NO: 5) | 530.581 |
| LLDR (SEQ ID NO: 6) | 515.610 | LLAR (SEQ ID NO: 7) | 471.600 |
| MNRPSPHSCLQDR (SEQ ID NO: 8) | 1540.735 | MNR | 419.449 (1584.781) |
| | | LSPHPCLQDR (SEQ ID NO: 9) | 1165.332 |
| K | 146.189 | K | 146.189 |
| MDPIVTVK (SEQ ID NO: 10) | 902.117 | MGPILTVK (SEQ ID NO: 11) | 858.107 |
| YFQGIHDYLQEK (SEQ ID NO: 12) | 1540.695 | YFQGIHVYLK (SEQ ID NO: 13) | 1267.493 |
| VEMMR (SEQ ID NO: 14) | 664.836 | VEMMR (SEQ ID NO: 14) | 664.836 |
| ALTSSTTLK (SEQ ID NO: 15) | 921.059 | ALSSSTTLQK (SEQ ID NO: 16) | 1035.162 |

TABLE 2

Glycosylated Amino Acids in Conserved IFNT Sequences.

| Bovine AA sequence | Mass (Da) |
|---|---|
| ENLR (SEQ ID NO: 5) | 530.581 |
| LLAR (SEQ ID NO: 7) | 471.600 |
| MNR | 419.449 |
| LSPHPCLQDR (SEQ ID NO: 9) | 1165.332 |
| K | 146.189 |
| MGPILTVK (SEQ ID NO: 11) | 858.107 |
| YFQGIHVYLK (SEQ ID NO: 13) | 1267.493 |
| VEMMR (SEQ ID NO: 14) | 664.836 |
| ALSSSTTLQK (SEQ ID NO: 16) | 1035.162 |

TABLE 3

Non-glycosylated Conserved Peptide Sequences for Mass Spectroscopy Identification of IFNT.

| Sheep | | Bovine | |
|---|---|---|---|
| AA sequence | Mass (Da) | AA sequence | Mass (Da) |
| ENLR (SEQ ID NO: 5) | 530.581 | ENLR (SEQ ID NO: 5) | 530.581 |
| K | 146.189 | K | 146.189 |
| VEMMR (SEQ ID NO: 14) | 664.836 | VEMMR (SEQ ID NO: 14) | 664.836 |

Protein Enrichment Prior to Identification

The acidic isoelectric point of IFNT allows for it to be enriched from serum through binding to a strong anion exchanger at pH of 8.2. IFNT was first purified from conceptus secretory proteins by using similar DEAE anion exchange chromotography. In order to achieve a 5-fold enrichment (assuming 100% recovery), 1 ml serum from jugular blood was diluted in 14 ml Tris pH 8.1 in order to obtain final pH of 8.2 for binding to the anion exchange matrix. This buffered and diluted bovine serum was pre-filtered using a 0.45 µm filter (Milipore) and then loaded and centrifuged (500×g; 5 min) through the Pierce Strong Ion Exchange columns (anion exchange) spin column. Proteins with no affinity to the matrix were removed through washing with 10 ml of Tris pH 8.2 and then the columns were loaded with 10 mL of 0.025 M Tris pH 8.2/0.15 M NaCl and spun again. This first salt cut was predicated to not appreciably impact amount of IFNT bound to the column and if this is the case, then future studies will entail loading and washing columns with 0.15 M NaCl. The flow through was collected and the columns were then loaded with 0.025 M Tris pH 8.2/0.3M NaCl and the flow through was collected again, which is predicted to contain IFNT. Finally, the columns were loaded with 0.025 M Tris pH 8.2/2M NaCl and the flow through was collected to ensure complete elution of IFNT. Fractions were then desalted using 3,000 Da columns from Millipore (Amicon ultracentrifuge filter) and resuspended in 200 µl RIA buffer. All collection fractions are stored frozen in preparation for analysis in the IFNT RIA.

Example 3: Detection of IFNT by Mass Spectrometry

Mass spectrometry (MS) is an analytical chemistry technique used to identify the amount and type of materials, chemicals, or compounds present in a sample. A sample is injected into the injection port of the MS device. In a typical MS procedure, a sample, which may be solid, liquid, or gas, is ionized, for example by bombarding it with electrons. This may cause some of the sample's molecules to break into charged fragments. These ions are then separated according to their mass-to-charge ratio, typically by accelerating them and subjecting them to an electric or magnetic field: ions of the same mass-to-charge ratio will undergo the same amount of deflection. The ions are detected by a mechanism capable of detecting charged particles, such as an electron multiplier. Each component, compound, or chemical injected ideally produces a specific spectral peak that may be recorded on a paper chart or electronically. The time elapsed between injection and elution is called the "retention time" which can be used to differentiate between compounds. The size of the peaks is proportional to the quantity of the corresponding substances in the specimen analyzed.

The methods for detecting IFNT by MS were developed using prepared culture media collected from Conceptus and Endometrium tissue cultures. The secreted proteins from each sample (i.e. secretome) were profiled. The proteins collected from uterine flushings were also profiled. Spectral counting and relative quantitation of differentially abundant proteins from 12 hr and 24 hr time points was performed for both Conceptus and Endometrium. These biological samples were used to test the IFNT multiple reaction monitoring (MRM) assay.

Conceptus secretome sample were collected at 12 (1042 Conceptus) or 24 (2752 Conceptus) hours of culturing. The total weight for the 1042 Conceptus culture was approximately 9 mg. The total weigh for the 2752 Conceptus culture was 21 mg. 5 µg of protein obtained from each Conceptus culture was digested with trypsin, and 1 µg of the digested protein was analyzed via chromatography and mass spectrometry. Each sample was injected 2× and run on a standard 90 minute liquid chromatography-gradient.

Biopsied Endometrium specimens were cultured for 12 (1042) or 24 (2752) hours. For the 12 hour cultures, half of a 0.39 g specimen was divided into 3 wells and cultured in DMEM. For the 24 hour cultures, half of a 0.291 specimen was divided into 3 wells and cultured in DMEM. Following culturing, 30 µg of total protein was collected from each culture and digested with trypsin. 1 µg of the digested total protein was analyzed by chromatography and mass spectrometry. Each sample was injected 2× and run on a standard 90 minute liquid chromatography-gradient.

30 µg of total protein from uterine flushings were digested with trypsin. 1 µg of the digested total protein was analyzed by chromatography and mass spectrometry. Each sample was injected 2× and run on a standard 90 minute liquid chromatography-gradient Analysis of the Conceptus secretome identified 412 proteins in total; 229 proteins were identified in the 1042 sample, and 386 were identified in the 2752 sample, with 203 of the identified proteins present in both samples. Analysis of the Endometrium culture secretome identified 390 total proteins; 348 in the 12 hour culture (Sample 1042), and 282 in the 24 hour culture (Sample 2752), with 240 of the identified proteins present in both samples. Analysis of the uterine flushing samples identified 419 total proteins.

Figure 4A:
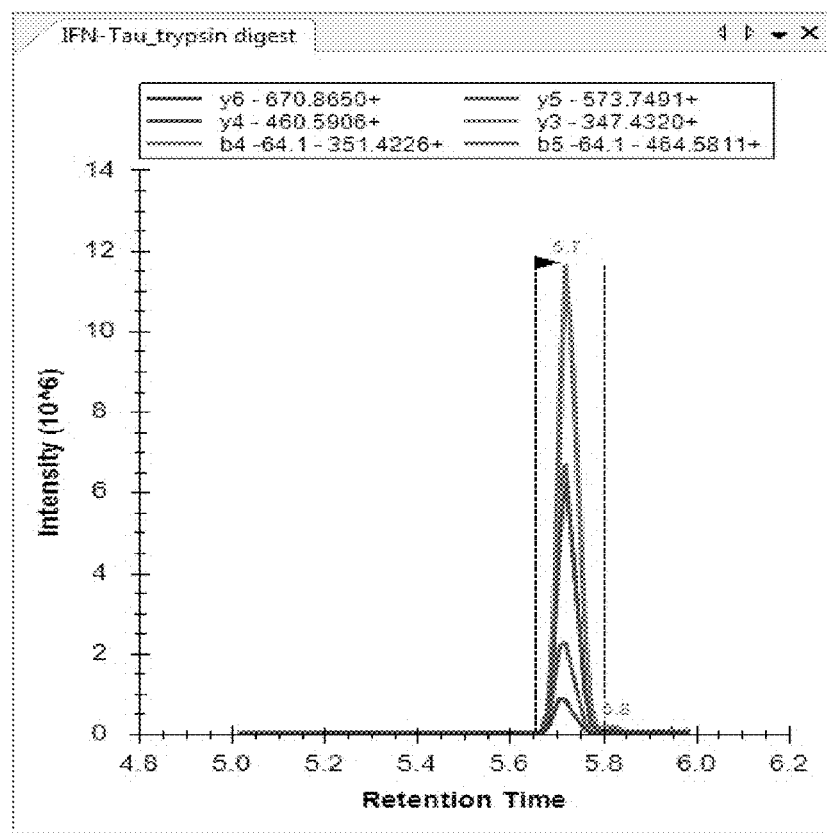
FIG. 4 (A-C) shows GC-MS analysis of three different bovine IFNT peptides (SEQ ID NOS: 11, 17, and 9) (see Table 1).
Figure 4B:
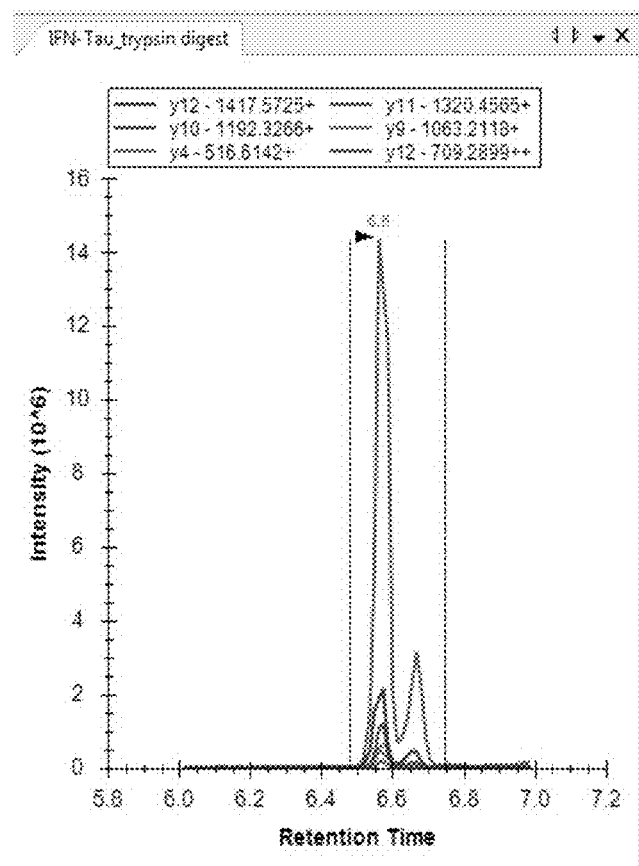
Figure 4C:
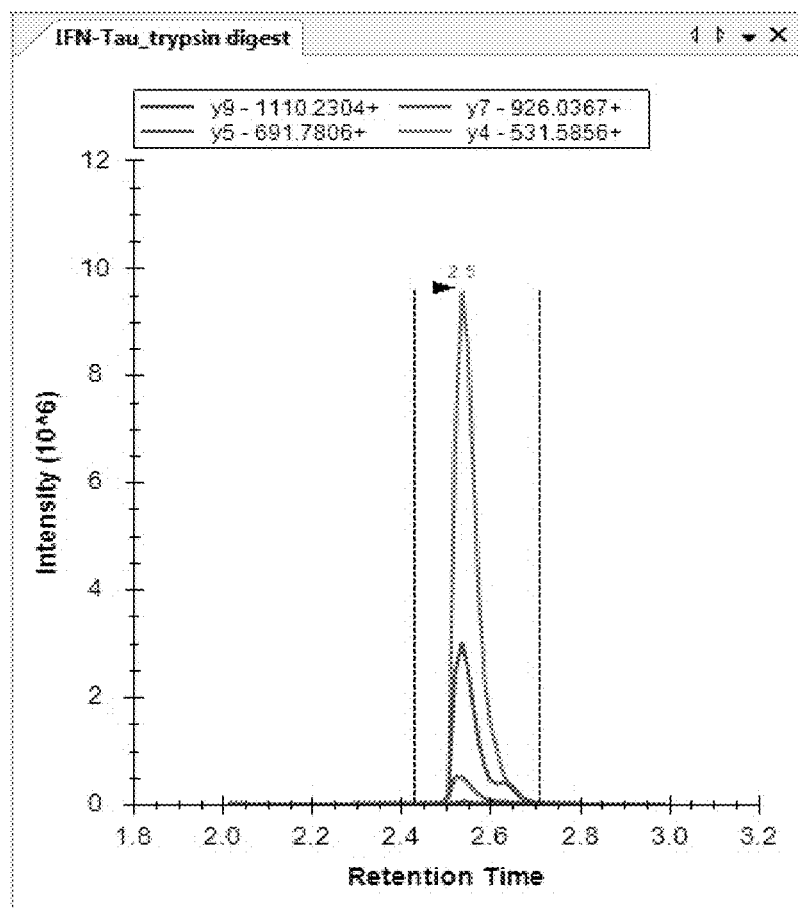
Figure 5A:
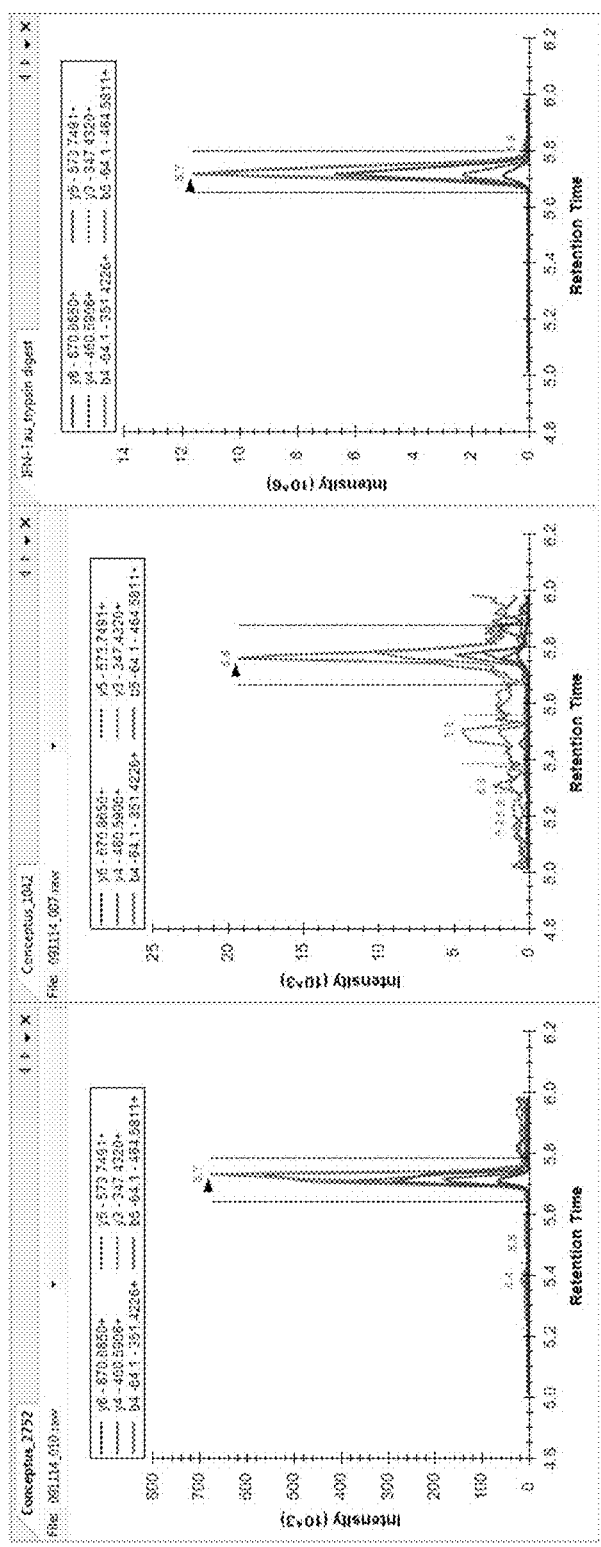
FIG. 5(A-B) shows MS analysis of INFT in conceptus culture filtrate samples. (B) shows quantification of IFNT levels in the samples based on the area of the spectrometric peaks having the specific IFNT retention time.
Figure 5B:
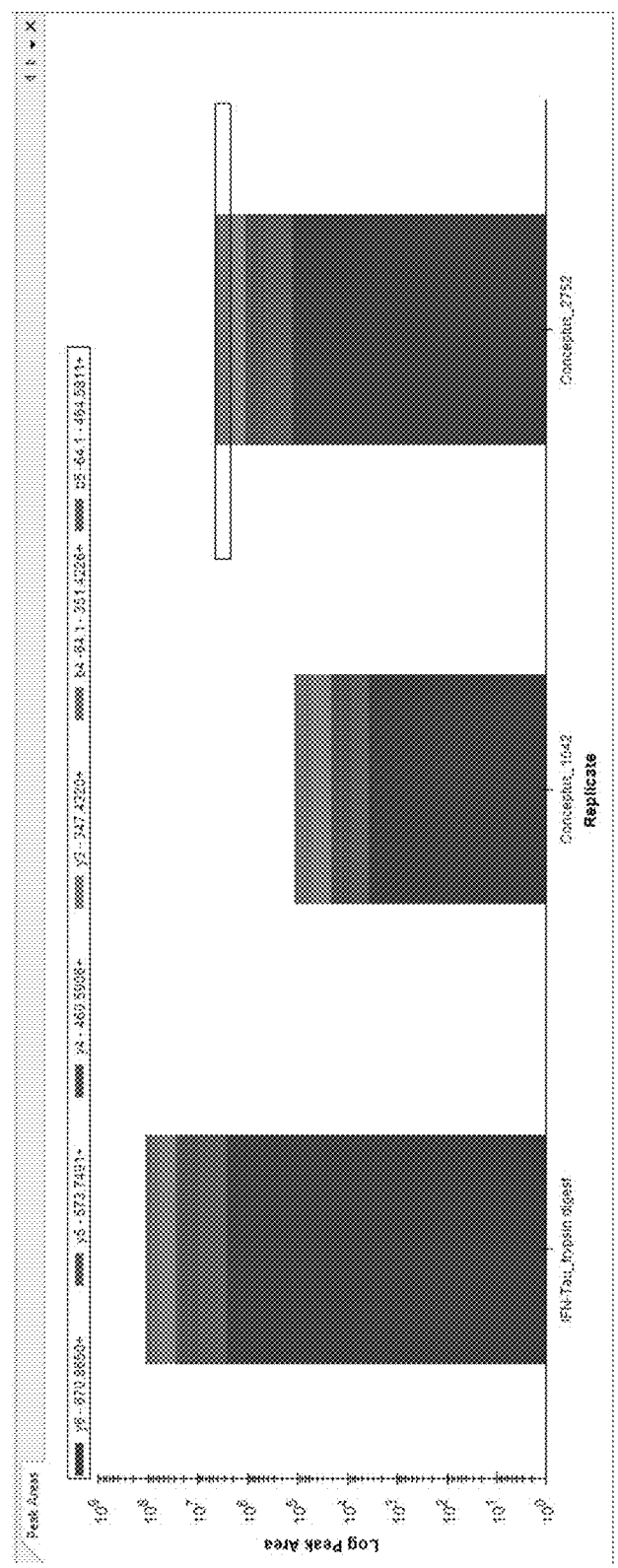

Three different IFNT trypsin digest products—MGPILTVK (SEQ ID NO:11); DFGLPQEMVEGNQLQK (SEQ ID NO:17); and LSPHPCLQDR (SEQ ID NO:9)—were investigated for MS analysis using increasing amounts of each. As shown in FIG. 4, each peptide was identifiable by retention time on the chromatographs. The amount of IFNT in the Conceptus, Endometrium, and uterine flushing samples was analyzed by the MS method, using the peak having a retention time of 5.7 corresponding to the MGPILTVK peptide fragment of IFNT, as shown in FIG. 5A. Based on the size of the peaks, the amount of IFNT in each sample was quantified, as shown in FIG. 5B. The amount of IFNT in the Conceptus culture filtrate was twice as high in the 24 hour sample, as compared to the 12 hour sample, as detected by this assay. These results demonstrate that this MS-based detection method is both specific and sensitive.

REFERENCES

Alberta, J. A., L. F. Epstein, et al. (1989). "Mitochondrial localization of a phosphoprotein that rapidly accumulates in adrenal cortex cells exposed to adrenocorticotropic hormone or to cAMP." J Biol Chem 264(4): 2368-72.

Alila, H. W. and W. Hansel (1984). "Origin of different cell types in the bovine corpus luteum as characterized by specific monoclonal antibodies." Biol Reprod 31(5): 1015-25.

Allison Gray, C., F. F. Bartol, et al. (2000). "Ovine uterine gland knock-out model: effects of gland ablation on the estrous cycle." Biol Reprod 62(2): 448-56.

Anthony, R. V. et al. 1988. Synthesis and processing of ovine trophoblast protein-1 and bovine trophoblast protein-1, conceptus secretory proteins involved in the maternal recognition of pregnancy. Endocrinology 123: 1274-1280.

Antoniazzi, A. Q., B. T. Webb, et al. (2013). "Endocrine delivery of interferon tau protects the corpus luteum from prostaglandin F2 alpha-induced luteolysis in ewes." Biol Reprod 88(6): 144.

Arakane, F., S. R. King, et al. (1997). "Phosphorylation of steroidogenic acute regulatory protein (StAR) modulates its steroidogenic activity." J Biol Chem 272(51): 32656-62.

Armstrong, L. C., B. Bjorkblom, et al. (2002). "Thrombospondin 2 inhibits microvascular endothelial cell proliferation by a caspase-independent mechanism." Mol Biol Cell 13(6): 1893-905.

Arosh, J. A., S. K. Banu, et al. (2004). "Effect of interferon-tau on prostaglandin biosynthesis, transport, and signaling at the time of maternal recognition of pregnancy in cattle: evidence of polycrine actions of prostaglandin E2." Endocrinology 145(11): 5280-93.

Arvisais, E., X. Hou, et al. "Prostaglandin F2alpha represses IGF-I-stimulated IRS1/phosphatidylinositol-3-kinase/AKT signaling in the corpus luteum: role of ERK and P70 ribosomal S6 kinase." Mol Endocrinol 24(3): 632-43.

Ashburner, M., C. A. Ball, et al. (2000). "Gene ontology: tool for the unification of biology. The Gene Ontology Consortium." Nature Genetics 25(1): 25-9.

Ashworth, C. J. and F. W. Bazer (1989). "Changes in ovine conceptus and endometrial function following asynchronous embryo transfer or administration of progesterone." Biol Reprod 40(2): 425-33.

Austin, K. J., B. M. Bany, et al. (2003). "Interferon-stimulated gene-15 (Isg15) expression is up-regulated in the mouse uterus in response to the implanting conceptus." Endocrinology 144(7): 3107-13.

Austin, K. J., A. L. Carr, et al. (2004). "Localization of ISG15 and conjugated proteins in bovine endometrium using immunohistochemistry and electron microscopy." Endocrinology 145(2): 967-75.

Austin, K. J., S. K. Ward, et al. (1996). "Ubiquitin cross-reactive protein is released by the bovine uterus in response to interferon during early pregnancy." Biol Reprod 54(3): 600-6.

Babiychuk, E. B. and A. Draeger (2000). "Annexins in cell membrane dynamics. Ca(2+)-regulated association of lipid microdomains." J Cell Biol 150(5): 1113-24.

Balasubramanian, K., H. A. Lavoie, et al. (1997). "Regulation of porcine granulosa cell steroidogenic acute regulatory protein (StAR) by insulin-like growth factor I: synergism with follicle-stimulating hormone or protein kinase A agonist." Endocrinology 138(1): 433-9.

Banu, S. K., J. A. Arosh, et al. (2005). "Expression of prostaglandin transporter in the bovine uterus and fetal membranes during pregnancy." Biol Reprod 73(2): 230-6.

Barcikowski, B., J. C. Carlson, et al. (1974). "The effect of endogenous and exogenous estradiol-17beta on the release of prostaglandin F2alpha from the ovine uterus." Endocrinology 95(5): 1340-9.

Bauersachs, S., K. Mitko, et al. (2008). "Transcriptome studies of bovine endometrium reveal molecular profiles characteristic for specific stages of estrous cycle and early pregnancy." Exp Clin Endocrinol Diabetes 116(7): 371-84.

Bauersachs, S., S. E. Ulbrich, et al. (2012). "Comparison of the effects of early pregnancy with human interferon, alpha 2 (IFNA2), on gene expression in bovine endometrium." Biol Reprod 86(2): 46.

Bauersachs, S. and E. Wolf (2013). "Immune aspects of embryo-maternal cross-talk in the bovine uterus." J Reprod Immunol 97(1): 20-6.

Bazer, F. W., J. Kim, et al. (2012). "Select nutrients, progesterone, and interferon tau affect conceptus metabolism and development." Ann N Y Acad Sci 1271: 88-96.

Bazer, F. W. and R. M. Roberts (1983). "Biochemical aspects of conceptus-endometrial interactions." J Exp Zool 228(2): 373-83.

Bazer, F. W., J. L. Vallet, R. M. Roberts, D. C. Sharp, and W. W. Thatcher. 1986. Role of conceptus secretory products in establishment of pregnancy. Journal of reproduction and fertility 76: 841-850.

Bazer, F. W., W. W. Thatcher, et al. (1991). "Physiological mechanisms of pregnancy recognition in ruminants." J Reprod Feral Suppl 43: 39-47.

Bazer, F. W., G. Wu, et al. (2010). "Novel pathways for implantation and establishment and maintenance of pregnancy in mammals." Mol Hum Reprod 16(3): 135-52.

Bebington, C., F. J. Doherty, et al. (1999). "Ubiquitin cross-reactive protein gene expression is increased in decidualized endometrial stromal cells at the initiation of pregnancy." Mol Hum Reprod 5(10): 966-72.

Bekisz, J., H. Schmeisser, et al. (2004). "Human interferons alpha, beta and omega." Growth Factors 22(4): 243-51.

Berg, D. K., J. van Leeuwen, et al. (2010). "Embryo loss in cattle between Days 7 and 16 of pregnancy." Theriogenology 73(2): 250-60.

Berisha, B., D. Schams, et al. (2000). "Expression and tissue concentration of vascular endothelial growth factor, its receptors, and localization in the bovine corpus luteum during estrous cycle and pregnancy." Biol Reprod 63(4): 1106-14.

Binelli, M., A. Guzeloglu, et al. (2000). "Interferon-tau modulates phorbol ester-induced production of prostaglandin and expression of cyclooxygenase-2 and phospholipase-A(2) from bovine endometrial cells." Biol Reprod 63(2): 417-24.

Binelli, M., P. Subramaniam, et al. (2001). "Bovine interferon-tau stimulates the Janus kinase-signal transducer and activator of transcription pathway in bovine endometrial epithelial cells." Biol Reprod 64(2): 654-65.

Bittman, E. L. and F. J. Karsch (1984). "Nightly duration of pineal melatonin secretion determines the reproductive response to inhibitory day length in the ewe." Biol Reprod 30(3): 585-93.

Black, S. M., J. A. Harikrishna, et al. (1994). "The mitochondrial environment is required for activity of the cholesterol side-chain cleavage enzyme, cytochrome P450scc." Proc Natl Acad Sci USA 91(15): 7247-51.

Blohm, F., B. Friden, et al. (2008). "A prospective longitudinal population-based study of clinical miscarriage in an urban Swedish population." BJOG 115(2): 176-82; discussion 183.

Bogan, R. L. and G. D. Niswender (2007). "Constitutive steroidogenesis in ovine large luteal cells may be mediated by tonically active protein kinase A." Biol Reprod 77(2): 209-16.

Borner, C. (2003). "The Bcl-2 protein family: sensors and checkpoints for life-or-death decisions." Mol Immunol 39(11): 615-47.

Bott, R. C. et al. 2010. Uterine vein infusion of interferon tau (IFNT) extends luteal life span in ewes. Biology of reproduction 82: 725-735.

Braunschweig, A. and M. Jozsi (2011). "Human pentraxin 3 binds to the complement regulator c4b-binding protein." PLoS One 6(8): e23991.

Bremer, J. (1983). "Carnitine—metabolism and functions." Physiol Rev 63(4): 1420-80.

Bromer, J. G. and E. Seli (2008). "Assessment of embryo viability in assisted reproductive technology: shortcomings of current approaches and the emerging role of metabolomics." Curr Opin Obstet Gynecol 20(3): 234-41.

Budnik, L. T., D. Jahner, et al. (1999). "Inhibitory effects of TNF alpha on mouse tumor Leydig cells: possible role of ceramide in the mechanism of action." Mol Cell Endocrinol 150(1-2): 39-46.

Caffrey, J. L., T. M. Nett, et al. (1979). "Activity of 3beta-hydroxy-delta5-steroid dehydrogenase/delta5-delta4-isomerase in the ovine corpus luteum." Biol Reprod 20(2): 279-87.

Cardinali, D. P. and M. I. Vacas (1987). "Cellular and molecular mechanisms controlling melatonin release by mammalian pineal glands." Cell Mol Neurobiol 7(4): 323-37.

Chapman, L. P., M. J. Epton, et al. (2003). "Evidence for a role of the adenosine 5'-triphosphate-binding cassette transporter A1 in the externalization of annexin I from pituitary folliculo-stellate cells." Endocrinology 144(3): 1062-73.

Charleston, B. and H. J. Stewart (1993). "An interferon-induced Mx protein: cDNA sequence and high-level expression in the endometrium of pregnant sheep." Gene 137(2): 327-31.

Chegini, N., Z. M. Lei, et al. (1991). "Cellular distribution and cycle phase dependency of gonadotropin and eicosanoid binding sites in bovine corpora lutea." Biol Reprod 45(3): 506-13.

Chen, Y. J., Q. Feng, et al. (1999). "Expression of the steroidogenic acute regulatory protein and luteinizing hormone receptor and their regulation by tumor necrosis factor alpha in rat corpora lutea." Biol Reprod 60(2): 419-27.

Christenson, L. K., S. Gunewardena, et al. (2013). "Research resource: preovulatory LH surge effects on follicular theca and granulosa transcriptomes." Mol Endocrinol 27(7): 1153-71.

Chung, P. H., T. W. Sandhoff, et al. (1998). "Hormone and prostaglandin F2 alpha regulation of messenger ribonucleic acid encoding steroidogenic acute regulatory protein in human corpora lutea." Endocrine 8(2): 153-60.

Clark, B. J., J. Wells, et al. (1994). "The purification, cloning, and expression of a novel luteinizing hormone-induced mitochondrial protein in MA-10 mouse Leydig tumor cells. Characterization of the steroidogenic acute regulatory protein (StAR)." J Biol Chem 269(45): 28314-22.

Cohen, T., D. Nahari, et al. (1996). "Interleukin 6 induces the expression of vascular endothelial growth factor." J Biol Chem 271(2): 736-41.

Colles, S. M., J. K. Woodford, et al. (1995). "Cholesterol interaction with recombinant human sterol carrier protein-2." Lipids 30(9): 795-803.

Danet-Desnoyers, G., C. Wetzels, et al. (1994). "Natural and recombinant bovine interferon tau regulate basal and oxytocin-induced secretion of prostaglandins F2 alpha and E2 by epithelial cells and stromal cells in the endometrium." Reprod Fertil Dev 6(2): 193-202.

Danielsen, E. M., B. van Deurs, et al. (2003). " " Nonclassical" secretion of annexin A2 to the lumenal side of the enterocyte brush border membrane." Biochemistry 42(49): 14670-6.

Davis, J. S. and B. R. Rueda (2002). "The corpus luteum: an ovarian structure with maternal instincts and suicidal tendencies." Front Biosci 7: d1949-78.

Davis, T. L., R. C. Bott, et al. (2010). "Progesterone inhibits oxytocin- and prostaglandin F2alpha-stimulated increases in intracellular calcium concentrations in small and large ovine luteal cells." Biol Reprod 82(2): 282-8.

de la Rochebrochard, E. and P. Thonneau (2002). "Paternal age and maternal age are risk factors for miscarriage; results of a multicentre European study." Hum Reprod 17(6): 1649-56.

Deban, L., S. Jaillon, et al. (2010). "Pentraxins in innate immunity: lessons from PTX3." Cell Tissue Res 343(1): 237-49.

Dennis, E. A., S. G. Rhee, et al. (1991). "Role of phospholipase in generating lipid second messengers in signal transduction." FASEB J 5(7): 2068-77.

Diekman, M. A., P. O. O'Callaghan, et al. (1978). "Effect of prostaglandin F2alpha on the number of LH receptors in ovine corpora lutea." Biol Reprod 19(5): 1010-3.

Diekman, M. A., P. O. O'Callaghan, et al. (1978). "Validation of methods and quantification of luteal receptors for LH throughout the estrous cycle and early pregnancy in ewes." Biol Reprod 19(5): 999-1009.

Dinan, L. and R. Lafont (2006). "Effects and applications of arthropod steroid hormones (ecdysteroids) in mammals." J Endocrinol 191(1): 1-8.

Diskin, M. G. and D. G. Morris (2008). "Embryonic and early foetal losses in cattle and other ruminants." Reprod Domest Anim 43 Suppl 2: 260-7.

Diskin, M. G., J. J. Murphy, et al. (2006). "Embryo survival in dairy cows managed under pastoral conditions." Anim Reprod Sci 96(3-4): 297-311.

Dijkhuizen, A. A. 1983. Economic aspects of disease and disease control in dairy cattle. Veterinary Faculty Utrecht, The Netherlands.

Driancourt, M. A., W. R. Gibson, et al. (1985). "Follicular dynamics throughout the oestrous cycle in sheep. A review." Reprod Nutr Dev 25(1A): 1-15.

Dwyer, R. J. and R. B. Church (1979). "Effect of prostaglandin F-2 alpha on ovarian enzyme activity in the hysterectomized guinea-pig." J Reprod Feral 56(1): 85-8.

Dwyer, R. J. and R. B. Church (1979). "Effect of prostaglandin F-2 alpha on plasma levels of progesterone and pregnenolone in the hysterectomized guinea-pig." J Reprod Fertil 56(1): 81-4.

Ellish, N. J., K. Saboda, et al. (1996). "A prospective study of early pregnancy loss." Hum Reprod 11(2): 406-12.

Epstein, L. F. and N. R. Orme-Johnson (1991). "Acute action of luteinizing hormone on mouse Leydig cells: accumulation of mitochondrial phosphoproteins and stimulation of testosterone synthesis." Mol Cell Endocrinol 81(1-3): 113-26.

Epstein, L. F. and N. R. Orme-Johnson (1991). "Regulation of steroid hormone biosynthesis. Identification of precursors of a phosphoprotein targeted to the mitochondrion in stimulated rat adrenal cortex cells." J Biol Chem 266(29): 19739-45.

Esemuede, N., T. Lee, et al. (2004). "The role of thrombospondin-1 in human disease." J Surg Res 122(1): 135-42.

Farin, C. E., C. L. Moeller, et al. (1986). "Morphometric analysis of cell types in the ovine corpus luteum throughout the estrous cycle." Biol Reprod 35(5): 1299-308.

Farkash, Y., R. Timberg, et al. (1986). "Preparation of antiserum to rat cytochrome P-450 cholesterol side chain cleavage, and its use for ultrastructural localization of the immunoreactive enzyme by protein A-gold technique." Endocrinology 118(4): 1353-65.

Faulkner, S., G. Elia, et al. "A comparison of the bovine uterine and plasma proteome using iTRAQ proteomics." Proteomics 12(12): 2014-23.

Faure, A. V., C. Migne, et al. (2002). "Annexin 2 "secretion" accompanying exocytosis of chromaffin cells: possible mechanisms of annexin release." Exp Cell Res 276(1): 79-89.

Ferreira, S. H. and J. R. Vane (1967). "Prostaglandins: their disappearance from and release into the circulation." Nature 216(5118): 868-73.

Fitz, T. A., M. H. Mayan, et al. (1982). "Characterization of two steroidogenic cell types in the ovine corpus luteum." Biol Reprod 27(3): 703-11.

Fleury, A., L. Ducharme, et al. (1998). "In vivo effects of adrenocorticotrophin on the expression of the hamster steroidogenic acute regulatory protein." J Mol Endocrinol 21(2): 131-9.

Flohr, F., S. Schneider-Schaulies, et al. (1999). "The central interactive region of human MxA GTPase is involved in GTPase activation and interaction with viral target structures." FEBS Lett 463(1-2): 24-8.

Flower, R. J. (1988). "Eleventh Gaddum memorial lecture. Lipocortin and the mechanism of action of the glucocorticoids." Br J Pharmacol 94(4): 987-1015.

Flower, R. J. and N. J. Rothwell (1994). "Lipocortin-1: cellular mechanisms and clinical relevance." Trends Pharmacol Sci 15(3): 71-6.

Freund, D. M. and J. E. Prenni (2013). "Improved Detection of Quantitative Differences Using a Combination of Spectral Counting and MS/MS Total Ion Current." J Proteome Res.

Fricke, P. M. (2002). "Scanning the future-ultrasonography as a reproductive management tool for dairy cattle." J Dairy Sci 85(8): 1918-26.

Gao, H., G. Wu, et al. (2009). "Select nutrients in the ovine uterine lumen. I. Amino acids, glucose, and ions in uterine lumenal flushings of cyclic and pregnant ewes." Biol Reprod 80(1): 86-93.

Garlanda, C., V. Maim, et al. (2008). "Inflammatory reaction and implantation: the new entries PTX3 and D6." Placenta 29 Suppl B: 129-34.

Geary, T. W. (2005). "Management strategies to reduce embryonic loss." Proc. Range Beef Cow Symposium XIX. October 3rd (Rapid City, S.D.): 78-87.

Gerke, V., C. E. Creutz, et al. (2005). "Annexins: linking Ca2+ signalling to membrane dynamics." Nat Rev Mol Cell Biol 6(6): 449-61.

Gifford, C. A., K. Racicot, et al. (2007). "Regulation of interferon-stimulated genes in peripheral blood leukocytes in pregnant and bred, nonpregnant dairy cows." J Dairy Sci 90(1): 274-80.

Glass, J. D., T. A. Fitz, et al. (1984). "Cytosolic receptor for estradiol in the corpus luteum of the ewe: variation throughout the estrous cycle and distribution between large and small steroidogenic cell types." Biol Reprod 31(5): 967-74.

Goding, J. R., F. A. Harrison, et al. (1967). "Ovarian activity in the ewe after autotransplantation of the ovary or uterus to the neck." J Physiol 191(2): 129P-130P.

Godkin, J. D., F. W. Bazer, J. Moffatt, F. Sessions, and R. M. Roberts. 1982. Purification and properties of a major, low molecular weight protein released by the trophoblast of sheep blastocysts at day 13-21. Journal of reproduction and fertility 65: 141-150.

Godkin, J. D., F. W. Bazer, and R. M. Roberts. 1984. Ovine trophoblast protein 1, an early secreted blastocyst protein, binds specifically to uterine endometrium and affects protein synthesis. Endocrinology 114: 120-130.

Godkin, J. D., S. E. Smith, et al. (1997). "The role of trophoblast interferons in the maintenance of early pregnancy in ruminants." Am J Reprod Immunol 37(1): 137-43.

Gomez, E., J. N. Caamano, et al. "Embryonic sex induces differential expression of proteins in bovine uterine fluid." J Proteome Res 12(3): 1199-210.

Gray, C. A., C. A. Abbey, et al. (2006). "Identification of endometrial genes regulated by early pregnancy, progesterone, and interferon tau in the ovine uterus." Biol Reprod 74(2): 383-94.

Greenaway, J., J. Lawler, et al. (2007). "Thrombospondin-1 inhibits VEGF levels in the ovary directly by binding and internalization via the low density lipoprotein receptor-related protein-1 (LRP-1)." J Cell Physiol 210(3): 807-18.

Groenendaal, H., D. T. Galligan, and H. A. Mulder. 2004. An economic spreadsheet model to determine optimal breeding and replacement decisions for dairy cattle. J Dairy Sci 87: 2146-2157.

Guo, N., H. C. Krutzsch, et al. (1997). "Thrombospondin 1 and type I repeat peptides of thrombospondin 1 specifically induce apoptosis of endothelial cells." Cancer Res 57(9): 1735-42.

Gupta, K., P. Gupta, et al. (1999). "Binding and displacement of vascular endothelial growth factor (VEGF) by thrombospondin: effect on human microvascular endothelial cell proliferation and angiogenesis." Angiogenesis 3(2): 147-58.

Gupta, S. (2003). "Molecular signaling in death receptor and mitochondrial pathways of apoptosis (Review)." Int J Oncol 22(1): 15-20.

Guthrie, H. D., C. E. Rexroad, Jr., et al. (1979). "In vitro release of progesterone and prostaglandins F and E by porcine luteal and endometrial tissue during induced luteolysis." Adv Exp Med Biol 112: 627-32.

Guzeloglu, A., M. Binelli, et al. (2004). "Inhibition of phorbol ester-induced PGF2alpha secretion by IFN-tau is not through regulation of protein kinase C." Prostaglandins Other Lipid Mediat 74(1-4): 87-99.

Haas, A. L., P. Ahrens, et al. (1987). "Interferon induces a 15-kilodalton protein exhibiting marked homology to ubiquitin." J Biol Chem 262(23): 11315-23.

Han, H., K. J. Austin, L. A. Rempel, and T. R. Hansen. 2006. Low blood ISG15 mRNA and progesterone levels are predictive of non-pregnant dairy cows. The Journal of endocrinology 191: 505-512.

Hansen, P. J., R. V. Anthony, et al. (1985). "In vitro synthesis and secretion of ovine trophoblast protein-1 during the period of maternal recognition of pregnancy." Endocrinology 117(4): 1424-30.

Hansen, T. R., K. J. Austin, et al. (1999). "Mechanism of action of interferon-tau in the uterus during early pregnancy." J Reprod Fertil Suppl 54: 329-39.

Hansen, T. R., L. K. Henkes, et al. (2010). "Endocrine actions of interferon-tau in ruminants." Soc Reprod Fertil Suppl 67: 325-40.

Hansen, T. R., K. Imakawa, et al. (1988). "Interferon RNA of embryonic origin is expressed transiently during early pregnancy in the ewe." J Biol Chem. 263(26): 12801-12804.

Harrison, L. M., N. Kenny, et al. (1987). "Progesterone production, LH receptors, and oxytocin secretion by ovine luteal cell types on days 6, 10 and 15 of the oestrous cycle and day 25 of pregnancy." J Reprod Feral 79(2): 539-48.

Hawkins, D. E., C. J. Belfiore, et al. (1993). "Regulation of messenger ribonucleic acid encoding 3 beta-hydroxysteroid dehydrogenase/delta 5-delta 4 isomerase in the ovine corpus luteum." Biol Reprod 48(5): 1185-90.

Heazell, A. E., M. Brown, et al. (2010). "Review: The effects of oxygen on normal and pre-eclamptic placental tissue—insights from metabolomics." Placenta 32 Suppl 2: S119-24.

Henderson, K. M., R. J. Scaramuzzi, et al. (1977). "Simultaneous infusion of prostaglandin E2 antagonizes the luteolytic action of prostaglandin F2alpha in vivo." J Endocrinol 72(3): 379-83.

Henkes, L. E., B. T. Sullivan, et al. (2008). "Acid sphingomyelinase involvement in tumor necrosis factor alpha-regulated vascular and steroid disruption during luteolysis in vivo." Proc Natl Acad Sci USA 105(22): 7670-5.

Herbert, D., J. Lucke, et al. (2009). "Pregnancy losses in young Australian women: findings from the Australian Longitudinal Study on Women's Health." Womens Health Issues 19(1): 21-9.

Horisberger, M. A., P. Staeheli, et al. (1983). "Interferon induces a unique protein in mouse cells bearing a gene for resistance to influenza virus." Proc Natl Acad Sci USA 80(7): 1910-4.

Hou, X., E. W. Arvisais, et al. (2008). "Prostaglandin F2alpha stimulates the expression and secretion of transforming growth factor B1 via induction of the early growth response 1 gene (EGR1) in the bovine corpus luteum." Mol Endocrinol 22(2): 403-14.

Hoyer, P. B. (1998). "Regulation of luteal regression: the ewe as a model." J Soc Gynecol Investig 5(2): 49-57.

Hoyer, P. B., T. A. Fitz, et al. (1984). "Hormone-independent activation of adenylate cyclase in large steroidogenic ovine luteal cells does not result in increased progesterone secretion." Endocrinology 114(2): 604-8.

Huang, Y., W. A. Border, et al. (2006). "Noninhibitory PAI-1 enhances plasmin-mediated matrix degradation both in vitro and in experimental nephritis." Kidney Int 70(3): 515-22.

Hugentobler, S. A., J. M. Sreenan, et al. "Effects of changes in the concentration of systemic progesterone on ions, amino acids and energy substrates in cattle oviduct and uterine fluid and blood." Reprod Feral Dev 22(4): 684-94.

Huie, J. M., R. R. Magness, et al. (1981). "Effect of chronic ipsilateral or contralateral intrauterine infusion of prostaglandin E1 (PGE1) on luteal function of unilaterally ovariectomized ewes." Prostaglandins 21(6): 945-55.

Humblot, P. (2001). "Use of pregnancy specific proteins and progesterone assays to monitor pregnancy and determine the timing, frequencies and sources of embryonic mortality in ruminants." Theriogenology 56(9): 1417-33.

Imakawa, K. et al. 1987. Interferon-like sequence of ovine trophoblast protein secreted by embryonic trophectoderm. Nature 330: 377-379.

Imakawa, K. et al. 1989. Molecular cloning and characterization of complementary deoxyribonucleic acids corresponding to bovine trophoblast protein-1: a comparison with ovine trophoblast protein-1 and bovine interferon-alpha II. Mol Endocrinol 3: 127-139.

Indiveri, C., V. Iacobazzi, et al. (2011). "The mitochondrial carnitine/acylcarnitine carrier: function, structure and physiopathology." Mol Aspects Med 32(4-6): 223-33.

Inskeep, E. K. and R. L. Butcher (1966). "Local component of utero-ovarian relationships in the ewe." J Anim Sci 25(4): 1164-8.

Inskeep, E. K., W. J. Smutny, et al. (1975). "Effects of intrafollicular injections of prostaglandins in non-pregnant and pregnant ewes." J Anim Sci 41(4): 1098-104.

Irizarry, R. A., B. Hobbs, et al. (2003). "Exploration, normalization, and summaries of high density oligonucleotide array probe level data." Biostatistics 4(2): 249-64.

Jimenez, B., O. V. Volpert, et al. (2000). "Signals leading to apoptosis-dependent inhibition of neovascularization by thrombospondin-1." Nat Med 6(1): 41-8.

Jockusch, B. M., K. Murk, et al. (2007). "The profile of profilins." Rev Physiol Biochem Pharmacol 159: 131-49.

Johnson, G. A., K. J. Austin, et al. (1999). "Endometrial ISG17 mRNA and a related mRNA are induced by interferon-tau and localized to glandular epithelial and stromal cells from pregnant cows." Endocrine 10(3): 243-52.

Johnson, G. A., K. J. Austin, et al. (1998). "Pregnancy and interferon-tau induce conjugation of bovine ubiquitin cross-reactive protein to cytosolic uterine proteins." Biol Reprod 58(4): 898-904.

Johnson, G. A., T. E. Spencer, et al. (2000). "Interferon-tau and progesterone regulate ubiquitin cross-reactive protein expression in the ovine uterus." Biol Reprod 62(3): 622-7.

Johnson, G. A., T. E. Spencer, et al. (1999). "Expression of the interferon tau inducible ubiquitin cross-reactive protein in the ovine uterus." Biol Reprod 61(1): 312-8.

Johnson, G. A., M. D. Stewart, et al. (2001). "Effects of the estrous cycle, pregnancy, and interferon tau on 2',5'-oligoadenylate synthetase expression in the ovine uterus." Biol Reprod 64(5): 1392-9.

Johnson, M., P. Davison, et al. (1972). "Carnitine-dependent oxidation of prostaglandins." J Biol Chem 247(17): 5656-8.

Joyce, M. M., F. J. White, et al. (2005). "Interferon stimulated gene 15 conjugates to endometrial cytosolic proteins and is expressed at the uterine-placental interface throughout pregnancy in sheep." Endocrinology 146(2): 675-84.

Juengel, J. L., J. D. Haworth, et al. (2000). "Effect of dose of prostaglandin F(2alpha) on steroidogenic components and oligonucleosomes in ovine luteal tissue." Biol Reprod 62(4): 1047-51.

Juengel, J. L., T. L. Larrick, et al. (1998). "Luteal expression of steroidogenic factor-1 mRNA during the estrous cycle and in response to luteotropic and luteolytic stimuli in ewes." Endocrine 9(3): 227-32.

Juengel, J. L., B. M. Meberg, et al. (1995). "Hormonal regulation of messenger ribonucleic acid encoding steroidogenic acute regulatory protein in ovine corpora lutea." Endocrinology 136(12): 5423-9.

Kaczan-Bourgois, D., J. P. Salles, et al. (1996). "Increased content of annexin II (p 36) and p 11 in human placenta brush-border membrane vesicles during syncytiotrophoblast maturation and differentiation." Placenta 17(8): 669-76.

Kahn, W., J. Fraunholz, et al. (1990). "[Sonographic diagnosis of early pregnancy in horses, cattle, sheep, goats, swine, dogs and cats. Standard values and limitations]." Berl Munch Tierarztl Wochenschr 103(6): 206-11.

Kall, L., J. D. Storey, et al. (2008). "Assigning significance to peptides identified by tandem mass spectrometry using decoy databases." J Proteome Res 7(1): 29-34.

Kaltenbach, C. C., J. W. Graber, et al. (1968). "Effect of hypophysectomy on the formation and maintenance of corpora lutea in the ewe." Endocrinology 82(4): 753-9.

Karsch, F. J., J. F. Roche, et al. (1971). "Prolonged maintenance of the corpus luteum of the ewe by continuous infusion of luteinizing hormone." Biol Reprod 4(2): 129-36.

Keller, A., A. I. Nesvizhskii, et al. (2002). "Empirical statistical model to estimate the accuracy of peptide identifications made by MS/MS and database search." Anal Chem 74(20): 5383-5392.

Kerban, A., D. Boerboom, et al. (1999). "Human chorionic gonadotropin induces an inverse regulation of steroidogenic acute regulatory protein messenger ribonucleic acid in theca interna and granulosa cells of equine preovulatory follicles." Endocrinology 140(2): 667-74.

Khan, K. M. and D. J. Falcone (1997). "Role of laminin in matrix induction of macrophage urokinase-type plasminogen activator and 92-kDa metalloproteinase expression." J Biol Chem 272(13): 8270-5.

Khanna, A., R. F. Aten, et al. (1995). "Heat shock protein-70 induction mediates luteal regression in the rat." Mol Endocrinol 9(11): 1431-40.

Khaskheli, M., S. Baloch, et al. (2010). "Risk factors in early pregnancy complications." J Coll Physicians Surg Pak 20(11): 744-7.

Kim, J., G. Song, et al. (2013). "Arginine, leucine, and glutamine stimulate proliferation of porcine trophectoderm cells through the MTOR-RPS6K-RPS6-EIF4EBP1 signal transduction pathway." Biol Reprod 88(5): 113.

Kim, J. Y., R. C. Burghardt, et al. (2011). "Select nutrients in the ovine uterine lumen. VII. Effects of arginine, leucine, glutamine, and glucose on trophectoderm cell signaling, proliferation, and migration." Biol Reprod 84(1): 62-9.

Kliem, H., H. Welter, et al. (2007). "Expression and localisation of extracellular matrix degrading proteases and their inhibitors during the oestrous cycle and after induced luteolysis in the bovine corpus luteum." Reproduction 134(3): 535-47.

Koch, J. M., J. Ramadoss, et al. (2010). "Proteomic profile of uterine luminal fluid from early pregnant ewes." J Proteome Res 9(8): 3878-85.

Krikun, G., C. J. Lockwood, et al. (1994). "The expression of the placental anticoagulant protein, annexin V, by villous trophoblasts: immunolocalization and in vitro regulation." Placenta 15(6): 601-12.

Krueger, R. J. and N. R. Orme-Johnson (1983). "Acute adrenocorticotropic hormone stimulation of adrenal corticosteroidogenesis. Discovery of a rapidly induced protein." J Biol Chem 258(16): 10159-67.

LaVoie, H. A., J. C. Garmey, et al. (1999). "Mechanisms of insulin-like growth factor I augmentation of follicle-stimulating hormone-induced porcine steroidogenic acute regulatory protein gene promoter activity in granulosa cells." Endocrinology 140(1): 146-53.

Lawler, J. (2000). "The functions of thrombospondin-1 and -2." Curr Opin Cell Biol 12(5): 634-40.

Leavitt, W. W., W. C. Okulicz, et al. (1985). "Rapid recovery of nuclear estrogen receptor and oxytocin receptor in the ovine uterus following progesterone withdrawal." J Steroid Biochem 22(6): 687-91.

Lee, J., J. A. McCracken, et al. (2012). "Intraluteal prostaglandin biosynthesis and signaling are selectively directed towards PGF2alpha during luteolysis but towards PGE2 during the establishment of pregnancy in sheep." Biol Reprod 87(4): 97.

Lehmann, M. and J. Koolman (1989). "Ecdysteroid receptors of the blowfly Calliphora vicina. Characterization of binding to nonspecific DNA." Eur J Biochem 181(3): 577-82.

Lehoux, J. G., A. Fleury, et al. (1998). "The acute and chronic effects of adrenocorticotropin on the levels of messenger ribonucleic acid and protein of steroidogenic enzymes in rat adrenal in vivo." Endocrinology 139(9): 3913-22.

Lejeune, H., P. Sanchez, et al. (1998). "Time-course effects of human recombinant luteinizing hormone on porcine Leydig cell specific differentiated functions." Mol Cell Endocrinol 144(1-2): 59-69.

Leslie, C. A. and L. Levine (1973). "Evidence for the presence of a prostaglandin E 2-9-keto reductase in rat organs." Biochem Biophys Res Commun 52(3): 717-24.

Lestavel, S. and J. C. Fruchart (1994). "Lipoprotein receptors." Cell Mol Biol (Noisy-le-grand) 40(4): 461-81.

Levasseur, M. C. (1983). "Utero-ovarian relationships in placental mammals: role of uterus and embryo in the regulation of progesterone secretion by the corpus luteum. A review." Reprod Nutr Dev 23(5): 793-816.

Li, J. and R. M. Roberts (1994). "Interferon-tau and interferon-alpha interact with the same receptors in bovine endometrium. Use of a readily iodinatable form of recombinant interferon-tau for binding studies." J Biol Chem 269(18): 13544-50.

Lin, D., T. Sugawara, et al. (1995). "Role of steroidogenic acute regulatory protein in adrenal and gonadal steroidogenesis." Science 267(5205): 1828-31.

Lin, T., J. Hu, et al. (1998). "Interferon-gamma inhibits the steroidogenic acute regulatory protein messenger ribonucleic acid expression and protein levels in primary cultures of rat Leydig cells." Endocrinology 139(5): 2217-22.

Lin, T., D. Wang, et al. (1998). "Upregulation of human chorionic gonadotrophin-induced steroidogenic acute regulatory protein by insulin-like growth factor-I in rat Leydig cells." Endocrine 8(1): 73-8.

Liu, H. B., R. G. Sadygov, et al. (2004). "A model for random sampling and estimation of relative protein abundance in shotgun proteomics." Anal Chem 76(14): 4193-4201.

Liu, X. M., G. L. Ding, et al. (2012). "Down-regulation of S100A11, a calcium-binding protein, in human endometrium may cause reproductive failure." J Clin Endocrinol Metab 97(10): 3672-83.

Liu, Z. and D. M. Stocco (1997). "Heat shock-induced inhibition of acute steroidogenesis in MA-10 cells is associated with inhibition of the synthesis of the steroidogenic acute regulatory protein." Endocrinology 138(7): 2722-8.

Livak, K. J. and T. D. Schmittgen (2001). "Analysis of relative gene expression data using real-time quantitative PCR and the 2(-Delta Delta C(T)) Method." Methods 25(4): 402-8.

Loeb, K. R. and A. L. Haas (1992). "The interferon-inducible 15-kDa ubiquitin homolog conjugates to intracellular proteins." J Biol Chem 267(11): 7806-13.

Luo, L., H. Chen, et al. (1998). "Leydig cell protein synthesis and steroidogenesis in response to acute stimulation by luteinizing hormone in rats." Biol Reprod 59(2): 263-70.

MacLean, J. A., 2nd, R. M. Roberts, et al. (2004). "Atypical Kunitz-type serine proteinase inhibitors produced by the ruminant placenta." Biol Reprod 71(2): 455-63.

Magness, R. R., J. M. Huie, et al. (1981). "Effect of chronic ipsilateral or contralateral intrauterine infusion of prostaglandin E2 (PGE2) on luteal function of unilaterally ovariectomized ewes." Prostaglandins Med 6(4): 389-401.

Mapletoft, R. J., M. R. Del Campo, et al. (1976). "Local venoarterial pathway for uterine-induced luteolysis in cows." Proc Soc Exp Biol Med 153(2): 289-94.

Mapletoft, R. J., D. R. Lapin, et al. (1976). "The ovarian artery as the final component of the local luteotropic pathway between a gravid uterine horn and ovary in ewes." Biol Reprod 15(3): 414-21.

Margosio, B., D. Marchetti, et al. (2003). "Thrombospondin 1 as a scavenger for matrix-associated fibroblast growth factor 2." Blood 102(13): 4399-406.

Maroni, D. and J. S. Davis (2011). "TGFB1 disrupts the angiogenic potential of microvascular endothelial cells of the corpus luteum." J Cell Sci 124(Pt 14): 2501-10.

Masferrer, J. L., S. T. Reddy, et al. (1994). "In vivo glucocorticoids regulate cyclooxygenase-2 but not cyclooxygenase-1 in peritoneal macrophages." J Pharmacol Exp Ther 270(3): 1340-4.

Mauduit, C., F. Gasnier, et al. (1998). "Tumor necrosis factor-alpha inhibits leydig cell steroidogenesis through a decrease in steroidogenic acute regulatory protein expression." Endocrinology 139(6): 2863-8.

McCracken, J. A., J. C. Carlson, et al. (1972). "Prostaglandin F 2 identified as a luteolytic hormone in sheep." Nat New Biol 238(83): 129-34.

McCracken, J. A., E. E. Custer, et al. (1999). "Luteolysis: A Neuroendocrine-Mediated Event." Physiological Reviews 79(2): 263-323.

McCracken, J. A., M. E. Glew, et al. (1970). "Corpus luteum regression induced by prostagland in F2-alpha." J Clin Endocrinol Metab 30(4): 544-6.

McLaughlin, J. N., M. R. Mazzoni, et al. (2005). "Thrombin modulates the expression of a set of genes including thrombospondin-1 in human microvascular endothelial cells." J Biol Chem 280(23): 22172-80.

McPherson, L. A., E. A. Van Kirk, et al. (1993). "Localization of stress protein-70 in ovine corpora lutea during prostaglandin-induced luteolysis." Prostaglandins 46(5): 433-40.

McWaters, P., L. Hurst, et al. (2000). "Characterisation of monoclonal antibodies to ovine interleukin-6 and the development of a sensitive capture ELISA." Vet Immunol Immunopathol 73(2): 155-65.

Meadows, C., P. J. Rajala-Schultz, and G. S. Frazer. 2005. A spreadsheet-based model demonstrating the nonuniform economic effects of varying reproductive performance in Ohio dairy herds. J Dairy Sci 88: 1244-1254.

Menkhorst, E. M., N. Lane, et al. (2012). "Decidual-secreted factors alter invasive trophoblast membrane and secreted proteins implying a role for decidual cell regulation of placentation." PLoS One 7(2): e31418.

Metwally, M., K. J. Ong, et al. (2008). "Does high body mass index increase the risk of miscarriage after spontaneous and assisted conception? A meta-analysis of the evidence." Fertil Steril 90(3): 714-26.

Meyer, M. D., G. D. Desnoyers, et al. (1996). "Treatment with recombinant bovine interferon-tau in utero attenuates secretion of prostaglandin F from cultured endometrial epithelial cells." J Dairy Sci 79(8): 1375-84.

Milvae, R. A. and W. Hansel (1983). "Prostacyclin, prostaglandin F2 alpha and progesterone production by bovine luteal cells during the estrous cycle." Biol Reprod 29(5): 1063-8.

Mirando, M. A., E. C. Short, Jr., et al. (1991). "Stimulation of 2',5'-oligoadenylate synthetase activity in sheep endometrium during pregnancy, by intrauterine infusion of ovine trophoblast protein-1, and by intramuscular administration of recombinant bovine interferon-alpha II." J Reprod Fertil 93(2): 599-607.

Mirochnik, Y., A. Kwiatek, et al. (2008). "Thrombospondin and apoptosis: molecular mechanisms and use for design of complementation treatments." Curr Drug Targets 9(10):851-62.

Mondal, M., B. Schilling, et al. (2011). "Deciphering the luteal transcriptome: potential mechanisms mediating stage-specific luteolytic response of the corpus luteum to prostaglandin F(2)alpha." Physiol Genomics 43(8): 447-56.

Moor, R. M. and L. E. Rowson (1964). "Influence of the Embryo and Uterus on Luteal Function in the Sheep." Nature 201: 522-3.

Moor, R. M. and L. E. Rowson (1966). "The corpus luteum of the sheep: effect of the removal of embryos on luteal function." J Endocrinol 34(4): 497-502.

Moor, R. M. and L. E. Rowson (1966). "The corpus luteum of the sheep: functional relationship between the embryo and the corpus luteum." J Endocrinol 34(2): 233-9.

Moor, R. M. and L. E. Rowson (1966). "Local uterine mechanisms affecting luteal function in the sheep." J Reprod Fertil 11(2): 307-10.

Moore, L. G., V. J. Choy, et al. (1986). "Evidence for the pulsatile release of PGF-2 alpha inducing the release of ovarian oxytocin during luteolysis in the ewe." J Reprod Fertil 76(1): 159-66.

Mosser, G., C. Ravanat, et al. (1991). "Sub-domain structure of lipid-bound annexin-V resolved by electron image analysis." J Mol Biol 217(2): 241-5.

Muller-Newen, G., A. Kuster, et al. (1998). "Soluble IL-6 receptor potentiates the antagonistic activity of soluble gp130 on IL-6 responses." J Immunol 161(11): 6347-55.

Munoz, M., F. J. Corrales, et al. "Proteome of the early embryo-maternal dialogue in the cattle uterus." J Proteome Res 11(2): 751-66.

Murphy, B. D. (2000). "Models of luteinization." Biol Reprod 63(1): 2-11.

Nackley, A. C., W. Shea-Eaton, et al. (2002). "Repression of the steroidogenic acute regulatory gene by the multifunctional transcription factor Yin Yang 1." Endocrinology 143(3): 1085-96.

Naivar, K. A., S. K. Ward, et al. (1995). "Secretion of bovine uterine proteins in response to type I interferons." Biol Reprod 52(4): 848-54.

Narasimhan, J., J. L. Potter, et al. (1996). "Conjugation of the 15-kDa interferon-induced ubiquitin homolog is distinct from that of ubiquitin." J Biol Chem 271(1): 324-30.

Nett, T. M., M. C. McClellan, et al. (1976). "Effects of prostaglandins on the ovine corpus luteum: blood flow, secretion of progesterone and morphology." Biol Reprod 15(1): 66-78.

Nickel, W. (2003). "The mystery of nonclassical protein secretion. A current view on cargo proteins and potential export routes." Eur J Biochem 270(10): 2109-19.

Nigro, G., M. Mazzocco, et al. (2011). "Role of the infections in recurrent spontaneous abortion." J Matern Fetal Neonatal Med 24(8): 983-9.

Nishikawa, T., H. Sasano, et al. (1996). "Regulation of expression of the steroidogenic acute regulatory (StAR) protein by ACTH in bovine adrenal fasciculata cells." Biochem Biophys Res Commun 223(1): 12-8.

Niswender, G. D., L. E. Reichert, Jr., A. R. Midgley, Jr., and A. V. Nalbandov. 1969. Radioimmunoassay for bovine and ovine luteinizing hormone. Endocrinology 84: 1166-1173.

Niswender, G. D. (1973). "Influence of the site of conjugation on the specificity of antibodies to progesterone." Steroids 22(3): 413-24.

Niswender, G. D., T. L. Davis, et al. (2007). "Judge, jury and executioner: the auto-regulation of luteal function." Soc Reprod Feral Suppl 64: 191-206.

Niswender, G. D., J. L. Juengel, et al. (2000). "Mechanisms controlling the function and life span of the corpus luteum." Physiol Rev 80(1): 1-29.

Niswender, G. D., R. T. Moore, et al. (1975). "Flow of blood to the ovaries of ewes throughout the estrous cycle." Biol Reprod 13(4): 381-8.

Nitta, A., K. Shirasuna, et al. (2011). "Possible involvement of IFNT in lymphangiogenesis in the corpus luteum during the maternal recognition period in the cow." Reproduction 142(6): 879-92.

Nor, J. E., R. S. Mitra, et al. (2000). "Thrombospondin-1 induces endothelial cell apoptosis and inhibits angiogenesis by activating the caspase death pathway." J Vasc Res 37(3): 209-18.

O'Shea, J. D., D. G. Cran, et al. (1979). "The small luteal cell of the sheep." J Anat 128(Pt 2): 239-51.

Oehme, I., S. Bosser, et al. (2006). "Agonists of an ecdysone-inducible mammalian expression system inhibit Fas Ligand- and TRAIL-induced apoptosis in the human colon carcinoma cell line RKO." Cell Death Differ 13(2): 189-201.

Okuyama, K. (2008). "Revisiting the molecular structure of collagen." Connect Tissue Res 49(5): 299-310.

Oliveira, J. F. et al. 2008. Expression of interferon (IFN)-stimulated genes in extrauterine tissues during early pregnancy in sheep is the consequence of endocrine IFN-tau release from the uterine vein. Endocrinology 149: 1252-1259.

Olofsson, J. and P. C. Leung (1994). "Auto/paracrine role of prostaglandins in corpus luteum function." Mol Cell Endocrinol 100(1-2): 87-91.

Olofsson, J., E. Norjavaara, et al. (1992). "Synthesis of prostaglandin F2 alpha, E2 and prostacyclin in isolated corpora lutea of adult pseudopregnant rats throughout the luteal life-span." Prostaglandins Leukot Essent Fatty Acids 46(2): 151-61.

Osaki, M., M. Oshimura, et al. (2004). "PI3K-Akt pathway: its functions and alterations in human cancer." Apoptosis 9(6): 667-76.

Otani, N., S. Minami, et al. (1999). "The vascular endothelial growth factor/fms-like tyrosine kinase system in human ovary during the menstrual cycle and early pregnancy." J Clin Endocrinol Metab 84(10): 3845-51.

Ott, T. L., J. Yin, et al. (1998). "Effects of the estrous cycle and early pregnancy on uterine expression of Mx protein in sheep (Ovis aries)." Biol Reprod 59(4): 784-94.

Palade, G. (1975). "Intracellular aspects of the process of protein synthesis." Science 189(4200): 347-58.

Papadopoulos, V., H. Amri, et al. (1997). "Peripheral benzodiazepine receptor in cholesterol transport and steroidogenesis." Steroids 62(1): 21-8.

Papadopoulos, V., H. Amri, et al. (1997). "Targeted disruption of the peripheral-type benzodiazepine receptor gene inhibits steroidogenesis in the R2C Leydig tumor cell line." J Biol Chem 272(51): 32129-35.

Papadopoulos, V. and A. S. Brown (1995). "Role of the peripheral-type benzodiazepine receptor and the polypeptide diazepam binding inhibitor in steroidogenesis." J Steroid Biochem Mol Biol 53(1-6): 103-10.

Paradela, A., S. B. Bravo, et al. (2005). "Proteomic analysis of apical microvillous membranes of syncytiotrophoblast cells reveals a high degree of similarity with lipid rafts." J Proteome Res 4(6): 2435-41.

Pate, J. L. (1988). "Regulation of prostaglandin synthesis by progesterone in the bovine corpus luteum." Prostaglandins 36(3): 303-15.

Patek, C. E. and J. Watson (1976). "Prostaglandin F and progesterone secretion by porcine endometrium and corpus luteum in vitro." Prostaglandins 12(1): 97-111.

Perretti, M. and R. J. Flower (2004). "Annexin 1 and the biology of the neutrophil." J Leukoc Biol 76(1): 25-9.

Perretti, M. and F. N. Gavins (2003). "Annexin 1: an endogenous anti-inflammatory protein." News Physiol Sci 18: 60-4.

Perry, D. J., K. J. Austin, et al. (1999). "Cloning of interferon-stimulated gene 17: the promoter and nuclear proteins that regulate transcription." Mol Endocrinol 13(7): 1197-206.

Pescador, N., A. Houde, et al. (1997). "Follicle-stimulating hormone and intracellular second messengers regulate steroidogenic acute regulatory protein messenger ribonucleic acid in luteinized porcine granulosa cells." Biol Reprod 57(3): 660-8.

Peterson, A. J., H. R. Tervit, et al. (1976). "Jugular levels of 13, 14-dihydro-15-keto-prostaglandin F and progesterone around luteolysis and early pregnancy in the ewe." Prostaglandins 12(4): 551-8.

Pitcher, P. M., and D. T. Galligan. 1990. Decision analysis and economic evaluation of the use of the rapid milk progesterone assay for early detection of pregnancy status of cows. J Am Vet Med Assoc 197: 1586-1590.

Piper, P. J., J. R. Vane, et al. (1970). "Inactivation of prostaglandins by the lungs." Nature 225(5233): 600-4.

Plaizier, J. C., G. J. King, J. C. Dekkers, and K. Lissemore. 1997. Estimation of economic values of indices for reproductive performance in dairy herds using computer simulation. J Dairy Sci 80: 2775-2783.

Plante, C. et al. 1990. Purification of bovine trophoblast protein-1 complex and quantification of its microheterogeneous variants as affected by culture conditions. Journal of reproductive immunology 18: 271-291.

Pletneva, L. M., O. Haller, et al. (2006). "Interferon-inducible Mx gene expression in cotton rats: cloning, characterization, and expression during influenza viral infection." J Interferon Cytokine Res 26(12): 914-21.

Pon, L. A., L. F. Epstein, et al. (1986). "Acute cAMP stimulation in Leydig cells: rapid accumulation of a protein similar to that detected in adrenal cortex and corpus luteum." Endocr Res 12(4): 429-46.

Pon, L. A., J. A. Hartigan, et al. (1986). "Acute ACTH regulation of adrenal corticosteroid biosynthesis. Rapid accumulation of a phosphoprotein." J Biol Chem 261(28): 13309-16.

Pon, L. A. and N. R. Orme-Johnson (1986). "Acute stimulation of steroidogenesis in corpus luteum and adrenal cortex by peptide hormones. Rapid induction of a similar protein in both tissues." J Biol Chem 261(14): 6594-9.

Pon, L. A. and N. R. Orme-Johnson (1988). "Acute stimulation of corpus luteum cells by gonadotrophin or adenosine 3',5'-monophosphate causes accumulation of a phosphoprotein concurrent with acceleration of steroid synthesis." Endocrinology 123(4): 1942-8.

Pratt, B. R., R. L. Butcher, et al. (1977). "Antiluteolytic effect of the conceptus and of PGE2 in ewes." J Anim Sci 45(4): 784-91.

Pru, J. K., M. P. Lynch, et al. (2003). "Signaling mechanisms in tumor necrosis factor alpha-induced death of microvascular endothelial cells of the corpus luteum." Reprod Biol Endocrinol 1: 17.

Pru, J. K., B. R. Rueda, et al. (2001). "Interferon-tau suppresses prostaglandin F2alpha secretion independently of the mitogen-activated protein kinase and nuclear factor kappa B pathways." Biol Reprod 64(3): 965-73.

Rand, J. H. (2000). "The pathogenic role of annexin-V in the antiphospholipid syndrome." Curr Rheumatol Rep 2(3): 246-51.

Ravizza, T., D. Moneta, et al. (2001). "Dynamic induction of the long pentraxin PTX3 in the CNS after limbic seizures: evidence for a protective role in seizure-induced neurodegeneration." Neuroscience 105(1): 43-53.

Rege, T. A., J. Stewart, Jr., et al. (2009). "Thrombospondin-1-induced apoptosis of brain microvascular endothelial cells can be mediated by TNF-R1." J Cell Physiol 218(1): 94-103.

Rempel, L. A., B. R. Francis, et al. (2005). "Isolation and sequence of an interferon-tau-inducible, pregnancy- and bovine interferon-stimulated gene product 15 (ISG15)-specific, bovine ubiquitin-activating E1-like (UBE1L) enzyme." Biol Reprod 72(2): 365-72.

Ren, B., K. O. Yee, et al. (2006). "Regulation of tumor angiogenesis by thrombospondin-1." Biochim Biophys Acta 1765(2): 178-88.

Rexroad, C. E., Jr. and H. D. Guthrie (1979). "Prostaglandin F2 alpha and progesterone release in vitro by ovine luteal tissue during induced luteolysis." Adv Exp Med Biol 112: 639-44.

Reynolds, L. P., J. Stigler, et al. (1981). "Effect of PGE1 on PGF2 alpha-induced luteolysis in nonbred ewes." Prostaglandins 21(6): 957-72.

Rintala-Dempsey, A. C., A. Rezvanpour, et al. (2008). "S100-annexin complexes-structural insights." FEBS J 275(20): 4956-66.

Roberts, R. M. (1989). "Conceptus interferons and maternal recognition of pregnancy." Biol Reprod 40(3): 449-52.

Roberts, R. M., Y. Chen, et al. (2008). "Interferons and the maternal-conceptus dialog in mammals." Seminars in Cell & Developmental Biology 19(2): 170-177.

Roberts, R. M., J. C. Cross, et al. (1992). "Interferons as hormones of pregnancy." Endocr Rev 13(3): 432-52.

Roberts, R. M., S. Xie, et al. (1996). "Maternal recognition of pregnancy." Biol Reprod 54(2): 294-302.

Rocchetti, T. T., C. Marconi, et al. (2010). "Group B streptococci colonization in pregnant women: risk factors and evaluation of the vaginal flora." Arch Gynecol Obstet 283(4): 717-21.

Romero, J. J., A. Q. Antoniazzi, et al. (2013). "Pregnancy-associated genes contribute to antiluteolytic mechanisms in ovine corpus luteum." Physiol Genomics.

Rovere, P., G. Peri, et al. (2000). "The long pentraxin PTX3 binds to apoptotic cells and regulates their clearance by antigen-presenting dendritic cells." Blood 96(13): 4300-6.

Rueda, B. R., K. A. Naivar, et al. (1993). "Recombinant interferon-tau regulates secretion of two bovine endometrial proteins." J. Interferon Res. 13(4): 303-309.

Saeed, S. A. and A. C. Roy (1972). "Purification of 15-hydroxy prostaglandin dehydrogenase from bovine lung." Biochem Biophys Res Commun 47(1): 96-102.

Salio, M., S. Chimenti, et al. (2008). "Cardioprotective function of the long pentraxin PTX3 in acute myocardial infarction." Circulation 117(8): 1055-64.

Samuel, C. E. (2001). "Antiviral Actions of Interferons." American Society for Microbiology 14(4): 778-809.

Sandhoff, T. W. and M. P. McLean (1996). "Prostaglandin F2alpha reduces steroidogenic acute regulatory (StAR) protein messenger ribonucleic acid expression in the rat ovary." Endocrine 5(2): 183-90.

Sandhoff, T. W. and M. P. McLean (1999). "Repression of the rat steroidogenic acute regulatory (StAR) protein gene by PGF2alpha is modulated by the negative transcription factor DAX-1." Endocrine 10(1): 83-91.

Sartorius, U., I. Schmitz, et al. (2001). "Molecular mechanisms of death-receptor-mediated apoptosis." Chembiochem 2(1): 20-9.

Sawyer, H. R., K. D. Niswender, et al. (1990). "Nuclear changes in ovine luteal cells in response to PGF2 alpha." Domest Anim Endocrinol 7(2): 229-37.

Schalue-Francis, T. K., P. W. Farin, et al. (1991). "Effect of injected bovine interferon-alpha I1 on estrous cycle length and pregnancy success in sheep." J Reprod Fertil 91(1): 347-56.

Schmitt, R. A., R. D. Geisert, et al. (1993). "Uterine cellular changes in 2',5'-oligoadenylate synthetase during the bovine estrous cycle and early pregnancy." Biol Reprod 48(3): 460-6.

Schmittgen, T. D. and K. J. Livak (2008). "Analyzing real-time PCR data by the comparative C(T) method." Nat Protoc 3(6): 1101-8.

Searle, B. C., M. Turner, et al. (2008). "Improving sensitivity by probabilistically combining results from multiple MS/MS search methodologies." J Proteome Res 7(1): 245-253.

Senger, P. L. (2003). Pathways to Pregnancy and Parturition. Pullman, Current Concepts Inc.

Sharma, M., R. T. Ownbey, et al. (2010). "Breast cancer cell surface annexin II induces cell migration and neoangiogenesis via tPA dependent plasmin generation." Exp Mol Pathol 88(2): 278-86.

Shu, F., M. Sugimura, et al. (2000). "Immunohistochemical study of annexin V expression in placentae of preeclampsia." Gynecol Obstet Invest 49(1): 17-23.

Shutt, D. A., A. H. Clarke, et al. (1976). "Changes in concentration of prostaglandin F and steroids in human corpora lutea in relation to growth of the corpus luteum and luteolysis." J Endocrinol 71(3): 453-4.

Silva, P. J., J. L. Juengel, et al. (2000). "Prostaglandin metabolism in the ovine corpus luteum: catabolism of prostaglandin F(2alpha) (PGF(2alpha)) coincides with resistance of the corpus luteum to PGF(2alpha)." Biol Reprod 63(5): 1229-36.

Silvia, W. J. and G. D. Niswender (1984). "Maintenance of the corpus luteum of early pregnancy in the ewe. III. Differences between pregnant and nonpregnant ewes in luteal responsiveness to prostaglandin F2 alpha." J Anim Sci 59(3): 746-53.

Silvia, W. J. and G. D. Niswender (1986). "Maintenance of the corpus luteum of early pregnancy in the ewe. IV. Changes in luteal sensitivity to prostaglandin F2 alpha throughout early pregnancy." J Anim Sci 63(4): 1201-7.

Smith, G. W., P. C. Gentry, et al. (1997). "Control of extracellular matrix remodelling within ovarian tissues: localization and regulation of gene expression of plasminogen activator inhibitor type-1 within the ovine corpus luteum." J Reprod Feral 110(1): 107-14.

Smith, G. W., P. C. Gentry, et al. (1996). "Ontogeny and regulation of luteinizing hormone receptor messenger ribonucleic acid within the ovine corpus luteum." Biol Reprod 54(1): 76-83.

Smith, M. F., E. W. McIntush, et al. (1994). "Mechanisms associated with corpus luteum development." J Anim Sci 72(7): 1857-72.

Smith, W. L. (1992). "Prostanoid biosynthesis and mechanisms of action." Am J Physiol 263(2 Pt 2): F181-91.

Smyth, G. K. (2004). "Linear models and empirical bayes methods for assessing differential expression in microarray experiments." Stat Appl Genet Mol Biol 3: Article3.

Song, G., F. W. Bazer, et al. (2007). "Pregnancy and interferon tau regulate RSAD2 and IFIH1 expression in the ovine uterus." Reproduction 133(1): 285-95.

Song, G., J. A. Fleming, et al. (2011). "Pregnancy and interferon tau regulate DDX58 and PLSCR1 in the ovine uterus during the peri-implantation period." Reproduction 141(1): 127-38.

Spencer, T. E. and F. W. Bazer (1995). "Temporal and spatial alterations in uterine estrogen receptor and progesterone receptor gene expression during the estrous cycle and early pregnancy in the ewe." Biology of Reproduction 53(6): 1527-1543.

Spencer, T. E. and F. W. Bazer (1996). "Ovine interferon tau suppresses transcription of the estrogen receptor and oxytocin receptor genes in the ovine endometrium." Endocrinology 137(3): 1144-7.

Spencer, T. E., W. C. Becker, et al. (1995). "Ovine interferon-tau inhibits estrogen receptor up-regulation and estrogen-induced luteolysis in cyclic ewes." Endocrinology 136(11): 4932-44.

Spencer, T. E., R. C. Burghardt, et al. (2004). "Conceptus signals for establishment and maintenance of pregnancy." Anim Reprod Sci 82-83: 537-50.

Spencer, T. E., N. Forde, et al. (2013). "Conceptus-derived prostaglandins regulate gene expression in the endometrium prior to pregnancy recognition in ruminants." Reproduction 146(4): 377-87.

Spencer, T. E., N. H. Ing, et al. (1995). "Intrauterine injection of ovine interferon-tau alters oestrogen receptor and oxytocin receptor expression in the endometrium of cyclic ewes." J Mol Endocrinol 15(2): 203-20.

Spencer, T. E., G. A. Johnson, et al. (2004). "Implantation mechanisms: insights from the sheep." Reproduction 128 (6): 657-68.

Spencer, T. E., T. L. Ott, et al. (1996). "tau-Interferon: pregnancy recognition signal in ruminants." Proc Soc Exp Biol Med 213(3): 215-29.

Spencer, T. E., A. G. Stagg, et al. (1999). "Differential effects of intrauterine and subcutaneous administration of recombinant ovine interferon tau on the endometrium of cyclic ewes." Biol Reprod 61(2): 464-70.

Staggs, K. L., K. J. Austin, et al. (1998). "Complex induction of bovine uterine proteins by interferon-tau." Biol Reprod 59(2): 293-7.

Stein, B. and M. X. Yang (1995). "Repression of the interleukin-6 promoter by estrogen receptor is mediated by NF-kappa B and C/EBP beta." Mol Cell Biol 15(9): 4971-9.

Strandberg, E., Oltenacu, P. A. 1989. Economic consequences of different calving intervals. ACTA Agric Scand 39: 407-420.

Stocco, C., C. Telleria, et al. (2007). "The molecular control of corpus luteum formation, function, and regression." Endocr Rev 28(1): 117-49.

Stocco, C. O., L. F. Lau, et al. (2002). "A calcium/calmodulin-dependent activation of ERK1/2 mediates JunD phosphorylation and induction of nur77 and 20alpha-hsd genes by prostaglandin F2alpha in ovarian cells." J Biol Chem 277(5): 3293-302.

Stocco, D. M. (2001). "StAR protein and the regulation of steroid hormone biosynthesis." Annu Rev Physiol 63: 193-213.

Stocco, D. M. and B. J. Clark (1996). "Regulation of the acute production of steroids in steroidogenic cells." Endocr Rev 17(3): 221-44.

Sugawara, T., D. Lin, et al. (1995). "Structure of the human steroidogenic acute regulatory protein (StAR) gene: StAR stimulates mitochondrial cholesterol 27-hydroxylase activity." Biochemistry 34(39): 12506-12.

Swanston, I. A., K. P. McNatty, et al. (1977). "Concentration of prostaglandin F2alpha and steroids in the human corpus luteum." J Endocrinol 73(1): 115-22.

Takahashi, H. et al. 2005. Establishment of a specific radioimmunoassay for bovine interferon tau. Theriogenology 63:1050-1060.

Tait, J. F., M. Sakata, et al. (1988). "Placental anticoagulant proteins: isolation and comparative characterization four members of the lipocortin family." Biochemistry 27(17): 6268-76.

Taniguchi, T. and A. Takaoka (2002). "The interferon-alpha/beta system in antiviral responses: a multimodal machinery of gene regulation by the IRF family of transcription factors." Curr Opin Immunol 14(1): 111-6.

Teixeira, M. G., K. J. Austin, et al. (1997). "Bovine granulocyte chemotactic protein-2 is secreted by the endometrium in response to interferon-tau (IFN-tau)." Endocrine 6(1): 31-7.

Telleria, C. M., J. Ou, et al. (1998). "The expression of interleukin-6 in the pregnant rat corpus luteum and its regulation by progesterone and glucocorticoid." Endocrinology 139(8): 3597-605.

Temmerman, M., M. I. Lopita, et al. (1992). "The role of maternal syphilis, gonorrhoea and HW-1 infections in spontaneous abortion." Int J STD AIDS 3(6): 418-22.

Toyokawa, K., S. J. Carling, et al. (2007). "Cellular localization and function of the antiviral protein, ovine Mx1 (oMx1): I. Ovine Mx1 is secreted by endometrial epithelial cells via an 'unconventional' secretory pathway." Am J Reprod Immunol 57(1): 13-22.

Toyokawa, K., F. Leite, et al. (2007). "Cellular localization and function of the antiviral protein, ovine Mx1 (oMx1): II. The oMx1 protein is a regulator of secretion in an ovine glandular epithelial cell line." Am J Reprod Immunol 57(1): 23-33.

Tuckey, R. C. (1992). "Cholesterol side-chain cleavage by mitochondria from the human placenta. Studies using hydroxycholesterols as substrates." J Steroid Biochem Mol Biol 42(8): 883-90.

Tuckey, R. C. and H. C. Atkinson (1989). "Pregnenolone synthesis from cholesterol and hydroxycholesterols by mitochondria from ovaries following the stimulation of immature rats with pregnant mare's serum gonadotropin and human choriogonadotropin." Eur J Biochem 186(1-2): 255-9.

Vinatier, D., P. Dufour, et al. (1996). "Apoptosis: a programmed cell death involved in ovarian and uterine physiology." Eur J Obstet Gynecol Reprod Biol 67(2): 85-102.

Voges, D., R. Berendes, et al. (1994). "Three-dimensional structure of membrane-bound annexin V. A correlative electron microscopy-X-ray crystallography study." J Mol Biol 238(2): 199-213.

Vorsanova, S. G., A. D. Kolotii, et al. (2005). "Evidence for high frequency of chromosomal mosaicism in spontaneous abortions revealed by interphase FISH analysis." J Histochem Cytochem 53(3): 375-80.

Wang, X., B. Campos, et al. (1999). "Annexin V is critical in the maintenance of murine placental integrity." Am J Obstet Gynecol 180(4): 1008-16.

Wang, X., L. P. Walsh, et al. (1999). "The role of arachidonic acid on LH-stimulated steroidogenesis and steroidogenic acute regulatory protein accumulation in MA-10 mouse Leydig tumor cells." Endocrine 10(1): 7-12.

Watson, E. D. and P. L. Sertich (1990). "Secretion of prostaglandins and progesterone by cells from corpora lutea of mares." J Reprod Fertil 88(1): 223-9.

Watson, J., T. S. Shepherd, et al. (1979). "Prostaglandin E-2-9-ketoreductase in ovarian tissues." J Reprod Fertil 57(2): 489-96.

Wiltbank, M. C., C. J. Belfiore, et al. (1993). "Steroidogenic enzyme activity after acute activation of protein kinase (PK) A and PKC in ovine small and large luteal cells." Mol Cell Endocrinol 97(1-2): 1-7.

Wiltbank, M. C., P. B. Guthrie, et al. (1989). "Hormonal regulation of free intracellular calcium concentrations in small and large ovine luteal cells." Biol Reprod 41(4): 771-8.

Wiltbank, M. C. and J. S. Ottobre (2003). "Regulation of intraluteal production of prostaglandins." Reprod Biol Endocrinol 1: 91.

Yamada, O., J. Todoroki, et al. (2002). "The dynamic expression of extracellular matrix in the bovine endometrium at implantation." J Vet Med Sci 64(3): 207-14.

Yan, G. R., W. Ding, et al. (2011). "Characterization of phosphoproteins in gastric cancer secretome." OMICS 15(1-2): 83-90.

Yankey, S. J., B. A. Hicks, et al. (2001). "Expression of the antiviral protein Mx in peripheral blood mononuclear cells of pregnant and bred, non-pregnant ewes." J Endocrinol 170(2): R7-11.

Yarmola, E. G. and M. R. Bubb (2009). "How depolymerization can promote polymerization: the case of actin and profilin." Bioessays 31(11): 1150-60.

Zalman, Y., E. Klipper, et al. (2012). "Regulation of angiogenesis-related prostaglandin f2alpha-induced genes in the bovine corpus luteum." Biol Reprod 86(3): 92.

Zarco, L., G. H. Stabenfeldt, et al. (1988). "Modification of prostaglandin F-2 alpha synthesis and release in the ewe during the initial establishment of pregnancy." J Reprod Fertil 83(2): 527-36.

Zarco, L., G. H. Stabenfeldt, et al. (1988). "Release of prostaglandin F-2 alpha and the timing of events associated with luteolysis in ewes with oestrous cycles of different lengths." J Reprod Fertil 83(2): 517-26.

Zelinski, M. B., D. P. Selivonchick, et al. (1988). "Characterization of plasma membrane lipids and luteinizing hormone receptors of ovine corpora lutea during luteolysis and early pregnancy." Biol Reprod 38(4): 768-79.

Zeth, K. and M. Thein "Porins in prokaryotes and eukaryotes: common themes and variations." Biochem J 431(1): 13-22.

Zheng, L., K. Foley, et al. "Tyrosine 23 phosphorylation-dependent cell-surface localization of annexin A2 is required for invasion and metastases of pancreatic cancer." PLoS One 6(4): e19390.

Zhu, Y., W. L. Yin, et al. (2012). "Transforming growth factor-1 promotes the transcriptional activation of plasminogen activator inhibitor type 1 in carcinoma-associated fibroblasts." Mol Med Rep 6(5): 1001-5.

What is claimed is:

1. A method for ascertaining pregnancy in a ruminant comprising:
    breeding said ruminant;
    obtaining a sample from said ruminant, wherein said sample is peripheral blood, serum, or plasma;
    detecting whether interferon tau (IFNT) is present in said sample;
    diagnosing the ruminant as pregnant if IFNT was determined to be present in said sample or as not pregnant (NP) if IFNT was determined not to be present in said sample; and performing additional breeding of ruminant determined to be NP.

2. The method of claim 1 wherein said detecting is performed by contacting the sample with a purified antibody specific for IFNT and detecting whether binding occurs between said antibody and IFNT.

3. The method of claim 2 wherein said detecting is accomplished by a colormetric or flourocolormetric assay.

4. The method of claim 2 wherein said detecting is accomplished by radioimmunoassay.

5. The method of claim 2 wherein said detecting is accomplished by ELISA.

6. The method of claim 2 wherein said detecting is accomplished by a dipstick test.

7. The method of claim 2 wherein said detecting is accomplished by a lateral flow assay.

8. The method of claim 1 wherein said determining is accomplished by mass spectroscopy.

9. The method of claim 8 wherein said mass spectrometry detects one or more peptides corresponding to SEQ ID NQ: 9, 11, and 17.

10. The method of claim 1 wherein said ruminant is a cow.

11. The method of claim 1 wherein said ruminant is a sheep.

12. The method of claim 1 wherein said sample is obtained from the ruminant less than 18 days after breeding.

13. The method of claim 1 wherein the collection of said sample is timed to correspond to the predicted production of IFNT by a conceptus produced by said breeding.

14. The method of claim 13 wherein said sample is collected less than 21 days after breeding.

15. The method of claim 13 wherein said sample is collected between day 16 and day 21 after breeding.

* * * * *

```
                         SEQUENCE LISTING

<160> NUMBER OF SEQ ID NOS: 53

<210> SEQ ID NO 1
<211> LENGTH: 195
<212> TYPE: PRT
<213> ORGANISM: Bos taurus

<400> SEQUENCE: 1

Met Ala Phe Val Leu Ser Leu Leu Met Ala Leu Val Leu Val Ser Tyr
1               5                   10                  15

Gly Pro Gly Arg Ser Leu Gly Cys Tyr Leu Ser Glu Asp His Met Leu
            20                  25                  30

Gly Ala Arg Glu Asn Leu Arg Leu Leu Ala Arg Met Asn Arg Leu Ser
        35                  40                  45

Pro His Pro Cys Leu Gln Asp Arg Lys Asp Phe Gly Leu Pro Gln Glu
    50                  55                  60

Met Val Glu Gly Ser Gln Leu Gln Lys Asp Gln Ala Ile Ser Val Leu
65                  70                  75                  80

His Glu Met Leu Gln Gln Cys Phe Asn Leu Phe His Ile Glu His Ser
                85                  90                  95

Ser Ala Ala Trp Asn Thr Thr Leu Leu Glu Gln Leu Cys Thr Gly Leu
```

```
            100                 105                 110
Gln Gln Gln Leu Glu Asp Leu Asp Ala Cys Leu Gly Pro Val Met Gly
            115                 120                 125

Glu Lys Asp Ser Asp Met Gly Arg Met Gly Pro Ile Leu Thr Val Lys
        130                 135                 140

Lys Tyr Phe Gln Asp Ile His Val Tyr Leu Lys Glu Lys Glu Tyr Ser
145                 150                 155                 160

Asp Cys Ala Trp Glu Ile Ile Arg Val Glu Met Met Arg Ala Leu Ser
                165                 170                 175

Ser Ser Thr Thr Leu Gln Lys Arg Leu Arg Lys Met Gly Gly Asp Leu
            180                 185                 190

Asn Ser Leu
        195

<210> SEQ ID NO 2
<211> LENGTH: 1073
<212> TYPE: DNA
<213> ORGANISM: Bos taurus

<400> SEQUENCE: 2
ctgaaggttc acccagaccc catctcagcc agcccagcag cagccacatc ttccccatgg    60
ccttcgtgct ctctctactg atggccctgg tgctggtcag ctacggcccg ggacgatctc   120
tgggttgtta cctgtctgag gaccacatgc taggtgccag ggagaacctc aggctcctgg   180
cccgaatgaa cagactctct cctcatccct gtctgcagga cagaaaagac tttggtcttc   240
ctcaggagat ggtggagggc agccagctcc agaaggatca ggctatctct gtgctccacg   300
agatgctcca gcagtgcttc aacctcttcc acatagagca ctcgtctgct gcctggaaca   360
ccaccctcct ggagcagctc tgcactgggc tccaacagca gctggaggac ctggacgcct   420
gcctgggccc agtgatggga gagaaggact ctgacatggg aaggatgggc cccattctga   480
ctgtgaagaa gtacttccag acatccatgt ctacctgaa agaaaaggaa tacagtgact   540
gcgcctggga aatcatcaga gtggagatga tgagagccct ctcttcatca accaccttgc   600
aaaaaaggtt aagaaagatg ggtggagatc tgaactcact tgagatgac tctcgctgac   660 taagatgcca catcaccttc gtacactcac ctgtgttcat ttcagaagac tctgatttct   720
gcttcagcca ccgaattcat tgaattactt tagccgatac tttgtcagca gtaataagca   780
agtagatata aaagtactca gctgtagggg catgagtcct taagtgatgc ctgccctgat   840
gttatctgtt gttgatttat gtattccttc ttgcatctaa catacttaaa atattaggat   900
atttgtaaag ttacatttca tttgtacatc tattaaaatt tctaaaacat gtttaccatt   960
ttgtgttatt aaatttgtcc tttgttctat ttattaaatc aaagaaaatg agtttcttta  1020
ctcaaaaact ttattattat tattaaaact ttattaaaga aaaaaaaaa aaa          1073

<210> SEQ ID NO 3
<211> LENGTH: 195
<212> TYPE: PRT
<213> ORGANISM: Ovis aries

<400> SEQUENCE: 3

Met Ala Phe Val Leu Ser Leu Leu Met Ala Leu Val Leu Val Ser Tyr
1               5                   10                  15

Gly Pro Gly Gly Ser Leu Gly Cys Tyr Leu Ser Arg Lys Leu Met Leu
            20                  25                  30

Asp Ala Arg Glu Asn Leu Lys Leu Leu Asp Arg Met Asn Arg Leu Ser
```

```
            35                  40                  45
Pro His Ser Cys Leu Gln Asp Arg Lys Asp Phe Gly Leu Pro Gln Glu
    50                  55                  60

Met Val Glu Gly Asp Gln Leu Gln Lys Asp Gln Ala Phe Pro Val Leu
65                  70                  75                  80

Tyr Glu Met Leu Gln Gln Ser Phe Asn Leu Phe Tyr Thr Glu His Ser
                85                  90                  95

Ser Ala Ala Trp Asp Thr Thr Leu Leu Glu Gln Leu Cys Thr Gly Leu
            100                 105                 110

Gln Gln Gln Leu Asp His Leu Asp Thr Cys Arg Gly Gln Val Met Gly
        115                 120                 125

Glu Glu Asp Ser Glu Leu Gly Asn Met Asp Pro Ile Val Thr Val Lys
    130                 135                 140

Lys Tyr Phe Gln Gly Ile Tyr Asp Tyr Leu Gln Glu Lys Gly Tyr Ser
145                 150                 155                 160

Asp Cys Ala Trp Glu Ile Val Arg Val Glu Met Met Arg Ala Leu Thr
                165                 170                 175

Val Ser Thr Thr Leu Gln Lys Arg Leu Thr Lys Met Gly Gly Asp Leu
            180                 185                 190

Asn Ser Pro
    195

<210> SEQ ID NO 4
<211> LENGTH: 519
<212> TYPE: DNA
<213> ORGANISM: Ovis aries

<400> SEQUENCE: 4
tgttacctat ctcggaaact catgctggat gccagggaga acctcaggct cctggaccga      60
atgaacagac tgtcacctca ttcctgtctg caggacagaa aagactttgg tcttccccag     120
gagatggtgg agggcgacca gctccagaag gaccaggcct tctctgtgct ctacgagatg     180
ctccagcaga gcttcaacgt cttccacaca gagcgctcct ctgctgcctg aacaccacc     240 ctcctggagc agctctgcac tggactccaa cagcagctgg accacctgga cacctgcagg     300
ggtcccgtga tgggagagga agactctgaa ctgggtaaca tggaccccat tgtgaccgtg     360
aagaagtact ccagggcat ccatgactac ctgcaagaga agggatacag cgactgcgcc      420
tgggaaatcg tcagagtcga tgatgagag ccctcactt catcaaccac cttgcaaaaa      480
aggttaacaa agatgggtgg agatctgaac tcaccttga                            519

<210> SEQ ID NO 5
<211> LENGTH: 4
<212> TYPE: PRT
<213> ORGANISM: Bos taurus

<400> SEQUENCE: 5

Glu Asn Leu Arg
1

<210> SEQ ID NO 6
<211> LENGTH: 4
<212> TYPE: PRT
<213> ORGANISM: Ovis aries

<400> SEQUENCE: 6

Leu Leu Asp Arg
1
```

<210> SEQ ID NO 7
<211> LENGTH: 4
<212> TYPE: PRT
<213> ORGANISM: Bos taurus

<400> SEQUENCE: 7

Leu Leu Ala Arg
1

<210> SEQ ID NO 8
<211> LENGTH: 13
<212> TYPE: PRT
<213> ORGANISM: Ovis aries

<400> SEQUENCE: 8

Met Asn Arg Pro Ser Pro His Ser Cys Leu Gln Asp Arg
1               5                   10

<210> SEQ ID NO 9
<211> LENGTH: 10
<212> TYPE: PRT
<213> ORGANISM: Bos taurus

<400> SEQUENCE: 9

Leu Ser Pro His Pro Cys Leu Gln Asp Arg
1               5                   10

<210> SEQ ID NO 10
<211> LENGTH: 8
<212> TYPE: PRT
<213> ORGANISM: Ovis aries

<400> SEQUENCE: 10

Met Asp Pro Ile Val Thr Val Lys
1               5

<210> SEQ ID NO 11
<211> LENGTH: 8
<212> TYPE: PRT
<213> ORGANISM: Bos taurus

<400> SEQUENCE: 11

Met Gly Pro Ile Leu Thr Val Lys
1               5

<210> SEQ ID NO 12
<211> LENGTH: 12
<212> TYPE: PRT
<213> ORGANISM: Ovis aries

<400> SEQUENCE: 12

Tyr Phe Gln Gly Ile His Asp Tyr Leu Gln Glu Lys
1               5                   10

<210> SEQ ID NO 13
<211> LENGTH: 10
<212> TYPE: PRT
<213> ORGANISM: Bos taurus

<400> SEQUENCE: 13

Tyr Phe Gln Gly Ile His Val Tyr Leu Lys
1               5                   10

```
<210> SEQ ID NO 14
<211> LENGTH: 5
<212> TYPE: PRT
<213> ORGANISM: Bos taurus

<400> SEQUENCE: 14

Val Glu Met Met Arg
1               5

<210> SEQ ID NO 15
<211> LENGTH: 9
<212> TYPE: PRT
<213> ORGANISM: Ovis aries

<400> SEQUENCE: 15

Ala Leu Thr Ser Ser Thr Thr Leu Lys
1               5

<210> SEQ ID NO 16
<211> LENGTH: 10
<212> TYPE: PRT
<213> ORGANISM: Bos taurus

<400> SEQUENCE: 16

Ala Leu Ser Ser Ser Thr Thr Leu Gln Lys
1               5                   10

<210> SEQ ID NO 17
<211> LENGTH: 16
<212> TYPE: PRT
<213> ORGANISM: Bos taurus

<400> SEQUENCE: 17

Asp Phe Gly Leu Pro Gln Glu Met Val Glu Gly Asn Gln Leu Gln Lys
1               5                   10                  15

<210> SEQ ID NO 18
<211> LENGTH: 195
<212> TYPE: PRT
<213> ORGANISM: Bos taurus

<400> SEQUENCE: 18

Met Ala Phe Val Leu Ser Leu Leu Met Ala Leu Val Leu Val Ser Tyr
1               5                   10                  15

Gly Pro Gly Arg Ser Leu Gly Cys Tyr Leu Ser Glu Asp His Met Leu
                20                  25                  30

Gly Ala Arg Glu Asn Leu Arg Leu Leu Ala Arg Met Asn Arg Leu Ser
            35                  40                  45

Pro His Pro Cys Leu Gln Asp Arg Lys Asp Phe Gly Leu Pro Gln Glu
        50                  55                  60

Met Val Glu Gly Asn Gln Leu Gln Lys Asp Gln Ala Ile Ser Val Leu
65                  70                  75                  80

His Glu Met Leu Gln Gln Cys Leu Asn Leu Phe Tyr Thr Glu His Ser
                85                  90                  95

Ser Ala Ala Trp Asn Thr Thr Leu Leu Glu Gln Leu Cys Thr Gly Leu
                100                 105                 110

Gln Gln Gln Leu Glu Asp Leu Asp Ala Cys Leu Gly Pro Val Met Gly
            115                 120                 125

Glu Lys Asp Ser Asp Met Gly Arg Met Gly Pro Ile Leu Thr Val Lys
        130                 135                 140

Lys Tyr Phe Gln Gly Ile His Val Tyr Leu Lys Glu Lys Glu Tyr Ser
```

```
145                 150                 155                 160
Asp Cys Ala Trp Glu Ile Ile Arg Val Glu Met Met Arg Ala Leu Ser
                165                 170                 175
Ser Ser Thr Thr Leu Gln Lys Arg Leu Arg Lys Met Gly Gly Asp Leu
                180                 185                 190
Asn Ser Leu
        195

<210> SEQ ID NO 19
<211> LENGTH: 195
<212> TYPE: PRT
<213> ORGANISM: Bos taurus

<400> SEQUENCE: 19

Met Ala Phe Val Leu Ser Leu Leu Met Ala Leu Val Leu Val Ser Tyr
1               5                   10                  15
Gly Pro Gly Arg Ser Leu Gly Cys Tyr Leu Ser Glu Asp His Met Leu
                20                  25                  30
Gly Ala Arg Glu Asn Leu Arg Leu Leu Ala Arg Met Asn Arg Leu Ser
                35                  40                  45
Pro His Pro Cys Leu Gln Asp Arg Lys Asp Phe Gly Leu Pro Gln Glu
        50                  55                  60
Met Val Glu Gly Ser Gln Leu Gln Lys Asp Gln Ala Ile Ser Val Leu
65                  70                  75                  80
His Glu Met Leu Gln Gln Cys Phe Asn Leu Phe His Ile Glu His Ser
                85                  90                  95
Ser Ala Ala Trp Asn Thr Thr Leu Leu Glu Gln Leu Cys Thr Gly Leu
                100                 105                 110
Gln Gln Gln Leu Glu Asp Leu Asp Ala Cys Leu Gly Pro Val Met Gly
                115                 120                 125
Glu Lys Asp Ser Asp Met Gly Arg Met Gly Pro Ile Leu Thr Val Lys
        130                 135                 140
Lys Tyr Phe Gln Asp Ile His Val Tyr Leu Lys Glu Lys Glu Tyr Ser
145                 150                 155                 160
Asp Cys Ala Trp Glu Ile Ile Arg Val Glu Met Met Arg Ala Leu Ser
                165                 170                 175
Ser Ser Thr Thr Leu Gln Lys Arg Leu Arg Lys Met Gly Gly Asp Leu
                180                 185                 190
Asn Ser Leu
        195

<210> SEQ ID NO 20
<211> LENGTH: 172
<212> TYPE: PRT
<213> ORGANISM: Bos taurus

<400> SEQUENCE: 20

Cys Tyr Leu Ser Glu Asp His Met Leu Gly Ala Arg Glu Asn Leu Arg
1               5                   10                  15
Leu Leu Ala Arg Met Asn Arg Leu Ser Pro His Pro Cys Leu Gln Asp
                20                  25                  30
Arg Lys Asp Phe Gly Leu Pro Gln Glu Met Val Glu Gly Ser Gln Leu
                35                  40                  45
Gln Lys Asp Gln Ala Ile Ser Val Leu His Glu Met Leu Gln Gln Cys
        50                  55                  60
Phe Asn Leu Phe His Ile Glu His Ser Ser Ala Ala Trp Asn Thr Thr
```

```
65                  70                  75                  80
Leu Leu Glu Gln Leu Cys Thr Gly Leu Gln Gln Gln Leu Glu Asp Leu
                85                  90                  95

Asp Ala Cys Leu Gly Pro Val Met Gly Glu Lys Asp Ser Asp Met Gly
            100                 105                 110

Arg Met Gly Pro Ile Leu Thr Val Lys Lys Tyr Phe Gln Gly Ile His
        115                 120                 125

Val Tyr Leu Lys Glu Lys Glu Tyr Ser Asp Cys Ala Trp Glu Ile Ile
    130                 135                 140

Arg Val Glu Met Met Arg Ala Leu Ser Ser Thr Thr Leu Gln Lys
145                 150                 155                 160

Arg Leu Arg Lys Met Gly Gly Asp Leu Asn Ser Leu
                165                 170

<210> SEQ ID NO 21
<211> LENGTH: 172
<212> TYPE: PRT
<213> ORGANISM: Bos taurus

<400> SEQUENCE: 21

Cys Tyr Leu Ser Glu Asp His Met Leu Gly Ala Arg Glu Asn Leu Arg
1               5                   10                  15

Leu Leu Ala Arg Met Asn Arg Leu Ser Pro His Pro Cys Leu Gln Asp
                20                  25                  30

Arg Lys Asp Phe Gly Leu Pro Gln Glu Met Val Glu Gly Asn Gln Leu
            35                  40                  45

Gln Lys Asp Gln Ala Ile Ser Val Leu His Glu Met Leu Gln Gln Cys
        50                  55                  60

Phe Asn Leu Phe His Ile Glu His Ser Ser Ala Ala Trp Asn Thr Thr
65                  70                  75                  80

Leu Leu Glu Gln Leu Cys Thr Gly Leu Gln Gln Gln Leu Glu Asp Leu
                85                  90                  95

Asp Ala Cys Leu Gly Pro Val Met Gly Glu Lys Asp Ser Asp Met Gly
            100                 105                 110

Arg Met Gly Pro Ile Leu Thr Val Lys Lys Tyr Phe Gln Asp Ile His
        115                 120                 125

Val Tyr Leu Lys Glu Lys Glu Tyr Ser Asp Cys Ala Trp Glu Ile Ile
    130                 135                 140

Arg Val Glu Met Met Arg Ala Leu Ser Ser Ser Thr Thr Leu Gln Lys
145                 150                 155                 160

Arg Leu Arg Lys Met Gly Gly Asp Leu Asn Ser Leu
                165                 170

<210> SEQ ID NO 22
<211> LENGTH: 172
<212> TYPE: PRT
<213> ORGANISM: Bos taurus

<400> SEQUENCE: 22

Cys Tyr Leu Ser Glu Asp His Met Leu Gly Ala Arg Glu Asn Leu Arg
1               5                   10                  15

Leu Leu Ala Arg Met Asn Arg Leu Ser Pro His Pro Cys Leu Gln Asp
                20                  25                  30

Arg Lys Asp Phe Gly Leu Pro Gln Glu Met Val Glu Gly Asn Gln Leu
            35                  40                  45

Gln Lys Asp Gln Ala Ile Ser Val Leu His Glu Met Leu Gln Gln Cys
```

```
                    50                  55                  60
Leu Asn Leu Phe Tyr Thr Glu His Ser Ser Ala Ala Trp Asn Thr Thr
 65                  70                  75                  80

Leu Leu Glu Gln Leu Cys Thr Gly Leu Gln Gln Gln Leu Glu Asp Leu
                 85                  90                  95

Asp Ala Cys Leu Gly Pro Val Met Gly Glu Lys Asp Ser Asp Met Gly
            100                 105                 110

Arg Met Gly Pro Ile Leu Thr Val Lys Lys Tyr Phe Gln Asp Ile His
        115                 120                 125

Val Tyr Leu Lys Glu Lys Glu Tyr Ser Asp Cys Ala Trp Glu Ile Ile
    130                 135                 140

Arg Val Glu Met Met Arg Ala Leu Ser Ser Ser Thr Thr Leu Gln Lys
145                 150                 155                 160

Arg Leu Arg Lys Met Gly Gly Asp Leu Asn Ser Leu
                165                 170

<210> SEQ ID NO 23
<211> LENGTH: 172
<212> TYPE: PRT
<213> ORGANISM: Bos taurus

<400> SEQUENCE: 23

Cys Tyr Leu Ser Glu Asp His Met Leu Gly Ala Arg Glu Asn Leu Arg
  1               5                  10                  15

Leu Leu Ala Arg Met Asn Arg Leu Ser Pro His Pro Cys Leu Gln Asp
                 20                  25                  30

Arg Lys Asp Phe Gly Leu Pro Gln Glu Met Val Glu Gly Asn Gln Leu
            35                  40                  45

Gln Lys Asp Gln Ala Ile Ser Val Leu His Glu Met Leu Gln Gln Cys
    50                  55                  60

Phe Asn Leu Phe Tyr Thr Glu His Ser Ser Ala Ala Trp Asn Thr Thr
 65                  70                  75                  80

Leu Leu Glu Gln Leu Cys Thr Gly Leu Gln Gln Gln Leu Glu Asp Leu
                 85                  90                  95

Asp Ala Cys Leu Gly Pro Val Met Gly Glu Lys Asp Ser Asp Met Gly
            100                 105                 110

Arg Met Gly Pro Ile Leu Thr Val Lys Lys Tyr Phe Gln Asp Ile His
        115                 120                 125

Val Tyr Leu Lys Glu Lys Glu Tyr Ser Asp Cys Ala Trp Glu Ile Ile
    130                 135                 140

Arg Val Glu Met Met Arg Ala Leu Ser Ser Ser Thr Thr Leu Gln Lys
145                 150                 155                 160

Arg Leu Arg Lys Met Gly Gly Asp Leu Asn Ser Leu
                165                 170

<210> SEQ ID NO 24
<211> LENGTH: 172
<212> TYPE: PRT
<213> ORGANISM: Bos taurus

<400> SEQUENCE: 24

Cys Tyr Leu Ser Glu Asp His Met Leu Gly Ala Arg Glu Asn Leu Arg
  1               5                  10                  15

Leu Leu Ala Arg Met Asn Arg Leu Ser Pro His Pro Cys Leu Gln Asp
                 20                  25                  30

Arg Lys Asp Phe Gly Leu Pro Gln Glu Met Val Glu Gly Ser Gln Leu
```

```
                    35                  40                  45
Gln Lys Asp Gln Ala Ile Ser Val Leu His Glu Met Leu Gln Gln Cys
 50                  55                  60

Leu Asn Leu Phe Tyr Thr Glu His Ser Ser Ala Ala Trp Asn Thr Thr
 65                  70                  75                  80

Leu Leu Glu Gln Leu Cys Thr Gly Leu Gln Gln Leu Glu Asp Leu
                 85                  90                  95

Asp Ala Cys Leu Gly Pro Val Met Gly Glu Lys Asp Ser Asp Met Gly
                100                 105                 110

Arg Met Gly Pro Ile Leu Thr Val Lys Lys Tyr Phe Gln Gly Ile His
                115                 120                 125

Val Tyr Leu Lys Glu Lys Glu Tyr Ser Asp Cys Ala Trp Glu Ile Ile
                130                 135                 140

Arg Val Glu Met Met Arg Ala Leu Ser Ser Thr Thr Leu Gln Lys
145                 150                 155                 160

Arg Leu Arg Lys Met Gly Gly Asp Leu Asn Ser Leu
                165                 170

<210> SEQ ID NO 25
<211> LENGTH: 172
<212> TYPE: PRT
<213> ORGANISM: Bos taurus

<400> SEQUENCE: 25

Cys Tyr Leu Ser Glu Asp His Met Leu Gly Ala Arg Glu Asn Leu Arg
  1               5                  10                  15

Leu Leu Ala Arg Met Asn Arg Leu Ser Pro His Pro Cys Leu Gln Asp
                 20                  25                  30

Arg Lys Asp Phe Gly Leu Pro Gln Glu Met Val Glu Gly Asn Gln Leu
                 35                  40                  45

Gln Lys Asp Gln Ala Ile Ser Val Leu His Glu Met Leu Gln Gln Cys
 50                  55                  60

Leu Asn Leu Phe Tyr Thr Glu His Ser Ser Ala Ala Trp Asn Thr Thr
 65                  70                  75                  80

Leu Leu Glu Gln Leu Cys Thr Gly Leu Gln Gln Leu Glu Asp Leu
                 85                  90                  95

Asp Ala Cys Leu Gly Pro Val Met Gly Glu Lys Asp Ser Asp Met Gly
                100                 105                 110

Arg Met Gly Pro Ile Leu Thr Val Lys Lys Tyr Phe Gln Gly Ile His
                115                 120                 125

Val Tyr Leu Lys Glu Lys Glu Tyr Ser Asp Cys Ala Trp Glu Ile Ile
                130                 135                 140

Arg Met Glu Met Met Arg Ala Leu Ser Ser Thr Thr Leu Gln Lys
145                 150                 155                 160

Arg Leu Arg Lys Met Gly Gly Asp Leu Asn Ser Leu
                165                 170

<210> SEQ ID NO 26
<211> LENGTH: 172
<212> TYPE: PRT
<213> ORGANISM: Bos taurus

<400> SEQUENCE: 26

Cys Tyr Leu Ser Glu Asp His Met Leu Gly Ala Arg Glu Asn Leu Arg
  1               5                  10                  15

Leu Leu Ala Arg Met Asn Arg Leu Ser Pro His Pro Cys Leu Gln Asp
```

```
                    20                  25                  30
Arg Lys Asp Phe Gly Leu Pro Gln Glu Met Val Glu Gly Ser Pro Leu
                35                  40                  45

Gln Lys Asp Gln Ala Ile Ser Val Leu His Glu Met Leu Gln Gln Cys
            50                  55                  60

Phe Asn Leu Phe His Ile Glu His Ser Ser Ala Ala Trp Asn Thr Thr
65                  70                  75                  80

Leu Leu Glu Gln Leu Cys Thr Gly Leu Gln Gln Gln Leu Glu Asp Leu
                    85                  90                  95

Asp Ala Cys Leu Gly Pro Val Met Gly Glu Lys Asp Ser Asp Met Gly
                100                 105                 110

Arg Met Gly Pro Ile Leu Thr Val Lys Lys Tyr Phe Gln Gly Ile His
                115                 120                 125

Val Tyr Leu Lys Glu Lys Glu Tyr Ser Asp Cys Ala Trp Glu Ile Ile
                130                 135                 140

Arg Met Glu Met Met Arg Ala Leu Ser Ser Thr Thr Leu Gln Lys
145                 150                 155                 160

Arg Leu Arg Lys Met Gly Gly Asp Leu Asn Ser Leu
                165                 170

<210> SEQ ID NO 27
<211> LENGTH: 172
<212> TYPE: PRT
<213> ORGANISM: Bos taurus

<400> SEQUENCE: 27

Cys Tyr Leu Ser Glu Asp His Met Leu Gly Ala Arg Glu Asn Leu Arg
1               5                   10                  15

Leu Leu Ala Arg Met Asn Arg Leu Ser Pro His Pro Cys Leu Gln Asp
                20                  25                  30

Arg Lys Asp Phe Gly Leu Pro Gln Glu Met Val Glu Gly Asn Gln Leu
                35                  40                  45

Gln Lys Asp Gln Ala Ile Ser Val Leu His Glu Met Leu Gln Gln Cys
            50                  55                  60

Phe Asn Leu Phe Tyr Thr Glu His Ser Ser Ala Ala Trp Asn Thr Thr
65                  70                  75                  80

Leu Leu Glu Gln Leu Cys Thr Gly Leu Gln Gln Gln Leu Glu Asp Leu
                    85                  90                  95

Asp Ala Cys Leu Gly Pro Val Met Gly Glu Lys Asp Ser Asp Met Gly
                100                 105                 110

Arg Met Gly Pro Ile Leu Thr Val Lys Lys Tyr Phe Gln Gly Ile His
                115                 120                 125

Val Tyr Leu Lys Glu Lys Glu Tyr Ser Asp Cys Ala Trp Glu Ile Ile
                130                 135                 140

Arg Thr Glu Met Met Arg Ala Leu Ser Ser Thr Thr Leu Gln Lys
145                 150                 155                 160

Arg Leu Arg Lys Met Gly Gly Asp Leu Asn Ser Leu
                165                 170

<210> SEQ ID NO 28
<211> LENGTH: 172
<212> TYPE: PRT
<213> ORGANISM: Bos taurus

<400> SEQUENCE: 28

Cys Tyr Leu Ser Glu Asp His Met Leu Gly Ala Arg Glu Asn Leu Arg
```

```
1               5                   10                  15
Leu Leu Ala Arg Met Asn Arg Leu Ser Pro His Pro Cys Leu Gln Asp
            20                  25                  30

Arg Lys Asp Phe Gly Leu Pro Gln Glu Met Val Glu Gly Asn Gln Leu
            35                  40                  45

Gln Lys Asp Gln Ala Ile Ser Val Leu His Glu Met Leu Gln Gln Cys
            50                  55                  60

Phe Asn Leu Phe Tyr Thr Glu His Ser Ser Ala Ala Trp Asn Thr Thr
65                  70                  75                  80

Leu Leu Glu Gln Pro Cys Thr Gly Leu Gln Gln Gln Leu Glu Asp Leu
                    85                  90                  95

Asp Ala Cys Leu Gly Pro Val Met Gly Glu Lys Asp Ser Asp Met Gly
            100                 105                 110

Arg Met Gly Pro Ile Leu Thr Val Lys Lys Tyr Phe Gln Gly Ile His
            115                 120                 125

Val Tyr Leu Lys Glu Lys Glu Tyr Ser Asp Cys Ala Trp Glu Ile Ile
            130                 135                 140

Arg Met Glu Met Met Arg Ala Leu Ser Ser Thr Thr Leu Gln Lys
145                 150                 155                 160

Arg Leu Arg Lys Met Gly Gly Asp Leu Asn Ser Leu
            165                 170
```

<210> SEQ ID NO 29
<211> LENGTH: 80
<212> TYPE: PRT
<213> ORGANISM: Bos taurus

<400> SEQUENCE: 29

```
Met Ala Phe Val Leu Ser Leu Leu Met Ala Leu Val Leu Val Ser Tyr
1               5                   10                  15

Gly Pro Gly Arg Ser Leu Gly Cys Tyr Leu Ser Glu Asp His Met Leu
            20                  25                  30

Gly Ala Arg Glu Asn Leu Arg Leu Leu Ala Arg Met Asn Arg Leu Ser
            35                  40                  45

Pro His Pro Cys Leu Gln Asp Arg Lys Asp Phe Gly Leu Pro Gln Glu
            50                  55                  60

Met Val Glu Gly Ser Gln Leu Gln Lys Asp Gln Ala Ile Ser Val Leu
65                  70                  75                  80
```

<210> SEQ ID NO 30
<211> LENGTH: 1171
<212> TYPE: DNA
<213> ORGANISM: Bos taurus

<400> SEQUENCE: 30

| | | | | | |
|---|---|---|---|---|---|
| cccatctcag | ccagcccagc | agcagccaca | tcttccccat | ggccttcgtg | ctctctctac | 60 |
| tgatggccct | ggtgctggtc | agctacggcc | cgggacgatc | tctgggttgt | tacctgtctg | 120 |
| aggaccacat | gctaggtgcc | agggagaacc | tcaggctcct | ggcccgaatg | aacagactct | 180 |
| ctcctcatcc | ctgtctgcag | gacagaaaag | actttggtct | tcctcaggag | atggtggagg | 240 |
| gcagccagct | ccagaaggat | caggctatct | ctgtgctcca | cgagatgctc | cagcagtgct | 300 |
| tcaacctctt | ccacatagag | cactcgtctg | ctgcctggaa | caccacctc | ctggagcagc | 360 |
| tctgcactgg | gctccaacag | cagctggagg | acctggacgc | tgcctgggc | ccagtgatgg | 420 |
| gagagaagga | ctctgacatg | ggaaggatgg | gccccattct | gactgtgaag | aagtacttcc | 480 |

```
aggacatcca tgtctacctg aaagaaaagg aatacagtga ctgcgcctgg gaaatcatca    540
gagtggagat gatgagagcc ctctcttcat caaccacctt gcaaaaaagg ttaagaaaga    600
tgggtggaga tctgaactca ctttgagatg actctcgctg actaagatgc cacatcacct    660
tcgtacactc acctgtgttc atttcagaag actctgattt ctgcttcagc caccgaattc    720
attgaattac tttagccgat actttgtcag cagtaataag caagtagata taaaagtact    780
cagctgtagg ggcatgagtc cttaagtgat gcctgccctg atgttatctg ttgttgattt    840
atgtattcct tcttgcatct aacatactta aaatattagg atatttgtaa agttacattt    900
catttgtaca tctattaaaa tttctaaaac atgtttacca ttttgtgtta ttaaatttgt    960
cctttgttct atttattaaa tcaaagaaaa tgagtttctt tactcaaaaa ctttattatt   1020
attattaaaa ctttattaaa gaatgggtgg ttacatttgt ttattcattc attccattca   1080
tattatgcat atacattgag tacctacgtg acagactgta taattctcac caaggaatac   1140
aagtgaataa agcaaatgta gttcctactg c                                  1171

<210> SEQ ID NO 31
<211> LENGTH: 1313
<212> TYPE: DNA
<213> ORGANISM: Bos taurus

<400> SEQUENCE: 31
tttatttagt ttctcattta attgatatac atttacattg acaaacccaa attttattgg     60
gaaaattaaa tttctactgt aaaaattaag agtttagatt gactacatttt cctaggtcaa    120 acagaaaata tctaactgaa aacacaaaca ggaagtgaga gagaaatttt cggataatga    180
gtaccgtctt ccctatttaa aagccttgct tagaacgatc atcatcagag aacctacctg    240
aaggttcacc cagacccccat ctcagccagc ccagcagcag ccacatcttc cccatggcct    300
tcgtgctctc tctactgatg gccctggtgc tggtcagcta cggcccggga cgatctctgg    360
gttgttacct gtctgaggac cacatgctag gtgccaggga gaacctcagg ctcctggccc    420
gaatgaacag actctctcct catccctgtc tgcaggacag aaaagacttt ggtcttcctc    480
aggagatggt ggagggcaac cagctccaga aggatcaggc tatctctgtg ctccatgaga    540
tgctccagca gtgcctcaac ctcttctaca cagagcactc gtctgctgcc tggaacacca    600
ccctcctgga gcagctctgc actgggctcc aacagcagct ggaggacctg gacgcctgcc    660
tgggcccagt gatgggagag aaagactctg acatgggaag gatgggcccc attctgactg    720
tgaagaagta cttccagggt atccatgtct acctgaaaga aaagaatac agtgactgcg    780 cctgggaaat catcagagtg gagatgatga gagccctctc ttcatcaacc accttgcaaa    840
aaaggttaag aaagatgggt ggagatctga actcactttg agatgactct cgctgactaa    900
gatgccacat caccttcgta cactcacctg tgttcatttc agaagactct gatttctgct    960
tcagccaccg aattcattga attactttaa ctgatacttt gtcagcagca ataagcaagt   1020
agatataaaa gtactcagct gtaggggcat aagtccttaa gtgatgcctg ccctgatgtt   1080
atctgttgtt gatttatgta ttccttcttg catctaacat acttaaaata ttaggaaatt   1140
tgtaaagtta catttcattt gtacatctat taaaatttct aaaacatgtt taccattttg   1200
tgttattaaa tttgtccttt gttctatttta ttaaatcaaa gaaaatgagt tctttactc    1260 aaaaacttta ttattattat tattattaaa actttattaa agaatgggtg gtt           1313

<210> SEQ ID NO 32
<211> LENGTH: 519
```

<212> TYPE: DNA
<213> ORGANISM: Bos taurus

<400> SEQUENCE: 32

| tgttacctgt ctgaggacca catgctaggt gccagggaga acctcaggct cctggcccga | 60 |
| atgaacagac tctctcctca tccctgtctg caggacagaa aagactttgg tcttcctcag | 120 |
| gagatggtgg agggcagcca gctccagaag gatcaggcta tctctgtgct ccacgagatg | 180 |
| ctccagcagt gcttcaacct cttccacata gagcactcgt ctgctgcctg gaacaccacc | 240 |
| ctcctggagc agctctgcac tgggctccaa cagcagctgg aggacctgga cgcctgcctg | 300 |
| ggcccagtga tgggagagaa ggactctgac atgggaagga tgggccccat tctgactgtg | 360 |
| aagaagtact tccagggcat ccatgtctac ctgaaagaaa aggaatacag tgactgcgcc | 420 |
| tgggaaatca tcagagtgga gatgatgaga gccctctctt catcaaccac cttgcaaaaa | 480 |
| aggttaagaa agatgggtgg agatctgaac tcactttga | 519 |

<210> SEQ ID NO 33
<211> LENGTH: 519
<212> TYPE: DNA
<213> ORGANISM: Bos taurus

<400> SEQUENCE: 33

| tgttacctgt ctgaggacca catgctaggt gccagggaga acctcaggct cctggcccga | 60 |
| atgaacagac tctctcctca tccctgtctg caggacagaa aagactttgg tcttcctcag | 120 |
| gagatggtgg agggcaacca gctccagaag gatcaggcta tctctgtgct ccatgagatg | 180 |
| ctccagcagt gcttcaacct cttccacata gagcactcgt ctgctgcctg gaacaccacc | 240 |
| ctcctggagc agctctgcac tgggctccaa cagcagctgg aggacctgga cgcctgcctg | 300 |
| ggcccagtga tgggagagaa agactctgac atgggaagga tgggccccat tctgactgtg | 360 |
| aagaagtact tccaggacat ccatgtctac ctgaaagaaa aggaatacag tgactgcgcc | 420 |
| tgggaaatca tcagagtgga gatgatgaga gccctctctt catcaaccac cttgcaaaaa | 480 |
| aggttaagaa agatgggtgg agatctgaac tcactttga | 519 |

<210> SEQ ID NO 34
<211> LENGTH: 519
<212> TYPE: DNA
<213> ORGANISM: Bos taurus

<400> SEQUENCE: 34

| tgttacctgt ctgaggacca catgctaggt gccagggaga acctcaggct cctggcccga | 60 |
| atgaacagac tctctcctca tccctgtctg caggacagaa aagactttgg tcttcctcag | 120 |
| gagatggtgg agggcaacca gctccagaag gatcaggcta tctctgtgct ccatgagatg | 180 |
| ctccagcagt gcctcaacct cttctacaca gagcactcgt ctgctgcctg gaacaccacc | 240 |
| ctcctggagc agctctgcac tgggctccaa cagcagctgg aggacctgga cgcctgcctg | 300 |
| ggcccagtga tgggagagaa agactctgac atgggaagga tgggccccat tctgactgtg | 360 |
| aagaagtact tccaggacat ccatgtctac ctgaaagaaa aggaatacag tgactgcgcc | 420 |
| tgggaaatca tcagagtgga gatgatgaga gccctctctt catcaaccac cttgcaaaaa | 480 |
| aggttaagaa agatgggtgg agatctgaac tcactttga | 519 |

<210> SEQ ID NO 35
<211> LENGTH: 519
<212> TYPE: DNA

<213> ORGANISM: Bos taurus

<400> SEQUENCE: 35

| | | | | | |
|---|---|---|---|---|---|
| tgttacctgt | ctgaggacca | catgctaggt | gccagggaga | acctcaggct | cctggcccga | 60 |
| atgaacagac | tctctcctca | tccctgtctg | caggacagaa | aagactttgg | tcttcctcag | 120 |
| gagatggtgg | agggcaacca | gctccagaag | gatcaggcta | tctctgtgct | ccatgagatg | 180 |
| ctccagcagt | gcttcaacct | cttctacaca | gagcactcgt | ctgctgcctg | gaacaccacc | 240 |
| ctcctggagc | agctctgcac | tgggctccaa | cagcagctgg | aggacctgga | cgcctgcctg | 300 |
| ggcccagtga | tgggagagaa | agactctgac | atgggaagga | tgggcccat | tctgactgtg | 360 |
| aagaagtact | tccaggacat | ccatgtctac | ctgaaagaaa | aagaatacag | tgactgcgcc | 420 |
| tgggaaatca | tcagagtgga | gatgatgaga | gccctctctt | catcaaccac | cttgcaaaaa | 480 |
| aggttaagaa | agatgggtgg | agatctgaac | tcactttga | | | 519 |

<210> SEQ ID NO 36
<211> LENGTH: 519
<212> TYPE: DNA
<213> ORGANISM: Bos taurus

<400> SEQUENCE: 36

| | | | | | |
|---|---|---|---|---|---|
| tgttacctgt | ctgaggacca | catgctaggt | gccagggaga | acctcaggct | cctggcccga | 60 |
| atgaacagac | tctctcctca | tccctgtctg | caggacagaa | aagactttgg | tcttcctcag | 120 |
| gagatggtgg | agggcagcca | gctccagaag | gatcaggcta | tctctgtgct | ccatgagatg | 180 |
| ctccagcagt | gcctcaacct | cttctacaca | gagcactcgt | ctgctgcctg | gaacaccacc | 240 |
| ctcctggagc | agctctgcac | tgggctccaa | cagcagctgg | aggacctgga | cgcctgcctg | 300 |
| ggcccagtga | tgggagagaa | agactctgac | atgggaagga | tgggcccat | tctgactgtg | 360 |
| aagaagtact | tccagggcat | ccatgtctac | ctgaaagaaa | aagaatacag | tgactgcgcc | 420 |
| tgggaaatca | tcagagtgga | gatgatgaga | gccctctctt | catcaaccac | cttgcaaaaa | 480 |
| aggttaagaa | agatgggtgg | agatctgaac | tcactttga | | | 519 |

<210> SEQ ID NO 37
<211> LENGTH: 519
<212> TYPE: DNA
<213> ORGANISM: Bos taurus

<400> SEQUENCE: 37

| | | | | | |
|---|---|---|---|---|---|
| tgttacctgt | ctgaggacca | catgctaggt | gccagggaga | acctcaggct | cctggcccga | 60 |
| atgaacagac | tctctcctca | tccctgtctg | caggacagaa | aagactttgg | tcttcctcag | 120 |
| gagatggtgg | agggcaacca | gctccagaag | gatcaggcta | tctctgtgct | ccacgagatg | 180 |
| ctccagcagt | gcctcaacct | cttctacaca | gagcactcgt | ctgctgcctg | gaacaccacc | 240 |
| ctcctggagc | agctctgcac | tgggctccaa | cagcagctgg | aggacctgga | cgcctgcctg | 300 |
| ggcccagtga | tgggagagaa | agactctgac | atgggaagga | tgggcccat | tctgactgtg | 360 |
| aagaagtact | tccagggtat | ccatgtctac | ctgaaagaaa | aagaatacag | tgactgcgcc | 420 |
| tgggaaatca | tcagaatgga | gatgatgaga | gccctctctt | catcaaccac | cttgcaaaaa | 480 |
| aggttaagaa | agatgggtgg | agatctgaac | tcactttga | | | 519 |

<210> SEQ ID NO 38
<211> LENGTH: 519
<212> TYPE: DNA
<213> ORGANISM: Bos taurus

```
<400> SEQUENCE: 38
tgttacctgt ctgaggacca catgctaggt gccagggaga acctcaggct cctggcccga      60
atgaacagac tctctcctca tccctgtctg caggacagaa aagactttgg tcttcctcag     120
gagatggtgg agggcagccc gctccagaag gatcaggcta tctctgtgct ccacgagatg     180
ctccagcagt gcttcaacct cttccacata gagcactcgt ctgctgcctg aacaccacc     240 ctcctggagc agctctgcac tgggctccaa cagcagctgg aggacctgga cgcctgcctg     300
ggcccagtga tgggagagaa agactctgac atgggaagga tgggccccat tctgactgtg     360
aagaagtact tccagggcat ccatgtctac ctgaaagaaa aagaatacag tgactgcgcc     420
tgggaaatca tcagaatgga gatgatgaga gccctctctt catcaaccac cttgcaaaaa     480
aggttaagaa agatgggtgg agatctgaac tcactttga                            519

<210> SEQ ID NO 39
<211> LENGTH: 519
<212> TYPE: DNA
<213> ORGANISM: Bos taurus

<400> SEQUENCE: 39
tgttacctgt ctgaggacca catgctaggt gccagggaga acctcaggct cctggcccga      60
atgaacagac tctctcctca tccctgtctg caggacagaa aagactttgg tcttcctcag     120
gagatggtgg agggcaacca gctccagaag gatcaggcta tctctgtgct ccatgagatg     180
ctccagcagt gcttcaacct cttctacaca gagcactcgt ctgctgcctg aacaccacc     240 ctcctggagc agctctgcac tgggctccaa cagcagctgg aggacctgga cgcctgcctg     300
ggcccagtga tgggagagaa agactctgac atgggaagga tgggccccat tctgactgtg     360
aagaagtact tccagggcat ccatgtctac ctgaaagaaa aagaatacag tgactgcgcc     420
tgggaaatca tcagaacgga gatgatgaga gccctctctt catcaaccac cttgcaaaaa     480
aggttaagaa agatgggtgg agatctgaac tcactttga                            519

<210> SEQ ID NO 40
<211> LENGTH: 519
<212> TYPE: DNA
<213> ORGANISM: Bos taurus

<400> SEQUENCE: 40
tgttacctgt ctgaggacca catgctaggt gccagggaga acctcaggct cctggcccga      60
atgaacagac tctctcctca tccctgtctg caggacagaa aagactttgg tcttcctcag     120
gagatggtgg agggcaacca actccagaag gatcaggcta tctctgtgct ccatgagatg     180
ctccagcagt gcttcaacct cttctacaca gagcactcgt ctgctgcctg aacaccacc     240 ctcctggagc agccctgcac tgggctccaa cagcagctgg aggacctgga cgcctgcctg     300
ggcccagtga tgggagagaa agactctgac atgggaagga tgggccccat tctgactgtg     360
aagaagtact tccagggcat ccatgtctac ctgaaagaaa aagaatacag tgactgcgcc     420
tgggaaatca tcagaatgga gatgatgaga gccctctctt catcaaccac cttgcaaaaa     480
aggttaagaa agatgggtgg agatctgaac tcactttga                            519

<210> SEQ ID NO 41
<211> LENGTH: 168
<212> TYPE: PRT
<213> ORGANISM: Ovis aries
```

-continued

<400> SEQUENCE: 41

Gly Pro Gly Gly Ser Leu Gly Cys Tyr Leu Ser Gln Arg Leu Met Leu
1               5                   10                  15

Asp Ala Arg Glu Asn Leu Arg Leu Leu Asp Arg Met Asn Arg Pro Ser
            20                  25                  30

Pro His Ser Cys Leu Gln Asp Arg Lys Asp Phe Gly Leu Pro Gln Glu
        35                  40                  45

Met Val Glu Gly Asp Gln Leu Gln Glu Ala Gln Ala Phe Cys Val Leu
    50                  55                  60

Tyr Glu Met Leu Gln Gln Ser Phe Asn Leu Phe His Thr Glu Arg Ser
65                  70                  75                  80

Ser Ala Ala Trp Asn Thr Thr Leu Leu Glu Gln Leu Cys Thr Gly Leu
                85                  90                  95

Gln Gln Gln Leu Glu Asp Leu Asp Thr Cys Arg Gly Pro Val Met Gly
            100                 105                 110

Glu Lys Asp Ser Glu Leu Gly Lys Met Asp Pro Ile Val Thr Val Lys
        115                 120                 125

Lys Tyr Phe Gln Gly Ile His Asp Tyr Leu Gln Glu Lys Gly Tyr Ser
    130                 135                 140

Asp Cys Ala Trp Glu Thr Val Arg Val Glu Met Met Arg Ala Leu Thr
145                 150                 155                 160

Ser Ser Thr Thr Leu Lys Lys Gly
                165

<210> SEQ ID NO 42
<211> LENGTH: 172
<212> TYPE: PRT
<213> ORGANISM: Ovis aries

<400> SEQUENCE: 42

Cys Tyr Leu Ser Gln Arg Leu Met Leu Asp Ala Arg Glu Asn Leu Arg
1               5                   10                  15

Leu Leu Asp Arg Met Asn Arg Leu Ser Pro His Ser Cys Leu Gln Asp
            20                  25                  30

Arg Lys Asp Phe Gly Leu Pro Gln Glu Met Val Glu Gly Asp Gln Leu
        35                  40                  45

Gln Lys Asp Gln Ala Phe Ser Val Leu Tyr Glu Met Leu Gln Gln Thr
    50                  55                  60

Phe Asn Leu Phe Tyr Thr Glu His Ser Ser Ala Ala Trp Asp Thr Thr
65                  70                  75                  80

Leu Leu Glu Gln Leu Arg Thr Gly Leu Gln Gln Gln Leu Glu Asp Leu
                85                  90                  95

Asp Thr Ser Arg Gly Pro Val Met Gly Glu Lys Asp Ser Glu Leu Gly
            100                 105                 110

Lys Met Asp Pro Ile Val Thr Val Lys Lys Tyr Phe Gln Gly Ile His
        115                 120                 125

Asp Tyr Leu Gln Glu Lys Glu Tyr Ser Asp Cys Ala Trp Glu Ile Val
    130                 135                 140

Arg Val Glu Met Met Arg Ala Leu Thr Ser Ser Thr Thr Leu Gln Lys
145                 150                 155                 160

Arg Leu Thr Lys Met Gly Gly Asp Leu Asn Ser Pro
                165                 170

<210> SEQ ID NO 43
<211> LENGTH: 195

```
<212> TYPE: PRT
<213> ORGANISM: Ovis aries

<400> SEQUENCE: 43
```

Met Ala Phe Val Leu Ser Leu Met Ala Leu Val Leu Val Ser Tyr
1               5                   10                  15

Gly Pro Gly Gly Ser Leu Gly Cys Tyr Leu Ser Arg Lys Leu Met Leu
            20                  25                  30

Asp Ala Arg Glu Asn Leu Arg Leu Leu Asp Arg Met Asn Arg Leu Ser
            35                  40                  45

Pro His Ser Cys Leu Gln Asp Arg Lys Asp Phe Gly Leu Pro Gln Glu
            50                  55                  60

Met Val Glu Gly Asp Gln Leu Gln Lys Asp Gln Ala Phe Ser Val Leu
65                  70                  75                  80

Tyr Glu Met Leu Gln Gln Ser Phe Asn Val Phe His Thr Glu His Ser
                85                  90                  95

Ser Ala Ala Trp Asn Thr Thr Leu Leu Glu Gln Leu Cys Thr Gly Leu
            100                 105                 110

Gln Gln Gln Leu Asp His Leu Asp Thr Cys Arg Gly Pro Val Met Gly
            115                 120                 125

Glu Lys Asp Ser Glu Leu Gly Lys Met Asp Pro Ile Val Thr Val Lys
130                 135                 140

Lys Tyr Phe Gln Gly Ile His Asp Tyr Leu Gln Glu Lys Gly Tyr Ser
145                 150                 155                 160

Asp Cys Ala Trp Glu Ile Val Arg Val Glu Met Met Arg Ala Leu Thr
                165                 170                 175

Ser Ser Thr Thr Leu Gln Lys Arg Leu Thr Lys Met Gly Gly Asp Leu
            180                 185                 190

Asn Ser Pro
        195

```
<210> SEQ ID NO 44
<211> LENGTH: 195
<212> TYPE: PRT
<213> ORGANISM: Ovis aries

<400> SEQUENCE: 44
```

Met Ala Phe Val Leu Ser Leu Met Ala Leu Val Leu Val Ser Tyr
1               5                   10                  15

Gly Pro Gly Gly Ser Leu Gly Cys Tyr Leu Ser Gln Arg Leu Met Leu
            20                  25                  30

Asp Ala Arg Glu Asn Leu Arg Leu Leu Asp Arg Met Asn Arg Leu Ser
            35                  40                  45

Pro His Ser Cys Leu Gln Asp Arg Lys Asp Phe Gly Leu Pro Gln Glu
            50                  55                  60

Met Val Glu Gly Asp Gln Leu Gln Lys Asp Gln Ala Phe Pro Val Leu
65                  70                  75                  80

Tyr Glu Met Leu Gln Gln Ser Phe Asn Leu Phe Tyr Thr Glu His Ser
                85                  90                  95

Ser Ala Ala Trp Asp Thr Thr Leu Leu Glu Gln Leu Cys Thr Gly Leu
            100                 105                 110

Gln Gln Gln Leu Asp His Leu Asp Thr Cys Arg Gly Gln Val Met Gly
            115                 120                 125

Glu Lys Asp Ser Glu Leu Gly Asn Met Asp Pro Ile Val Thr Val Lys
130                 135                 140

```
Lys Tyr Phe Gln Gly Ile His Asp Tyr Leu Gln Glu Lys Gly Tyr Ser
145                 150                 155                 160

Asp Cys Ala Trp Glu Ile Val Arg Val Glu Met Met Arg Ala Leu Thr
                165                 170                 175

Ser Ser Thr Thr Leu Gln Lys Arg Leu Thr Lys Met Gly Gly Asp Leu
            180                 185                 190

Asn Ser Pro
        195

<210> SEQ ID NO 45
<211> LENGTH: 195
<212> TYPE: PRT
<213> ORGANISM: Ovis aries

<400> SEQUENCE: 45

Met Ala Phe Val Leu Ser Leu Leu Met Ala Leu Val Leu Val Ser Tyr
1               5                   10                  15

Gly Pro Gly Gly Ser Leu Gly Cys Tyr Leu Ser Gln Arg Leu Met Leu
            20                  25                  30

Asp Ala Arg Glu Asn Leu Lys Leu Leu Asp Arg Met Asn Arg Leu Ser
        35                  40                  45

Pro His Ser Cys Leu Gln Asp Arg Lys Asp Phe Gly Leu Pro Gln Glu
    50                  55                  60

Met Val Glu Gly Asp Gln Leu Gln Lys Asp Gln Ala Phe Pro Val Leu
65                  70                  75                  80

Tyr Glu Met Leu Gln Gln Ser Phe Asn Leu Phe Tyr Thr Glu His Ser
                85                  90                  95

Ser Ala Ala Trp Asp Thr Thr Leu Leu Asp Gln Leu Cys Thr Gly Leu
            100                 105                 110

Gln Gln Gln Leu Asp His Leu Asp Thr Cys Arg Gly Gln Val Met Gly
        115                 120                 125

Glu Glu Asp Ser Glu Leu Gly Asn Met Asp Pro Ile Val Thr Val Lys
    130                 135                 140

Lys Tyr Phe Gln Gly Ile Tyr Asp Tyr Leu Gln Glu Lys Gly Tyr Ser
145                 150                 155                 160

Asp Cys Ala Trp Glu Ile Val Arg Val Glu Met Met Arg Ala Leu Thr
                165                 170                 175

Val Ser Thr Thr Leu Gln Lys Arg Leu Thr Lys Met Gly Gly Asp Leu
            180                 185                 190

Asn Ser Pro
        195

<210> SEQ ID NO 46
<211> LENGTH: 195
<212> TYPE: PRT
<213> ORGANISM: Ovis aries

<400> SEQUENCE: 46

Met Ala Phe Val Leu Ser Leu Leu Met Ala Leu Val Leu Val Ser Tyr
1               5                   10                  15

Gly Pro Gly Gly Ser Leu Gly Cys Tyr Leu Ser Gln Arg Leu Met Leu
            20                  25                  30

Asp Ala Lys Glu Asn Leu Lys Leu Leu Asp Arg Met Asn Arg Leu Ser
        35                  40                  45

Pro His Ser Cys Leu Gln Asp Arg Lys Asp Phe Gly Leu Pro Gln Glu
    50                  55                  60
```

```
Met Val Glu Gly Asp Gln Leu Gln Lys Asp Gln Ala Phe Pro Val Leu
 65                  70                  75                  80

Tyr Glu Met Leu Gln Gln Ser Phe Asn Leu Phe Tyr Thr Glu His Ser
                 85                  90                  95

Ser Ala Ala Trp Asp Thr Thr Leu Leu Glu Gln Leu Cys Thr Gly Leu
                100                 105                 110

Gln Gln Gln Leu Asp His Leu Asp Thr Cys Arg Asp Gln Val Met Gly
                115                 120                 125

Glu Lys Asp Ser Glu Leu Gly Asn Val Asp Pro Ile Val Thr Val Lys
            130                 135                 140

Lys Tyr Phe Gln Gly Ile His Asp Tyr Leu Gln Glu Lys Gly Tyr Ser
145                 150                 155                 160

Asp Cys Ala Trp Glu Ile Val Arg Val Glu Met Met Arg Ala Leu Thr
                165                 170                 175

Val Ser Thr Thr Leu Gln Lys Arg Leu Thr Lys Met Gly Gly Asp Leu
                180                 185                 190

Asn Ser Pro
        195

<210> SEQ ID NO 47
<211> LENGTH: 195
<212> TYPE: PRT
<213> ORGANISM: Ovis aries

<400> SEQUENCE: 47

Met Ala Phe Val Leu Ser Leu Leu Met Ala Leu Val Leu Val Ser Tyr
  1               5                  10                  15

Gly Pro Gly Gly Ser Leu Gly Cys Tyr Leu Ser Arg Lys Leu Met Leu
                 20                  25                  30

Asp Ala Arg Glu Asn Leu Arg Leu Leu Asp Arg Met Asn Arg Leu Ser
                 35                  40                  45

Pro His Ser Cys Leu Gln Asp Arg Lys Asp Phe Gly Leu Pro Gln Glu
             50                  55                  60

Met Val Glu Gly Asp Gln Leu Gln Lys Asp Gln Ala Phe Ser Val Leu
 65                  70                  75                  80

Tyr Glu Met Leu Gln Gln Ser Phe Asn Val Phe His Thr Glu Arg Ser
                 85                  90                  95

Ser Ala Ala Trp Asn Thr Thr Leu Leu Glu Gln Leu Cys Thr Gly Leu
                100                 105                 110

Gln Gln Gln Leu Asp His Leu Asp Thr Cys Arg Gly Pro Val Met Gly
                115                 120                 125

Glu Lys Asp Ser Glu Leu Gly Lys Met Asp Pro Ile Val Thr Val Lys
            130                 135                 140

Lys Tyr Phe Gln Gly Ile His Asp Tyr Leu Gln Glu Lys Gly Tyr Ser
145                 150                 155                 160

Asp Cys Ala Trp Glu Ile Val Arg Val Glu Met Met Arg Ala Leu Thr
                165                 170                 175

Ser Ser Thr Thr Leu Gln Lys Arg Leu Thr Lys Thr Gly Gly Asp Leu
                180                 185                 190

Asn Ser Pro
        195

<210> SEQ ID NO 48
<211> LENGTH: 519
<212> TYPE: DNA
<213> ORGANISM: Ovis aries
```

<400> SEQUENCE: 48

```
tgttacctat ctcggaaact catgctggat gccagggaga acctcaggct cctggaccga    60
atgaacagac tgtcacctca ttcctgtctg caggacagaa aagactttgg tcttccccag   120
gagatggtgg agggcgacca gctccagaag gaccaggcct tctctgtgct ctacgagatg   180
ctccagcaga gcttcaacgt cttccacaca gagcgctcct ctgctgcctg aacaccacc    240
ctcctggagc agctctgcac tggactccaa cagcagctgg accacctgga cacctgcagg   300
ggtcccgtga tgggagagga agactctgaa ctgggtaaca tggaccccat tgtgaccgtg   360
aagaagtact tccagggcat ccatgactac ctgcaagaga agggatacag cgactgcgcc   420
tgggaaatcg tcagagtcga gatgatgaga gccctcactt catcaaccac cttgcaaaaa   480
aggttaacaa agacgggtgg agatctgaac tcaccttga                          519
```

<210> SEQ ID NO 49
<211> LENGTH: 519
<212> TYPE: DNA
<213> ORGANISM: Ovis aries

<400> SEQUENCE: 49

```
tgttacctat ctcggaaact catgctggat gccagggaga acctcaggct cctggaccga    60
atgaacagac tgtcacctca ttcctgtctg caggacagaa aagactttgg tcttccccag   120
gagatggtgg agggcgacca gctccagaag gaccaggcct tctctgtgct ctacgagatg   180
ctccagcaga gcttcaacgt cttccacaca gagcgctcct ctgctgcctg aacaccacc    240
ctcctggagc agctctgcac tggactccaa cagcagctgg accacctgga cacctgcagg   300
ggtcccgtga tgggagagaa agactctgaa ctgggtaaca tggaccccat tgtgaccgtg   360
aagaagtact tccagggcat ccatgactac ctgcaagaga agggatacag cgactgcgcc   420
tgggaaatcg tcagagtcga gatgatgaga gccctcactt catcaaccac cttgcaaaaa   480
aggttaacaa agacgggtgg agatctgaac tcaccttga                          519
```

<210> SEQ ID NO 50
<211> LENGTH: 519
<212> TYPE: DNA
<213> ORGANISM: Ovis aries

<400> SEQUENCE: 50

```
tgttacctat ctcagagact catgctggat gccagggaga acctcaagct cctggaccga    60
atgaacagac tctcccctca ttcctgtctg caggacagaa aagactttgg tcttccccag   120
gagatggtgg agggcgacca gctccagaag gaccaggcct tccctgtgct ctacgagatg   180
ctccagcaga gcttcaacct cttctacaca gagcactcct ctgctgcctg gacaccacc    240
ctcctggagc agctctgcac tggactccaa cagcagctgg accacctgga cacctgcagg   300
ggtcaagtga tgggagagaa agactctgaa ctgggtaaca tggaccccat tgtgaccgtg   360
aagaagtact tccagggcat ctatgactac ctgcaagaga agggatacag cgactgcgcc   420
tgggaaatcg tcagagtcga gatgatgaga gccctcactg tatcaaccac cttgcaaaaa   480
aggttaacaa agatgggtgg agatctgaac tcaccttga                          519
```

<210> SEQ ID NO 51
<211> LENGTH: 519
<212> TYPE: DNA
<213> ORGANISM: Ovis aries

```
<400> SEQUENCE: 51
tgttacctat ctgagagact catgctagat gccagggaga acctcaagct cctggaccga      60
atgaacagac tctcccctca ttcctgtctg caggacagaa aagactttgg tcttccccag     120
gagatggtgg agggcgacca gctccagaag gaccaggcct ccctgtgct ctacgagatg      180 ctccagcaga gcttcaacct cttctacaca gagcactcct ctgctgcctg ggacaccacc     240
ctcctggagc agctctgcag tggactccaa cagcagctgg accacctgga cacctgcagg     300
ggtcaagtga tgggagagga agactctgaa ctgggtaaca tggaccccat tgtgaccgtg     360
aagaagtact cccagggcat ctatgactac ctgcaagaga agggatacag cgactgcgcc     420
tgggaaatcg tcagagtcga gatgatgaga gccctcactg tatcaaccac cttgcaaaaa     480
aggttaacaa agatgggtgg agatctgaac tcaccttga                            519

<210> SEQ ID NO 52
<211> LENGTH: 519
<212> TYPE: DNA
<213> ORGANISM: Ovis aries

<400> SEQUENCE: 52
tgttacctat ctcagagact catgctggat gccagggaga acctcaagct cctggaccga      60
atgaacagac tctcccctca ttcctgtctg caggacagaa aagactttgg tcttccccag     120
gagatggtgg agggcgacca gctccagaag gaccaggcct ccctgtgct ctacgagatg      180 ctccagcaga gcttcaacct cttctacaca gagcactcct ctgctgcctg ggacaccacc     240
ctcctggagc agctctgcac tggactccaa cagcagctgg accacctgga cacctgcagg     300
ggtcaagtga tgggagagga agactctgaa ctgggtaaca tggaccccat tgtgaccgtg     360
aagaagtact ccagggcat ctacgactac ctgcaagaga agggatacag cgactgcgcc     420
tgggaaatcg tcagagtcga gatgatgaga gccctcactg tatcaaccac cttgcaaaaa     480
aggttaacaa agatgggtgg agatctgaac tcaccttga                            519

<210> SEQ ID NO 53
<211> LENGTH: 519
<212> TYPE: DNA
<213> ORGANISM: Ovis aries

<400> SEQUENCE: 53
tgttacctat ctgagagact catgctggat gccagggaga acctcaagct cctggaccga      60
atgaacagac tctcccctca ttcctgtctg caggacagaa aagactttgg tcttccccag     120
gagatggtgg agggcgacca gctccagaag gaccaggcct ccctgtgct ctacgagatg      180 ctccagcaga gcttcaacct cttctacaca gagcactcct ctgctgcctg ggacaccacc     240
ctcctggagc agctctgcac tggactccaa cagcagctgg accacctgga cacctgcagg     300
ggtcaagtga tgggagagga agactctgaa ctgggtaaca tggaccccat tgtgacggtg     360
aagaagtact cgagggcat ctatgaccta ctgcaagaga agggatacag cgactgcgcc     420
tgggaaatcg tcagagtcga gatgatgaga gccctcactg tatcaaccac cttgcaaaaa     480
aggttaacaa agatgggtgg agatctgaac tcaccttga                            519
```